United States Patent
Vendely et al.

(10) Patent No.: US 12,369,915 B2
(45) Date of Patent: Jul. 29, 2025

(54) COMPRESSIBLE ADJUNCT WITH CROSSING SPACER FIBERS

(71) Applicant: Cilag GmbH International, Zug (CH)

(72) Inventors: Michael J. Vendely, Lebanon, OH (US); Frederick E. Shelton, IV, Hillsboro, OH (US); Jason L. Harris, Lebanon, OH (US); Charles J. Scheib, Loveland, OH (US); Howell T. Goldrein, Cambridge (GB); Robert S. Moir, Cambridge (GB); Sofia Maria Consonni, Brimingham (GB); Ismail Akram, Cambridge (GB); Ashley D. Easter, Cambridge (GB); Helen S. Latham, Cambridge (GB)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/609,804

(22) Filed: Mar. 19, 2024

(65) Prior Publication Data
US 2024/0366224 A1    Nov. 7, 2024

Related U.S. Application Data

(63) Continuation of application No. 18/081,335, filed on Dec. 14, 2022, now Pat. No. 11,944,308, which is a
(Continued)

(51) Int. Cl.
*A61B 17/072* (2006.01)
*A61B 17/00* (2006.01)
(Continued)

(52) U.S. Cl.
CPC ...... *A61B 17/105* (2013.01); *A61B 17/00491* (2013.01); *A61B 17/0644* (2013.01);
(Continued)

(58) Field of Classification Search
CPC ..... A61B 17/105; A61L 17/105; A61L 17/12; B05D 1/007; B05D 1/30; B32B 3/02;
(Continued)

(56) References Cited

U.S. PATENT DOCUMENTS

| 5,403,312 A | 4/1995 | Yates et al. |
| 7,000,818 B2 | 2/2006 | Shelton, IV et al. |

(Continued)

FOREIGN PATENT DOCUMENTS

| CN | 103648410 B | 10/2016 |
| CN | 104349800 B | 11/2017 |

(Continued)

*Primary Examiner* — Nathaniel C Chukwurah

(57) ABSTRACT

A staple cartridge assembly for use with a surgical stapling instrument includes a staple cartridge including a plurality of staples and a cartridge deck. The staple cartridge assembly also includes a compressible adjunct positionable against the cartridge deck, wherein the staples are deployable into tissue captured against the compressible adjunct, and wherein the compressible adjunct comprises a first biocompatible layer comprising a first portion, a second biocompatible layer comprising a second portion, and crossed spacer fibers extending between the first portion and the second portion.

20 Claims, 44 Drawing Sheets

Related U.S. Application Data continuation of application No. 17/186,335, filed on Feb. 26, 2021, now Pat. No. 11,712,244, which is a continuation of application No. 16/229,607, filed on Dec. 21, 2018, now Pat. No. 10,932,779, which is a continuation of application No. 14/871,071, filed on Sep. 30, 2015, now Pat. No. 10,433,846.

(51) Int. Cl.

| | | |
|---|---|---|
| *A61B 17/064* | (2006.01) | |
| *A61B 17/068* | (2006.01) | |
| *A61B 17/08* | (2006.01) | |
| *A61B 17/10* | (2006.01) | |
| *A61B 17/32* | (2006.01) | |
| *A61L 17/10* | (2006.01) | |
| *A61L 17/12* | (2006.01) | |
| *B05D 1/00* | (2006.01) | |
| *B05D 1/30* | (2006.01) | |
| *B29C 48/16* | (2019.01) | |
| *B32B 3/02* | (2006.01) | |
| *B32B 3/08* | (2006.01) | |
| *B32B 3/20* | (2006.01) | |
| *B32B 3/26* | (2006.01) | |
| *B32B 5/02* | (2006.01) | |
| *B32B 5/10* | (2006.01) | |
| *B32B 5/12* | (2006.01) | |
| *B32B 5/18* | (2006.01) | |
| *B32B 5/24* | (2006.01) | |
| *B32B 5/26* | (2006.01) | |
| *B32B 7/05* | (2019.01) | |
| *D01D 5/00* | (2006.01) | |
| *D01D 5/18* | (2006.01) | |
| *D04H 1/56* | (2006.01) | |
| *B29C 44/34* | (2006.01) | |
| *B29C 48/00* | (2019.01) | |
| *B29C 48/05* | (2019.01) | |
| *B29L 31/00* | (2006.01) | |

(52) U.S. Cl.
CPC .......... *A61B 17/068* (2013.01); *A61B 17/072* (2013.01); *A61B 17/07207* (2013.01); *A61B 17/07292* (2013.01); *A61B 17/08* (2013.01); *A61B 17/32* (2013.01); *A61L 17/105* (2013.01); *A61L 17/12* (2013.01); *B05D 1/007* (2013.01); *B05D 1/30* (2013.01); *B29C 48/16* (2019.02); *B32B 3/02* (2013.01); *B32B 3/08* (2013.01); *B32B 3/20* (2013.01); *B32B 3/266* (2013.01); *B32B 5/024* (2013.01); *B32B 5/026* (2013.01); *B32B 5/10* (2013.01); *B32B 5/12* (2013.01); *B32B 5/18* (2013.01); *B32B 5/245* (2013.01); *B32B 5/26* (2013.01); *B32B 7/05* (2019.01); *D01D 5/0023* (2013.01); *D01D 5/18* (2013.01); *D04H 1/565* (2013.01); *A61B 2017/00004* (2013.01); *A61B 2017/00477* (2013.01); *A61B 2017/00526* (2013.01); *A61B 2017/00831* (2013.01); *A61B 2017/00862* (2013.01); *A61B 2017/00893* (2013.01); *A61B 2017/00955* (2013.01); *A61B 2017/00964* (2013.01); *A61B 2017/07214* (2013.01); *A61B 2017/07221* (2013.01); *A61B 2017/07228* (2013.01); *A61B 2017/07235* (2013.01); *A61B 2017/07242* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01); *A61L 2420/02* (2013.01); *B29C 44/3453* (2013.01); *B29C 44/358* (2013.01); *B29C 48/0012* (2019.02); *B29C 48/0022* (2019.02); *B29C 48/05* (2019.02); *B29L 2031/753* (2013.01); *B29L 2031/7546* (2013.01); *B32B 2250/03* (2013.01); *B32B 2250/40* (2013.01); *B32B 2307/50* (2013.01); *B32B 2307/54* (2013.01); *B32B 2307/72* (2013.01); *B32B 2307/732* (2013.01); *B32B 2307/736* (2013.01); *B32B 2535/00* (2013.01); *D10B 2331/041* (2013.01); *D10B 2509/00* (2013.01)

(58) Field of Classification Search
CPC ........... B32B 3/08; B32B 3/266; B32B 5/024; B32B 5/026; B32B 5/10; B32B 5/12; B32B 5/18; B32B 5/245; D01D 5/0023; D01D 5/18; D04H 1/565
See application file for complete search history.

(56) References Cited

U.S. PATENT DOCUMENTS

| | | |
|---|---|---|
| 7,422,139 B2 | 9/2008 | Shelton, IV et al. |
| 7,464,849 B2 | 12/2008 | Shelton, IV et al. |
| 7,500,979 B2 | 3/2009 | Hueil et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,753,245 B2 | 7/2010 | Boudreaux et al. |
| 7,845,537 B2 | 12/2010 | Shelton, IV et al. |
| 7,934,630 B2 | 5/2011 | Shelton, IV et al. |
| 7,980,443 B2 | 7/2011 | Scheib et al. |
| 8,062,330 B2 | 11/2011 | Prommersberger et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,317,070 B2 | 11/2012 | Hueil et al. |
| 8,393,514 B2 | 3/2013 | Shelton, IV et al. |
| 8,464,923 B2 | 6/2013 | Shelton, IV |
| 8,474,677 B2 | 7/2013 | Woodard, Jr. et al. |
| 8,529,600 B2 | 9/2013 | Woodard, Jr. et al. |
| 8,561,870 B2 | 10/2013 | Baxter, III et al. |
| 8,567,656 B2 | 10/2013 | Shelton, IV et al. |
| 8,608,045 B2 | 12/2013 | Smith et al. |
| 8,636,187 B2 | 1/2014 | Hueil et al. |
| 8,657,176 B2 | 2/2014 | Shelton, IV et al. |
| 8,733,613 B2 | 5/2014 | Huitema et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,535 B2 | 6/2014 | Shelton, IV et al. |
| 8,752,699 B2 | 6/2014 | Morgan et al. |
| 8,757,465 B2 | 6/2014 | Woodard, Jr. et al. |
| 8,763,877 B2 | 7/2014 | Schall et al. |
| 8,777,004 B2 | 7/2014 | Shelton, IV et al. |
| 8,783,542 B2 | 7/2014 | Riestenberg et al. |
| 8,789,741 B2 | 7/2014 | Baxter, III et al. |
| 8,800,838 B2 | 8/2014 | Shelton, IV |
| 8,814,024 B2 | 8/2014 | Woodard, Jr. et al. |
| 8,840,003 B2 | 9/2014 | Morgan et al. |
| 8,857,694 B2 | 10/2014 | Shelton, IV et al. |
| 8,864,007 B2 | 10/2014 | Widenhouse et al. |
| 8,864,009 B2 | 10/2014 | Shelton, IV et al. |
| 8,893,949 B2 | 11/2014 | Shelton, IV et al. |
| 8,899,463 B2 | 12/2014 | Schall et al. |
| 8,925,782 B2 | 1/2015 | Shelton, IV |
| 8,978,954 B2 | 3/2015 | Shelton, IV et al. |
| 8,978,956 B2 | 3/2015 | Schall et al. |
| 9,016,542 B2 | 4/2015 | Shelton, IV et al. |
| 9,033,203 B2 | 5/2015 | Woodard, Jr. et al. |
| 9,044,227 B2 | 6/2015 | Shelton, IV et al. |
| 9,044,228 B2 | 6/2015 | Woodard, Jr. et al. |
| 9,050,084 B2 | 6/2015 | Schmid et al. |
| 9,055,941 B2 | 6/2015 | Schmid et al. |
| 9,072,535 B2 | 7/2015 | Shelton, IV et al. |
| 9,101,358 B2 | 8/2015 | Kerr et al. |

(56) References Cited

U.S. PATENT DOCUMENTS

| | | |
|---|---|---|
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,119,898 B2 | 9/2015 | Bayon et al. |
| 9,168,038 B2 | 10/2015 | Shelton, IV et al. |
| 9,198,662 B2 | 12/2015 | Barton et al. |
| 9,204,880 B2 | 12/2015 | Baxter, III et al. |
| 9,211,120 B2 | 12/2015 | Scheib et al. |
| 9,216,019 B2 | 12/2015 | Schmid et al. |
| 9,220,500 B2 | 12/2015 | Swayze et al. |
| 9,220,501 B2 | 12/2015 | Baxter et al. |
| 9,232,941 B2 | 1/2016 | Mandakolathur Vasudevan et al. |
| 9,237,891 B2 | 1/2016 | Shelton, IV |
| 9,241,714 B2 | 1/2016 | Timm et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,320,523 B2 | 4/2016 | Shelton, IV et al. |
| 9,332,974 B2 | 5/2016 | Henderson et al. |
| 9,332,984 B2 | 5/2016 | Weaner et al. |
| 9,345,481 B2 | 5/2016 | Hall et al. |
| 9,351,730 B2 | 5/2016 | Schmid et al. |
| 9,364,233 B2 | 6/2016 | Alexander, III et al. |
| 9,386,984 B2 | 7/2016 | Aronhalt et al. |
| 9,386,988 B2 | 7/2016 | Baxter, III et al. |
| 9,414,838 B2 | 8/2016 | Shelton, IV et al. |
| 9,433,419 B2 | 9/2016 | Gonzalez et al. |
| 9,480,476 B2 | 11/2016 | Aldridge et al. |
| 9,510,925 B2 | 12/2016 | Hotter et al. |
| 9,517,063 B2 | 12/2016 | Swayze et al. |
| 9,566,061 B2 | 2/2017 | Aronhalt et al. |
| 9,572,577 B2 | 2/2017 | Lloyd et al. |
| 9,585,657 B2 | 3/2017 | Shelton, IV et al. |
| 9,592,050 B2 | 3/2017 | Schmid et al. |
| 9,615,826 B2 | 4/2017 | Shelton, IV et al. |
| 9,649,190 B2 | 5/2017 | Mathies |
| 9,693,777 B2 | 7/2017 | Schellin et al. |
| 9,700,317 B2 | 7/2017 | Aronhalt et al. |
| 9,757,124 B2 | 9/2017 | Schellin et al. |
| 9,770,245 B2 | 9/2017 | Swayze et al. |
| 9,775,608 B2 | 10/2017 | Aronhalt et al. |
| 9,788,834 B2 | 10/2017 | Schmid et al. |
| 9,795,384 B2 | 10/2017 | Weaner et al. |
| 9,839,420 B2 | 12/2017 | Shelton, IV et al. |
| 9,839,422 B2 | 12/2017 | Schellin et al. |
| 9,839,423 B2 | 12/2017 | Vendely et al. |
| 9,848,875 B2 | 12/2017 | Aronhalt et al. |
| 9,861,361 B2 | 1/2018 | Aronhalt et al. |
| 9,884,456 B2 | 2/2018 | Schellin et al. |
| 10,123,798 B2 | 11/2018 | Baxter, III et al. |
| 10,136,890 B2 | 11/2018 | Shelton, IV et al. |
| 10,172,611 B2 | 1/2019 | Shelton, IV et al. |
| 10,172,617 B2 | 1/2019 | Shelton, IV et al. |
| 10,172,620 B2 | 1/2019 | Harris et al. |
| 10,213,198 B2 | 2/2019 | Aronhalt et al. |
| 10,271,849 B2 | 4/2019 | Vendely et al. |
| 10,285,699 B2 | 5/2019 | Vendely et al. |
| 10,299,878 B2 | 5/2019 | Shelton, IV et al. |
| 10,307,160 B2 | 6/2019 | Vendely et al. |
| 10,327,764 B2 | 6/2019 | Harris et al. |
| 10,327,777 B2 | 6/2019 | Harris et al. |
| 10,390,823 B2 | 8/2019 | Shelton, IV et al. |
| 10,405,854 B2 | 9/2019 | Schmid et al. |
| 10,433,846 B2 | 10/2019 | Vendely et al. |
| 10,478,188 B2 | 11/2019 | Harris et al. |
| 10,524,788 B2 | 1/2020 | Vendely et al. |
| 10,561,420 B2 | 2/2020 | Harris et al. |
| 10,569,071 B2 | 2/2020 | Harris et al. |
| 10,603,039 B2 | 3/2020 | Vendely et al. |
| 10,617,418 B2 | 4/2020 | Barton et al. |
| 10,736,633 B2 | 8/2020 | Vendely et al. |
| 10,835,249 B2 | 11/2020 | Schellin et al. |
| 10,932,779 B2 | 3/2021 | Vendely et al. |
| 10,980,539 B2 | 4/2021 | Harris et al. |
| 11,058,425 B2 | 7/2021 | Widenhouse et al. |
| 11,553,916 B2 | 1/2023 | Vendely et al. |
| 11,690,623 B2 | 7/2023 | Shelton, IV et al. |
| 11,712,244 B2 | 8/2023 | Vendely et al. |
| 11,944,308 B2 | 4/2024 | Vendely et al. |
| 2002/0127265 A1 | 9/2002 | Bowman et al. |
| 2002/0133236 A1* | 9/2002 | Rousseau ............ A61F 2/0063 623/23.72 |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2009/0090763 A1 | 4/2009 | Zemlok et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0233298 A1 | 9/2012 | Verbandt et al. |
| 2012/0248169 A1 | 10/2012 | Widenhouse et al. |
| 2013/0153641 A1 | 6/2013 | Shelton, IV et al. |
| 2013/0256373 A1 | 10/2013 | Schmid et al. |
| 2013/0256380 A1 | 10/2013 | Schmid et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0224857 A1 | 8/2014 | Schmid |
| 2014/0263552 A1 | 9/2014 | Hall et al. |
| 2014/0291379 A1 | 10/2014 | Schellin et al. |
| 2015/0134077 A1 | 5/2015 | Shelton, IV et al. |
| 2017/0086829 A1 | 3/2017 | Vendely et al. |

FOREIGN PATENT DOCUMENTS

| | | |
|---|---|---|
| WO | WO-2007015971 A2 | 2/2007 |
| WO | WO-2014004209 A2 | 1/2014 |
| WO | WO-2015138760 A1 | 9/2015 |

* cited by examiner

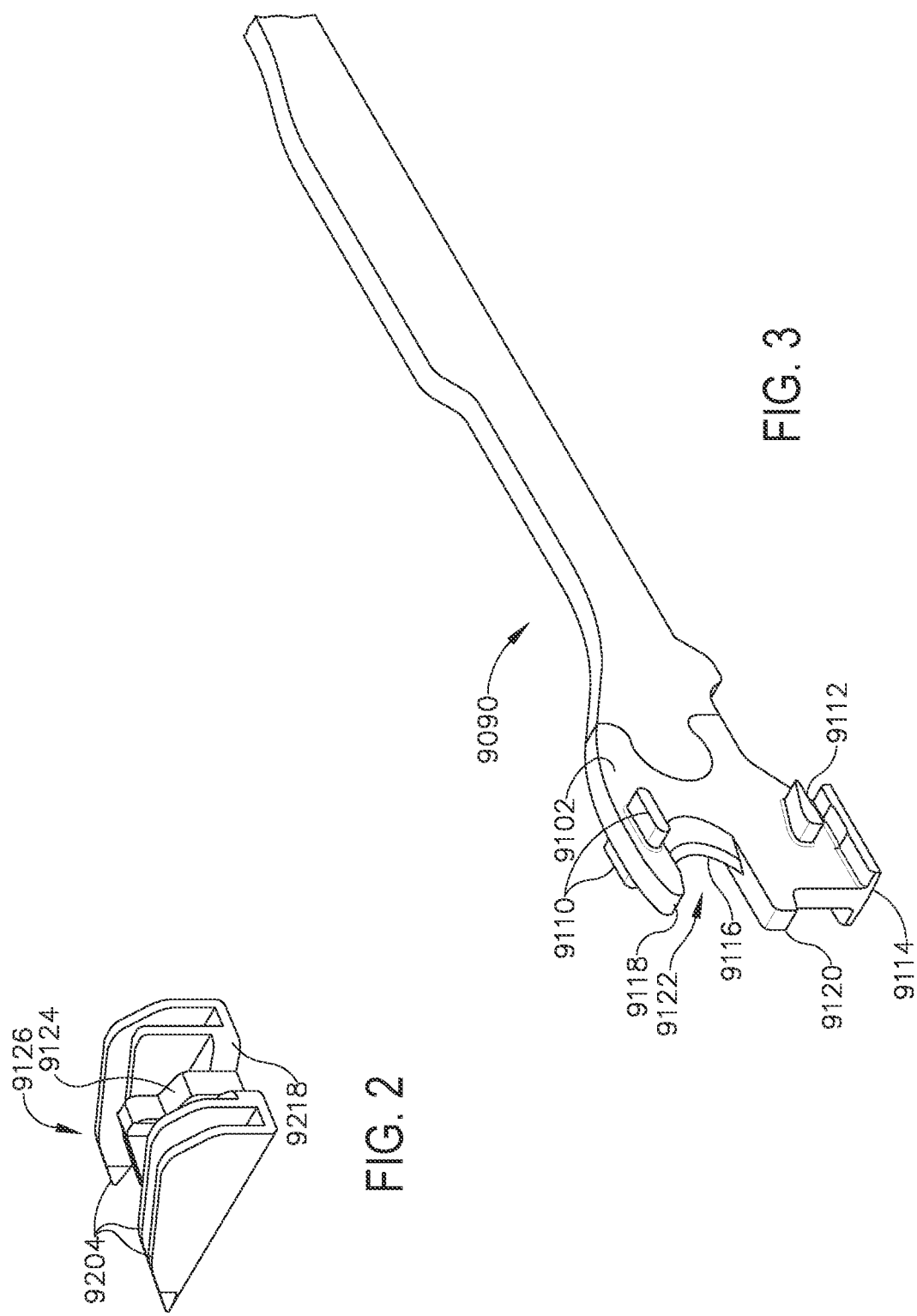

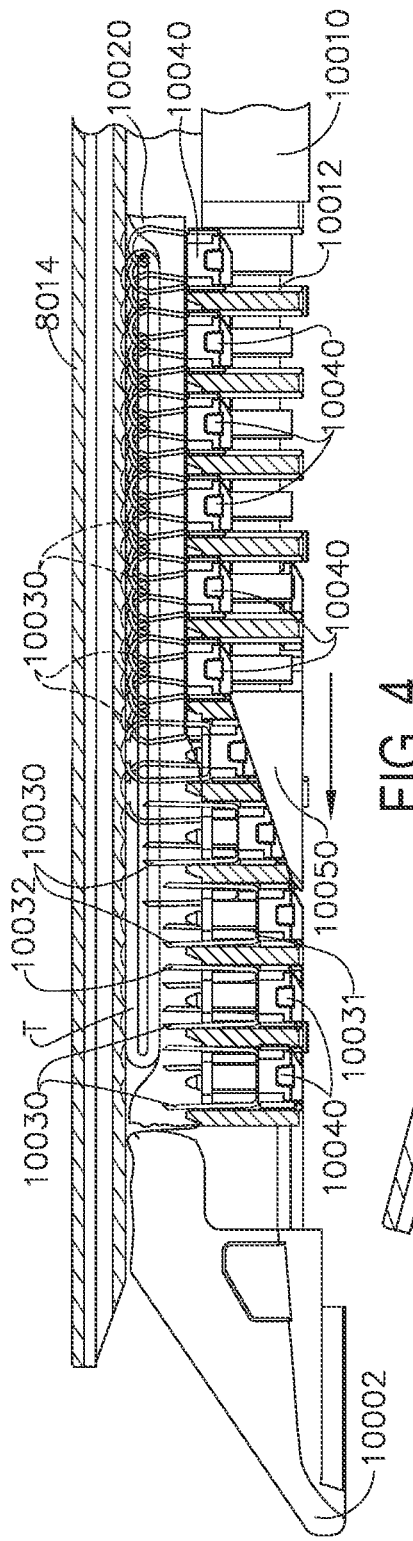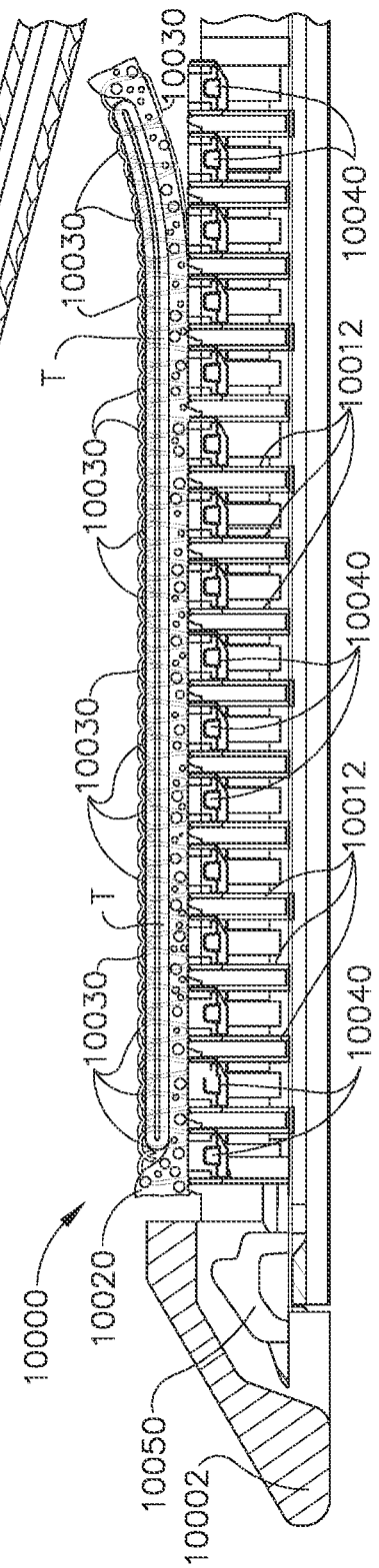
FIG. 4
FIG. 5

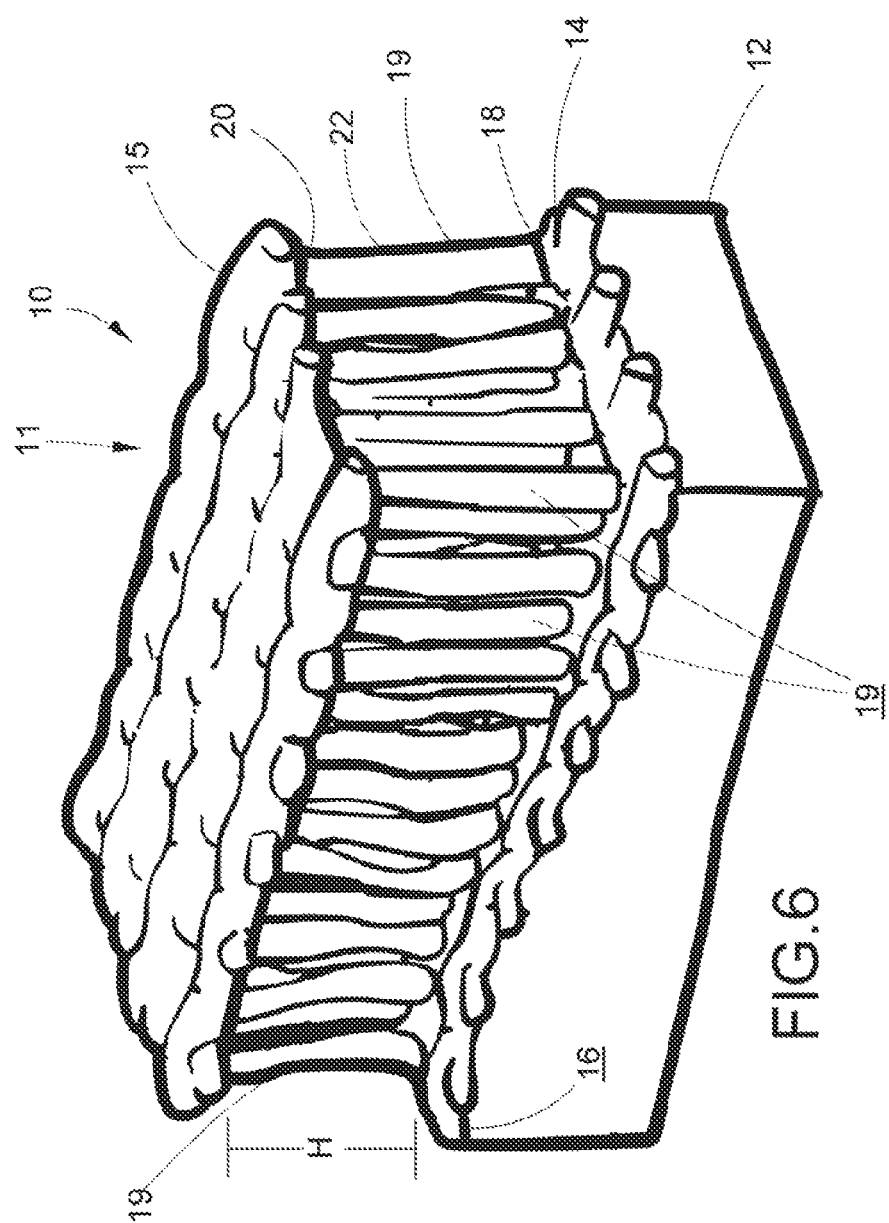

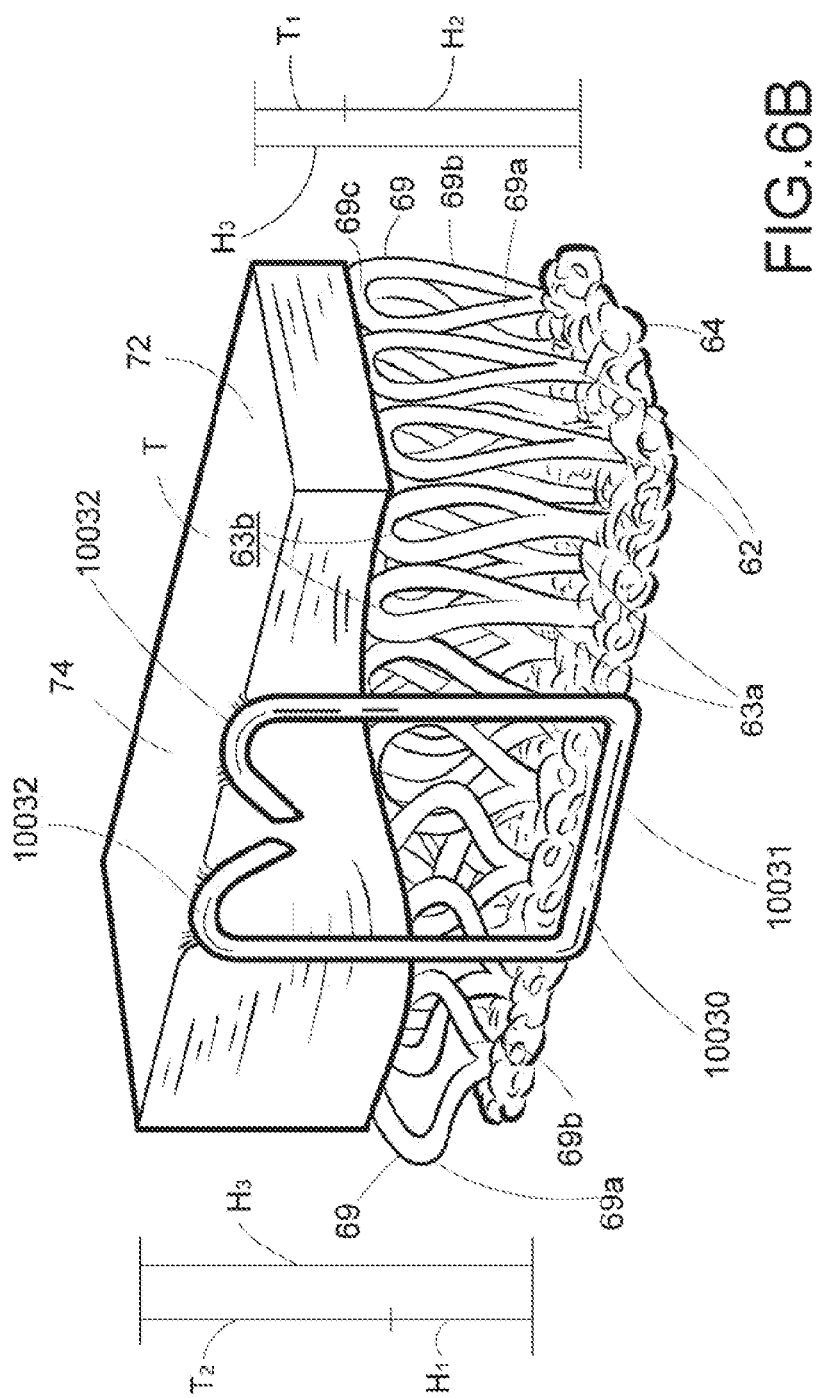

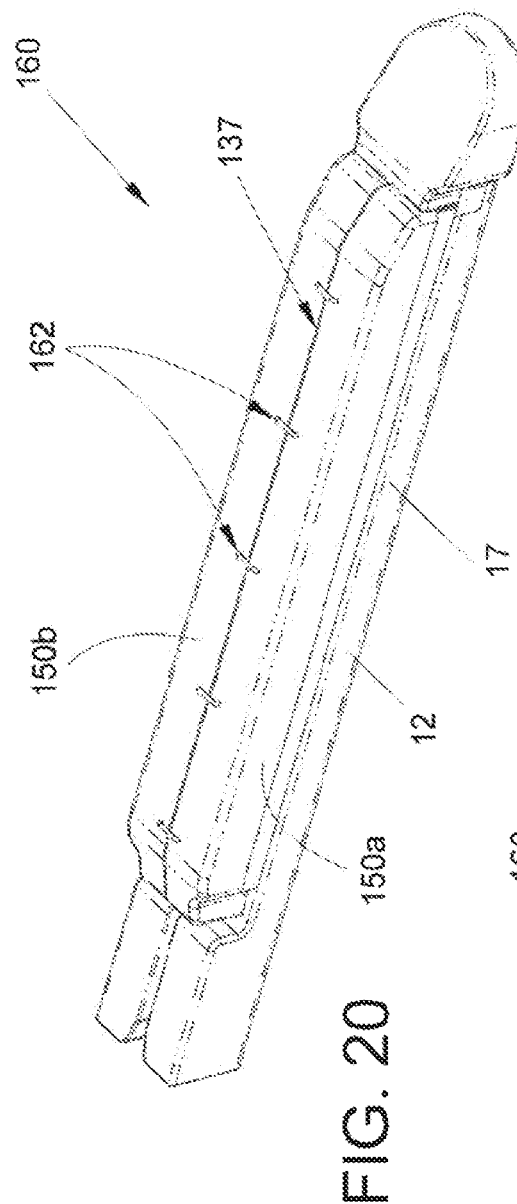
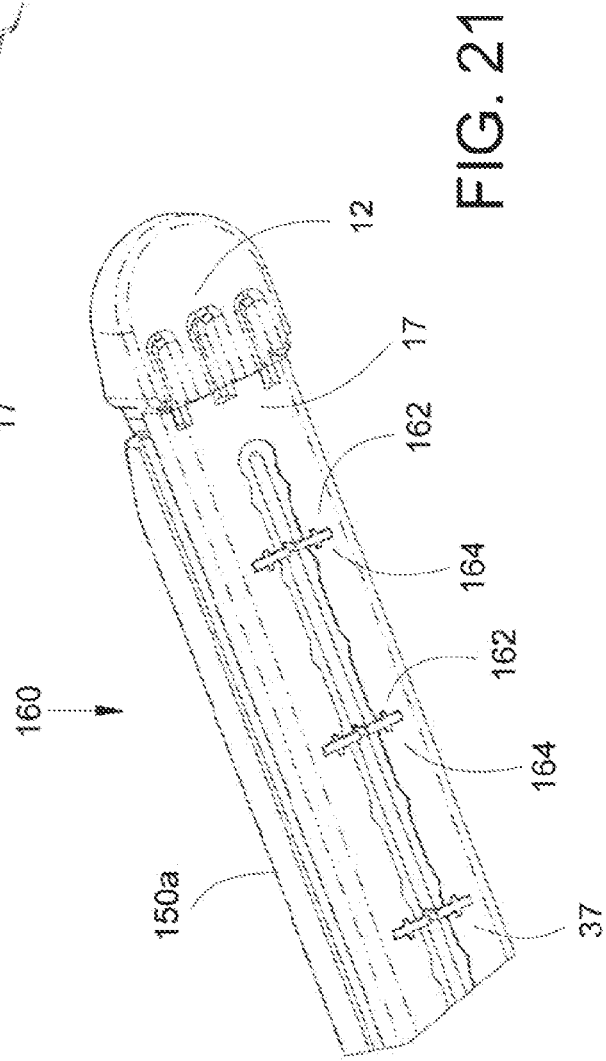

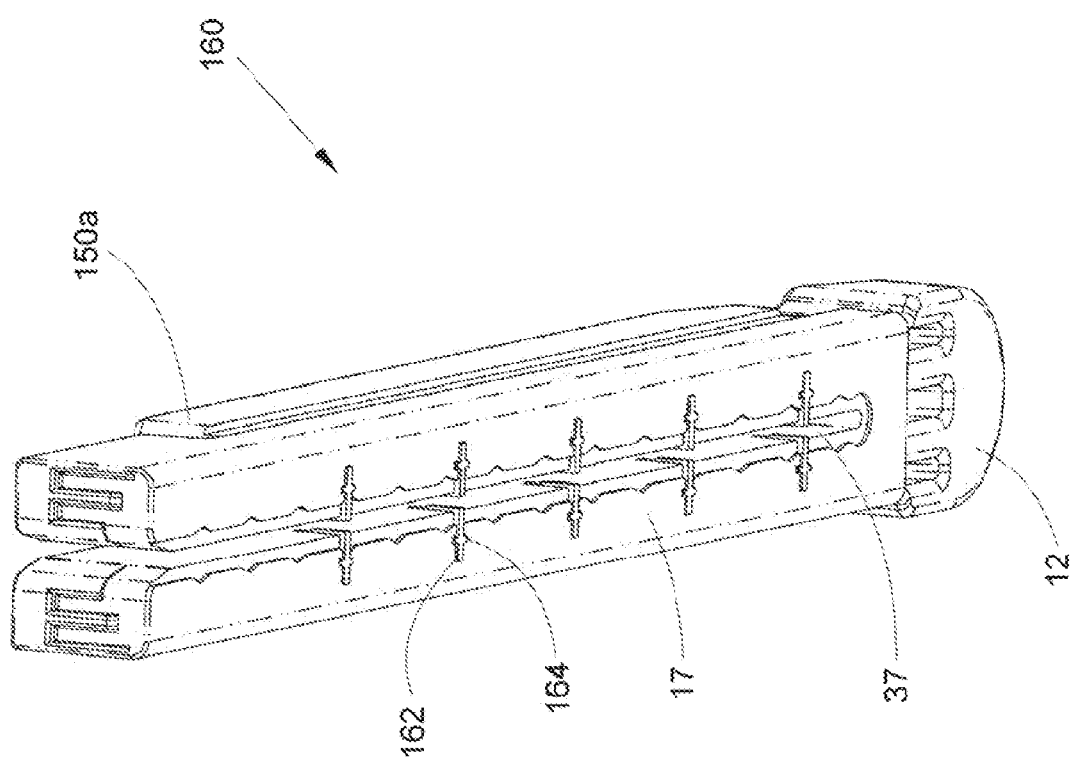

COMPRESSIBLE ADJUNCT WITH CROSSING SPACER FIBERS

CROSS-REFERENCE TO RELATED APPLICATIONS

This application is a continuation patent application claiming priority under 35 U.S.C. § 120 to U.S. patent application Ser. No. 18/081,335, entitled COMPRESSIBLE ADJUNCT WITH CROSSING SPACER FIBERS, filed Dec. 14, 2022, now U.S. Patent Application Publication No. 2023/0255631, which is a continuation patent application claiming priority under 35 U.S.C. § 120 to U.S. patent application Ser. No. 17/186,335, entitled COMPRESSIBLE ADJUNCT WITH CROSSING SPACER FIBERS, filed Feb. 26, 2021, which issued on Aug. 1, 2023 as U.S. Pat. No. 11,712,244, which is a continuation patent application claiming priority under 35 U.S.C. § 120 to U.S. patent application Ser. No. 16/229,607, entitled COMPRESSIBLE ADJUNCT WITH CROSSING SPACER FIBERS, filed Dec. 21, 2018, which issued on Mar. 2, 2021 as U.S. Pat. No. 10,932,779, which is a continuation patent application claiming priority under 35 U.S.C. § 120 to U.S. patent application Ser. No. 14/871,071, entitled COMPRESSIBLE ADJUNCT WITH CROSSING SPACER FIBERS, filed Sep. 30, 2015, which issued on Oct. 8, 2019 as U.S. Pat. No. 10,433,846, the entire disclosures of which are hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 2 is a perspective view of a wedge sled of a staple cartridge of the surgical stapling and severing instrument of FIG. 1;

FIG. 3 is a perspective view of a two-piece knife and firing bar ("E-beam") of the surgical stapling and severing instrument of FIG. 1;

FIG. 4 is a longitudinal cross-sectional view of an anvil in a closed position, a staple cartridge comprising a rigid support portion, and a compressible adjunct illustrated with staples being moved from an unfired position to a fired position during a firing sequence;

FIG. 5 is another cross-sectional view of the anvil and the staple cartridge of FIG. 4 illustrating the anvil in an open position after the firing sequence has been completed;

FIG. 6 is a partial perspective view of a staple cartridge assembly comprising a compressible adjunct in accordance with at least one embodiment;

FIG. 6B is a partial perspective view of an alternative compressible adjunct implanted against tissue by at least one staple in accordance with at least one embodiment;

FIG. 20 is a perspective view of a staple cartridge assembly comprising a compressible adjunct in accordance with at least one embodiment;

FIG. 21 is a different perspective view of the staple cartridge assembly of FIG. 20;

FIG. 22 is a different perspective view of the staple cartridge assembly of FIG. 20;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
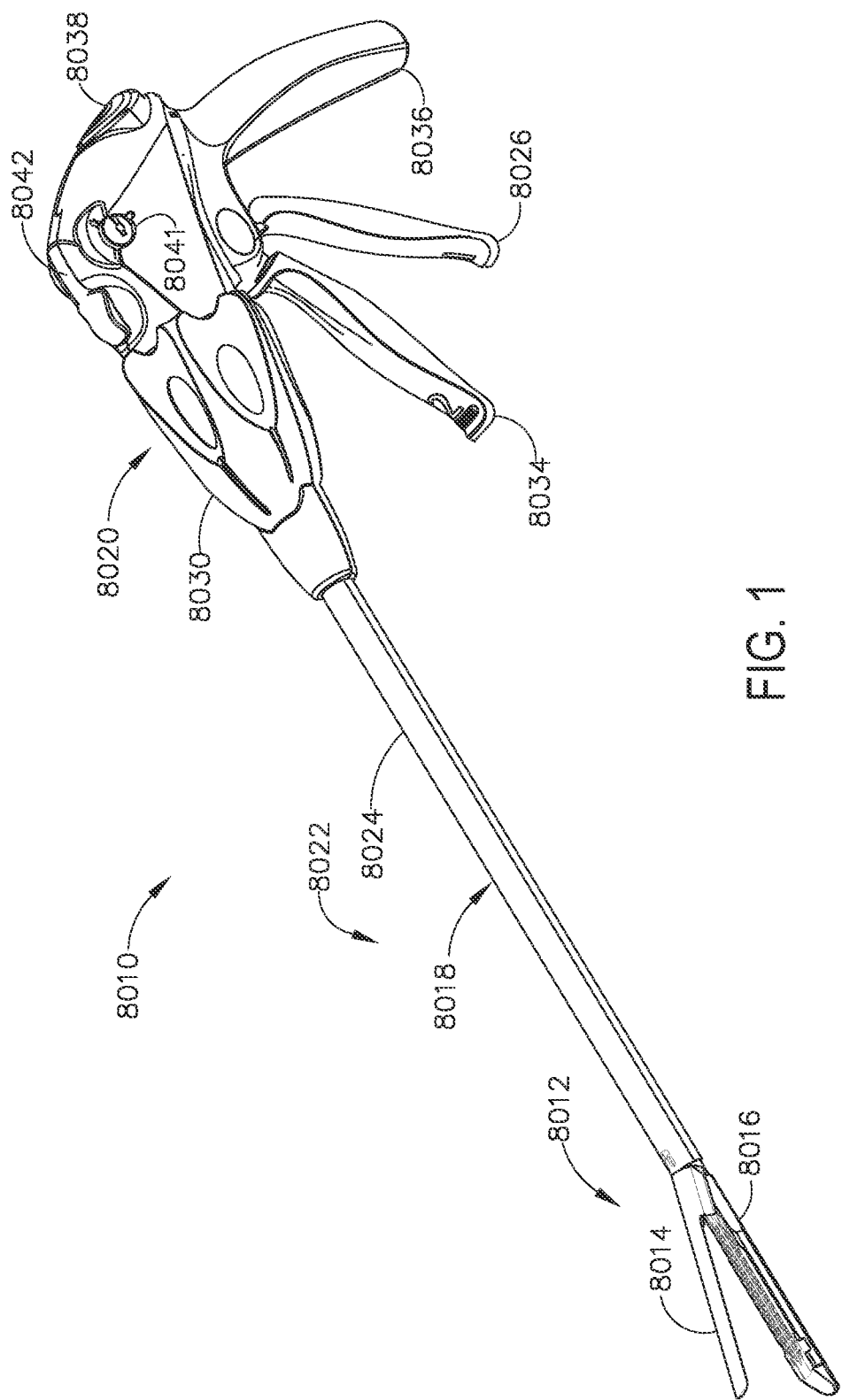
FIG. 1 is a perspective view of a surgical stapling and severing instrument comprising a handle, a shaft extending from the handle, and an end effector extending including an anvil and a staple cartridge.

The Applicant of the present application owns the following U.S. patent applications that were filed on Sep. 30, 2015 and which are each herein incorporated by reference in their respective entireties:

U.S. patent application Ser. No. 14/871,036, entitled IMPLANTABLE LAYER COMPRISING PLASTICALLY DEFORMED FIBERS, now U.S. Pat. No. 10,327,777;

U.S. patent application Ser. No. 14/871,056, entitled IMPLANTABLE LAYER COMPRISING A CONSTRICTED CONFIGURATION, now U.S. Pat. No. 10,478,188;

U.S. patent application Ser. No. 14/871,078, entitled TUBULAR ABSORBABLE CONSTRUCTS, now U.S. Pat. No. 10,561,420;

U.S. patent application Ser. No. 14/871,087, entitled IMPLANTABLE ADJUNCT COMPRISING BONDED LAYERS, now U.S. Patent Application Publication No. 2017/0086838;

U.S. patent application Ser. No. 14/871,107, entitled COMPRESSIBLE ADJUNCTS WITH BONDING NODES, now U.S. Pat. No. 10,172,620;

U.S. patent application Ser. No. 14/871,057, entitled COMPRESSIBLE ADJUNCT WITH INTERMEDIATE SUPPORTING STRUCTURES, now U.S. Patent Application Publication No. 2017/0086829;

U.S. patent application Ser. No. 14/871,083, entitled COMPRESSIBLE ADJUNCT WITH LOOPING MEMBERS, now U.S. Pat. No. 10,736,633;

U.S. patent application Ser. No. 14/871,089, entitled WOVEN CONSTRUCTS WITH INTERLOCKED STANDING FIBERS, now U.S. Pat. No. 10,271,849;

U.S. patent application Ser. No. 14/871,119, entitled COMPRESSIBLE ADJUNCT AND METHODS FOR MAKING THE SAME, now U.S. Pat. No. 10,285,699;

U.S. patent application Ser. No. 14/871,131, entitled METHOD FOR APPLYING AN IMPLANTABLE LAYER TO A FASTENER CARTRIDGE, now U.S. Patent Application Publication No. 2017/0086842;

U.S. patent application Ser. No. 14/871,153, entitled COMPRESSIBLE ADJUNCT WITH ATTACHMENT REGIONS, now U.S. Pat. No. 10,524,788;

U.S. patent application Ser. No. 14/871,176, entitled PROGRESSIVELY RELEASABLE IMPLANTABLE ADJUNCT FOR USE WITH A SURGICAL STAPLING INSTRUMENT, now U.S. Pat. No. 10,603,039; and U.S. patent application Ser. No. 14/871,195, entitled COMPRESSIBLE ADJUNCT ASSEMBLIES WITH ATTACHMENT LAYERS, now U.S. Pat. No. 10,307,160.

The Applicant of the present application also owns the U.S. patent applications identified below which are each herein incorporated by reference in their respective entireties:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Pat. No. 9,295,464;

U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Pat. No. 10,136,890;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084;

U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741;

U.S. patent application Ser. No. 13/241,629, entitled SURGICAL INSTRUMENT WITH SELECTIVELY ARTICULATABLE END EFFECTOR, now U.S. Patent Application Publication No. 2012/0074200;

U.S. patent application Ser. No. 13/433,096, entitled TISSUE THICKNESS COMPENSATOR COMPRISING A PLURALITY OF CAPSULES, now U.S. Pat. No. 9,301,752;

U.S. patent application Ser. No. 13/433,103, entitled TISSUE THICKNESS COMPENSATOR COMPRISING A PLURALITY OF LAYERS, now U.S. Pat. No. 9,433,419;

U.S. patent application Ser. No. 13/433,098, entitled EXPANDABLE TISSUE THICKNESS COMPENSATOR, now U.S. Pat. No. 9,301,753;

U.S. patent application Ser. No. 13/433,102, entitled TISSUE THICKNESS COMPENSATOR COMPRISING A RESERVOIR, now U.S. Pat. No. 9,232,941;

U.S. patent application Ser. No. 13/433,114, entitled RETAINER ASSEMBLY INCLUDING A TISSUE THICKNESS COMPENSATOR, now U.S. Pat. No. 9,386,988;

U.S. patent application Ser. No. 13/433,136, entitled TISSUE THICKNESS COMPENSATOR COMPRISING AT LEAST ONE MEDICAMENT, now U.S. Pat. No. 9,839,420;

U.S. patent application Ser. No. 13/433,141, entitled TISSUE THICKNESS COMPENSATOR COMPRISING CONTROLLED RELEASE AND EXPANSION, now U.S. Pat. No. 10,123,798;

U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;

U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. patent application Ser. No. 13/433,155, entitled TISSUE THICKNESS COMPENSATOR COMPRISING RESILIENT MEMBERS, now U.S. Pat. No. 9,480,476;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. patent application Ser. No. 13/763,028, entitled ADHESIVE FILM LAMINATE, now U.S. Pat. No. 9,282,962;

U.S. patent application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. patent application Ser. No. 13/433,118, entitled TISSUE THICKNESS COMPENSATOR COMPRISED OF A PLURALITY OF MATERIALS, now U.S. Pat. No. 9,414,838;

U.S. patent application Ser. No. 13/433,135, entitled MOVABLE MEMBER FOR USE WITH A TISSUE THICKNESS COMPENSATOR, now U.S. Pat. No. 9,517,063;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,129, entitled TISSUE THICKNESS COMPENSATOR COMPRISING A PLURALITY OF MEDICAMENTS, now U.S. Pat. No. 9,211,120;

U.S. patent application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. patent application Ser. No. 11/714,049, entitled SURGICAL STAPLING DEVICE WITH ANVIL HAVING STAPLE FORMING POCKETS OF VARYING DEPTHS, now U.S. Patent Application Publication No. 2007/0194082;

U.S. patent application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. patent application Ser. No. 11/711,975, entitled SURGICAL STAPLING DEVICE WITH STAPLE DRIVERS OF DIFFERENT HEIGHT, now U.S. Patent Application Publication No. 2007/0194079;

U.S. patent application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. patent application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. patent application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. patent application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891;

U.S. patent application Ser. No. 13/369,629, entitled ROBOTICALLY-CONTROLLED CABLE-BASED SURGICAL END EFFECTORS, now U.S. Pat. No. 8,800,838;

U.S. patent application Ser. No. 12/695,359, entitled SURGICAL STAPLING DEVICES FOR FORMING STAPLES WITH DIFFERENT FORMED HEIGHTS, now U.S. Pat. No. 8,464,923;

U.S. patent application Ser. No. 13/072,923, entitled STAPLE CARTRIDGES FOR FORMING STAPLES HAVING DIFFERING FORMED STAPLE HEIGHTS, now U.S. Pat. No. 8,567,656;

U.S. patent application Ser. No. 13/766,325, entitled LAYER OF MATERIAL FOR A SURGICAL END EFFECTOR, now U.S. Patent Application Publication No. 2013/0256380;

U.S. patent application Ser. No. 13/763,078, entitled ANVIL LAYER ATTACHED TO A PROXIMAL END OF AN END EFFECTOR, now U.S. Pat. No. 9,848,875;

U.S. patent application Ser. No. 13/763,094, entitled LAYER COMPRISING DEPLOYABLE ATTACHMENT MEMBERS, now U.S. Pat. No. 9,788,834;

U.S. patent application Ser. No. 13/763,106, entitled END EFFECTOR COMPRISING A DISTAL TISSUE ABUTMENT MEMBER, now U.S. Pat. No. 9,592,050;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/763,112, entitled SURGICAL STAPLING CARTRIDGE WITH LAYER RETENTION FEATURES, now U.S. Pat. No. 10,405,854;

U.S. patent application Ser. No. 13/763,035, entitled ACTUATOR FOR RELEASING A TISSUE THICKNESS COMPENSATOR FROM A FASTENER CARTRIDGE, now U.S. Pat. No. 10,213,198;

U.S. patent application Ser. No. 13/763,042, entitled RELEASABLE TISSUE THICKNESS COMPENSATOR AND FASTENER CARTRIDGE HAVING THE SAME, now U.S. Pat. No. 9,861,361;

U.S. patent application Ser. No. 13/763,048, entitled FASTENER CARTRIDGE COMPRISING A RELEASABLE TISSUE THICKNESS COMPENSATOR, now U.S. Pat. No. 9,700,317;

U.S. patent application Ser. No. 13/763,054, entitled FASTENER CARTRIDGE COMPRISING A CUTTING MEMBER FOR RELEASING A TISSUE THICKNESS COMPENSATOR, now U.S. Pat. No. 9,272,406;

U.S. patent application Ser. No. 13/763,065, entitled FASTENER CARTRIDGE COMPRISING A RELEASABLY ATTACHED TISSUE THICKNESS COMPENSATOR, now U.S. Pat. No. 9,566,061;

U.S. patent application Ser. No. 13/763,021, entitled STAPLE CARTRIDGE COMPRISING A RELEASABLE COVER, now U.S. Pat. No. 9,386,984;

U.S. patent application Ser. No. 13/763,078, entitled ANVIL LAYER ATTACHED TO A PROXIMAL END OF AN END EFFECTOR, now U.S. Pat. No. 9,848,875;

U.S. patent application Ser. No. 13/763,095, entitled LAYER ARRANGEMENTS FOR SURGICAL STAPLE CARTRIDGES, now U.S. Pat. No. 9,770,245;

U.S. patent application Ser. No. 13/763,147, entitled IMPLANTABLE ARRANGEMENTS FOR SURGICAL STAPLE CARTRIDGES, now U.S. Pat. No. 10,390,823;

U.S. patent application Ser. No. 13/763,192, entitled MULTIPLE THICKNESS IMPLANTABLE LAYERS FOR SURGICAL STAPLING DEVICES, now U.S. Pat. No. 9,615,826;

U.S. patent application Ser. No. 13/763,161, entitled RELEASABLE LAYER OF MATERIAL AND SURGICAL END EFFECTOR HAVING THE SAME, now U.S. Patent Application Publication No. 2013/0153641;

U.S. patent application Ser. No. 13/763,177, entitled ACTUATOR FOR RELEASING A LAYER OF MATERIAL FROM A SURGICAL END EFFECTOR, now U.S. Pat. No. 9,585,657;

U.S. patent application Ser. No. 13/763,037, entitled STAPLE CARTRIDGE COMPRISING A COMPRESSIBLE PORTION, now U.S. Patent Application Publication No. 2014/0224857;

U.S. patent application Ser. No. 13/433,126, entitled TISSUE THICKNESS COMPENSATOR COMPRISING TISSUE INGROWTH FEATURES, now U.S. Pat. No. 9,320,523;

U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373;

U.S. patent application Ser. No. 13/851,703, entitled FASTENER CARTRIDGE COMPRISING A TISSUE THICKNESS COMPENSATOR INCLUDING OPENINGS THEREIN, now U.S. Pat. No. 9,572,577;

U.S. patent application Ser. No. 13/851,676, entitled TISSUE THICKNESS COMPENSATOR COMPRISING A CUTTING MEMBER PATH, now U.S. Patent Application Publication No. 2014/0291379;

U.S. patent application Ser. No. 13/851,693, entitled FASTENER CARTRIDGE ASSEMBLIES, now U.S. Pat. No. 9,332,984;

U.S. patent application Ser. No. 13/851,684, entitled FASTENER CARTRIDGE COMPRISING A TISSUE THICKNESS COMPENSATOR AND A GAP SETTING ELEMENT, now U.S. Pat. No. 9,795,384;

U.S. patent application Ser. No. 14/187,387, entitled STAPLE CARTRIDGE INCLUDING A BARBED STAPLE, now U.S. Patent Application Publication No. 2014/0166724;

U.S. patent application Ser. No. 14/187,395, entitled STAPLE CARTRIDGE INCLUDING A BARBED STAPLE, now U.S. Patent Application Publication No. 2014/0166725;

U.S. patent application Ser. No. 14/187,400, entitled STAPLE CARTRIDGE INCLUDING A BARBED STAPLE, now U.S. Patent Application Publication No. 2014/0166726;

U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, now U.S. Pat. No. 9,839,422;

U.S. patent application Ser. No. 14/187,386, entitled IMPLANTABLE LAYERS AND METHODS FOR ALTERING ONE OR MORE PROPERTIES OF IMPLANTABLE LAYERS FOR USE WITH FASTENING INSTRUMENTS, now U.S. Pat. No. 9,884,456;

U.S. patent application Ser. No. 14/187,390, entitled IMPLANTABLE LAYERS AND METHODS FOR MODIFYING THE SHAPE OF THE IMPLANTABLE LAYERS FOR USE WITH A SURGICAL FASTENING INSTRUMENT, now U.S. Pat. No. 9,839,423;

U.S. patent application Ser. No. 14/187,389, entitled IMPLANTABLE LAYER ASSEMBLIES, now U.S. Pat. No. 9,757,124;

U.S. patent application Ser. No. 14/187,385, entitled IMPLANTABLE LAYERS COMPRISING A PRESSED REGION, now U.S. Pat. No. 9,693,777;

U.S. patent application Ser. No. 14/187,384, entitled FASTENING SYSTEM COMPRISING A FIRING MEMBER LOCKOUT, now U.S. Pat. No. 9,775,608;

U.S. patent application Ser. No. 14/827,856, entitled IMPLANTABLE LAYERS FOR A SURGICAL INSTRUMENT, now U.S. Pat. No. 10,835,249;

U.S. patent application Ser. No. 14/827,907, entitled IMPLANTABLE LAYERS FOR A SURGICAL INSTRUMENT, now U.S. Pat. No. 10,617,418;

U.S. patent application Ser. No. 14/827,932, entitled IMPLANTABLE LAYERS FOR A SURGICAL INSTRUMENT, now U.S. Patent Application Publication No. 2017/0049448;

U.S. patent application Ser. No. 14/667,874, entitled MALLEABLE BIOABSORBABLE POLYMER ADHESIVE FOR RELEASABLY ATTACHING A STAPLE BUTTRESS TO A SURGICAL STAPLER, now U.S. Pat. No. 10,172,617;

U.S. patent application Ser. No. 14/300,954, entitled ADJUNCT MATERIALS AND METHODS OF USING SAME IN SURGICAL METHODS FOR TISSUE SEALING, now U.S. Pat. No. 10,172,611;

U.S. patent application Ser. No. 14/840,613, entitled DRUG ELUTING ADJUNCTS AND METHODS OF USING DRUG ELUTING ADJUNCTS, now U.S. Patent Application Publication No. 2017/0055986;

U.S. patent application Ser. No. 14/498,145, entitled METHOD FOR CREATING A FLEXIBLE STAPLE LINE, now U.S. Patent Application Publication No. 2016/0089142; and U.S. patent application Ser. No. 14/865,306, entitled IMPLANTABLE ADJUNCT SYSTEMS FOR DETERMINING ADJUNCT SKEW, now U.S. Patent Application Publication No. 2017/0086936.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which an end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

The staple cartridge can also include an implantable layer. The implantable layer is configured to be captured within a staple along with tissue when the staple is deployed by the corresponding driver. The implantable layer can comprise a buttress, a tissue thickness compensator, and/or other adjunct material. A tissue thickness compensator is configured to compensate for variations in tissue properties, such as variations in the thickness of tissue, for example, along a staple line. A tissue thickness compensator can be compressible and resilient. In use, a tissue thickness compensator prevents or limits the over-compression of stapled tissue while facilitating adequate tissue compression within and between staples.

The implantable layer of a staple cartridge can be releasably secured to the body of the staple cartridge. For example, the implantable layer can be releasably secured to the deck of the staple cartridge with a releasable adhesive, at least one attachment tab, and/or other attachment features. Additionally or alternatively, an implantable layer can be releasably secured to the first jaw or the second jaw. An implantable layer can be positioned on the cartridge-side of an end effector and/or the anvil-side of the end effector, for example.

An implantable layer can be configured to promote tissue ingrowth. In various instances, it is desirable to promote the ingrowth of tissue into an implantable layer to promote the healing of the treated tissue (e.g. stapled and/or incised tissue) and/or to accelerate the patient's recovery. More specifically, the ingrowth of tissue into an implantable layer may reduce the incidence, extent, and/or duration of inflammation at the surgical site. Tissue ingrowth into and/or around the implantable layer may manage the spread of infections at the surgical site, for example. The ingrowth of blood vessels, especially white blood cells, for example, into and/or around the implantable layer may fight infections in and/or around the implantable layer and the adjacent tissue. Tissue ingrowth may also encourage the acceptance of foreign matter (e.g. the implantable layer and the staples) by the patient's body and may reduce the likelihood of the patient's body rejecting the foreign matter. Rejection of foreign matter may cause infection and/or inflammation at the surgical site.

Turning to the Drawings wherein like numerals denote like components throughout the several views, FIG. 1 illustrates an exemplary surgical stapling and severing instrument 8010 suitable for use with an implantable adjunct such as, for example, a tissue thickness compensator. The surgical stapling and severing instrument 8010 can comprise an anvil 8014 which may be repeatedly opened and closed about its pivotal attachment to an elongate staple channel 8016. A staple applying assembly 8012 may comprise the anvil 8014 and the channel 8016, wherein the assembly 8012 can be proximally attached to an elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar.

In various circumstances, the staple cartridge assembly 8012 is manipulated by a handle 8020 connected to the elongate shaft 8018. The handle 8020 can comprise user controls such as a rotation knob 8030 that rotates the elongate shaft 8018 and the staple applying assembly 8012 about a longitudinal axis of the shaft 8018 and a closure trigger 8026, which can pivot in front of a pistol grip 8036 to close the staple applying assembly 8012. A closure release button 8038 is outwardly presented on the handle 8020 when the closure trigger 8026 is clamped such that the release button 8038 can be depressed to unclamp the closure trigger 8026 and open the staple applying assembly 8012, for example.

A firing trigger 8034, which can pivot in front of the closure trigger 8026, causes the staple applying assembly 8012 to simultaneously sever and staple tissue clamped therein. In various circumstances, multiple firing strokes can be employed using the firing trigger 8034 to reduce the amount of force required to be applied by the surgeon's hand per stroke. In certain embodiments, the handle 8020 can comprise one or more rotatable indicator wheels such as, for example, rotatable indicator wheel 8041 which can indicate the firing progress. A manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails.

Additional details on the surgical stapling and severing instrument 8010 and other surgical stapling and severing instruments suitable for use with the present disclosure are described, for example, in U.S. patent application Ser. No. 13/851,693, entitled FASTENER CARTRIDGE ASSEMBLY, and filed on Mar. 27, 2013, now U.S. Pat. No. 9,332,984, the entire disclosure of which is incorporated herein by reference. Furthermore, powered surgical stapling and severing instruments can also be utilized with the present disclosure. See, for example, U.S. Patent Application Publication No. 2009/0090763, entitled POWERED SURGICAL STAPLING DEVICE, and filed on Aug. 8, 2008, the entire disclosure of which is incorporated herein by reference.

With reference to FIGS. 2 and 3, a firing assembly such as, for example, firing assembly 9090 can be utilized with the surgical stapling and severing instrument 8010 to advance a wedge sled 9126 which comprises a plurality of wedges 9204 configured to deploy staples from the staple applying assembly 8012 into tissue captured between the anvil 8014 and the elongate staple channel 8016. Furthermore, an E-beam 9102 at a distal portion of the firing assembly 9090 may fire the stales from the staple applying assembly 8012 as well as position the anvil 8014 relative to the elongate staple channel 8016 during firing. The E-beam 9102 includes a pair of top pins 9110, a pair of middle pins 9112 which may follow portion 9218 of the wedge sled 9126, and a bottom pin or foot 9114, as well as a sharp cutting edge 9116 which can be configured to sever the captured tissue as the firing assembly 9090 is advanced distally. In addition, integrally formed and proximally projecting top guide 9118 and middle guide 9120 bracketing each vertical end of the cutting edge 9116 may further define a tissue staging area 9122 assisting in guiding tissue to the sharp cutting edge 9116 prior to being severed. The middle guide 9120 may also serve to engage and fire the staple applying assembly 8012 by abutting a stepped central member 9124 of the wedge sled 9126 (FIG. 2) that effects staple formation by the staple applying assembly 8012.

In various circumstances, a staple cartridge can comprise means for compensating for the thickness of tissue captured within staples deployed from a staple cartridge. Referring to FIG. 4, a staple cartridge, such as staple cartridge 10000, for example, can be utilized with the surgical stapling and severing instrument 8010 and can include a rigid first portion, such as support portion 10010, for example, and a compressible second portion, such as tissue thickness compensator 10020, for example. The support portion 10010 can comprise a cartridge body and a plurality of staple cavities 10012. A staple 10030, for example, can be removably positioned in each staple cavity 10012. Referring primarily to FIGS. 4 and 5, each staple 10030 can comprise a base 10031 and one or more legs 10032 extending from the base 10031. Prior to the staples 10030 being deployed, the bases 10031 of the staples 10030 can be supported by staple drivers positioned within the support portion 10010 and, concurrently, the legs 10032 of the staples 10030 can be at least partially contained within the staple cavities 10012.

In various circumstances, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area in which the tissue T and the tissue thickness compensator 10020 can be captured. In various circumstances, the staple entrapment area can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In use, further to the above and referring primarily to FIG. 4, an anvil, such as anvil 8014 of the surgical stapling and severing instrument 8010, can be moved into a closed position opposite the staple cartridge 10000 by depressing the closure trigger 8026 to advance the E-beam 9102. The anvil 8014 can position tissue against the tissue thickness compensator 10020 and, in various circumstances, compress the tissue thickness compensator 10020 against the support portion 10010, for example. Once the anvil 8014 has been suitably positioned, the staples 10030 can be deployed, as also illustrated in FIG. 4.

In various circumstances, as mentioned above, a staple-firing sled 10050, which is similar in many respects to the sled 9126 (See FIG. 3), can be moved from a proximal end of the staple cartridge 10000 toward a distal end 10002, as illustrated in FIG. 5. As the firing assembly 9090 is advanced, the sled 10050 can contact the staple drivers 10040 and lift the staple drivers 10040 upwardly within the staple cavities 10012. In at least one example, the sled 10050 and the staple drivers 10040 can each comprise one or more ramps, or inclined surfaces, which can co-operate to move the staple drivers 10040 upwardly from their unfired positions. As the staple drivers 10040 are lifted upwardly within their respective staple cavities 10012, the staple drivers 10040 can lift the staples 10030 upwardly such that the staples 10030 can emerge from their staple cavities 10012. In various circumstances, the sled 10050 can move several staples upwardly at the same time as part of a firing sequence.

Referring to FIG. 5, the staple legs 10032 of the staples 10030 can extend into the compensator 10020 beyond the support portion 10010 when the staples 10030 are in their unfired positions. In various circumstances, the tips of the staple legs 10032, or any other portion of the staple legs 10032, may not protrude through a top tissue-contacting surface 10021 of the tissue thickness compensator 10020 when the staples 10030 are in their unfired positions. In certain circumstances, the tips of the staple legs 10032 can comprise sharp tips which can incise and penetrate the tissue thickness compensator 10020.

Referring to FIG. 6, a staple cartridge assembly 10 is illustrated. The staple cartridge assembly 10 includes a staple cartridge 12 which can be used with the surgical stapling and severing instrument 8010. The staple cartridge 12 is similar in many respects to the staple cartridge 10000. Like the staple cartridge 10000, the staple cartridge 12 includes a plurality of staples 10030 which are housed in a plurality of cavities or pockets defined in the staple cartridge 12. Also, the plurality of staples 10030 of the staple cartridge 12 can be deployed in a firing sequence of the surgical stapling and severing instrument 8010.

The staple cartridge 12 further includes a cartridge deck 16 and a knife slot 37 (FIGS. 14 and 16) that accommodates the cutting edge 9116 as it is advanced to cut tissue captured by the surgical stapling and severing instrument 8010. Advancement of the sled 10050 through the staple cartridge 12 causes the staples 10030 of staple cartridge 12 to be deployed from their respective pockets into tissue in the same, or substantially the same, manner that the staples 10030 are deployed from the staple cartridge 10000, as described above.

Referring again to FIG. 6, the staple cartridge assembly 10 further includes a tissue thickness compensator or compressible adjunct 11 which is similar in many respects to the tissue thickness compensator 10020. The compressible adjunct 11 is positioned against the cartridge deck 16. The compressible adjunct 11 is attached to the cartridge deck 16. For example, the compressible adjunct 11 can be partially melted onto the cartridge deck 16 then resolidified by cooling which causes the compressible adjunct 11 to bond to the cartridge deck 16. Various attachment features can also be employed to attach the compressible adjunct 11 to the cartridge deck 16.

The compressible adjunct 11 includes a first biocompatible layer 14 which is configured to be positioned against and/or attached to the cartridge deck 16 and, in addition, a second biocompatible layer 15 which is configured to be positioned against tissue captured between the anvil 8014 and the staple cartridge 12. The first biocompatible layer 14 and the second biocompatible layer 15 are spaced apart by a plurality of supporting members or pillars 19 extending or standing between the first biocompatible layer 14 and the second biocompatible layer 15, as illustrated in FIG. 6. The pillars 19 maintain an average distance between the first biocompatible layer 14 and the second biocompatible layer 15 defined in part by an average height (H) of the pillars 19.

As illustrated in FIG. 6, the pillars 19 have the same, or at least substantially the same, height (H). Alternatively, in certain instances, the pillars 19 may have different heights. Furthermore, as illustrated in FIG. 6, the pillars 19 have the same, or at least substantially the same, transverse cross-sectional area. Alternatively, the pillars 19 may have different transverse cross-sectional areas. In at least one instance, the transverse cross-sectional areas of a pillar 19 may vary along the height (H) of the pillar 19. For example, a pillar 19 may have a wide intermediate section and narrow end sections. Alternatively, a pillar 19 may have a narrow intermediate section and wide end sections. Alternatively, a pillar 19 may have a wide intermediate section, one wide end section, and one narrow end section. Alternatively, a pillar 19 may have a narrow intermediate section, one narrow end section, and one wide end section.

As illustrated in FIG. 6, the pillars 19 have circular, or at least substantially circular, transverse cross-sectional areas. Alternatively, one or more of the pillars 19 may have non-circular transverse cross-sectional areas. In at least one example, one or more of the pillars 19 may have an oval-shaped, a clover-shaped, a crescent-shaped, or a triangular-shaped transverse cross-sectional area. Other shapes of the transverse cross-sectional areas of the pillars 19 are contemplated by the present disclosure.

Generally, the material composition, the height, and/or the transverse cross-sectional area of a pillar 19 control, at least in part, its stiffness or ability to bend under compression which, in turn, controls, at least in part, the compressibility of the compressible adjunct 11. Accordingly, the pillars 19 can be configured to tune the compressibility of the compressible adjunct 11 to one or more desired values. Various sections of a compressible adjunct 11 may have pillars 19 with different stiffnesses or compressibilities, for example.

The pillars 19 are bendable under compression applied to the compressible adjunct 11 as an anvil 8014 is moved into a closed position opposite the staple cartridge 12. The resilience of the pillars 19 permits the compressible adjunct 11 to accommodate tissue (T) with tissue portions having different tissue thicknesses while maintaining the same, or at least substantially the same, average distance between the anvil 8014 and the staple cartridge 12 during a firing sequence of the surgical stapling and severing instrument 8010.

Figure 6A:
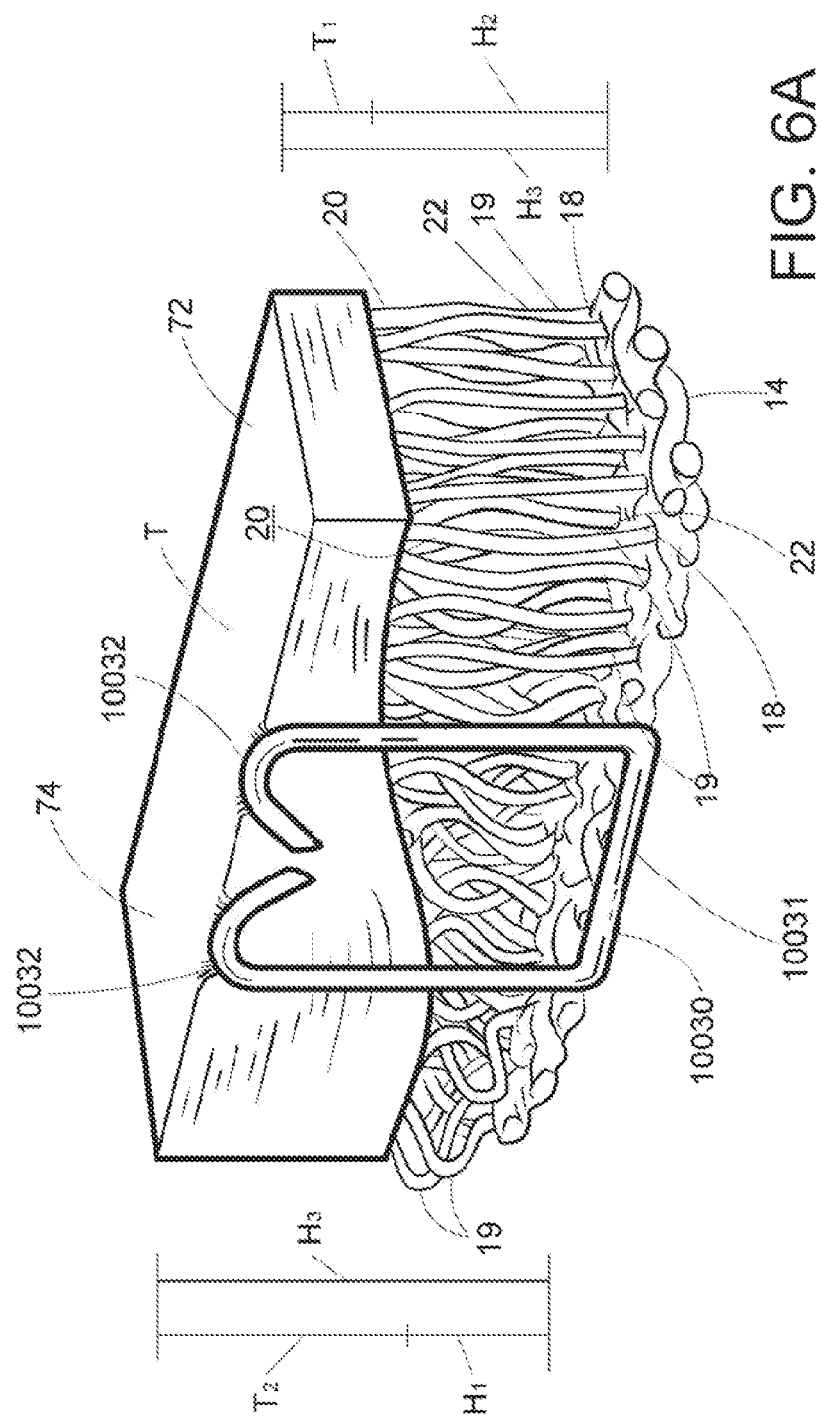
FIG. 6A is a partial perspective view of the adjunct of FIG. 6 implanted against tissue by at least one staple.

As illustrated in FIG. 6A, a staple 10030 is fired into a compressible adjunct 11 and tissue (T) comprising a first tissue portion 72 with an average tissue thickness (T1) and a second tissue portion 74 with an average tissue thickness (T2) greater than the tissue thickness (T1). The fired staple 10030 defines a space therein for accommodating the captured compressible adjunct 11 and the captured tissue (T). The space defined by the fired staple 10030 is limited, at least in part, by a height (H3) of the fired staple 10030, as illustrated in FIG. 6A. The sum of the final thickness of the captured tissue (T) and final height of the collapsed compressible adjunct 11 is equal, or at least substantially equal, to the height (H3) of the fired staple 10030. To compensate for the variability in the thickness of the captured tissue (T), the portion of the compressible adjunct 11 positioned against the second tissue portion (T2) is compressed to a final height (H2) which is greater than a final height (H1) of the portion of the compressible adjunct 11 positioned against the first tissue portion (T1). The resilience of the pillars 19 permits the compressible adjunct 11 to be compressed to a greater degree against the second tissue portion 74 than the first tissue portion 72, which permits the compressible adjunct 11 to compensate for the different thicknesses of the tissue portions 72 and 74 within the space defined by the fired staples 10030.

As the anvil 8014 is moved toward its closed position, the anvil 8014 can contact tissue T and apply a compressive force to the tissue T and the compressible adjunct 11. The material composition, porosity, frequency, size, and/or orientation of the pillars 19 can be tailored to control or tune the compressibility of the compressible adjunct 11.

In certain instances, the pillars 19 can be angled or slanted to favor an organized collapse in a first direction such as, for example, a proximal direction (P) in response to the compressive forces. In other instances, however, the pillars 19 can be angled or slanted to favor an organized collapse in a second direction different from the first direction such as, for example, a distal direction (D) in response to the compressive forces. In certain instances, a compressible adjunct 11 may include a first group of the pillars 19 that are angled or slanted to favor bending in a first direction and a second group of the pillars 19 that are angled or slanted to favor bending in a second direction different from the first direction. In such instances, the different bending directions may cause the compressible adjunct 11 to bend in a disorganized manner.

Referring to FIG. 6, the pillars 19 are oriented such that each pillar 19 extends, or at least substantially extends, along a transverse axis intersecting the first biocompatible layer 14 and the second biocompatible layer 15. The pillars 19 are perpendicular, or at least substantially perpendicular, to the first biocompatible layer 14 and the second biocompatible layer 15. Accordingly, the pillars 19 extend in parallel, or at least substantially in parallel, with one another. As illustrated in FIG. 6, the pillars 19 are spaced apart from one another and are arranged in parallel rows.

In certain instances, the pillars 19 are angled or oriented diagonally with respect to the first biocompatible layer 14 and/or the second biocompatible layer 15. In certain instances, the pillars 19 are organized in a predefined pattern such as, for example, in concentric circles. The frequency of the pillars 19 within a certain section of the compressible adjunct 11 can affect, among other things, the compressibility of such section. In certain instances, the pillars can be strategically concentrated in certain sections of the compressible adjunct 11 to provide greater column strength in such sections, for example. In at least one instance, the pillars 19 can be concentrated in sections of the compressible adjunct 11 that are configured to receive staples when the surgical stapling and severing instrument 8010 is fired. Alternatively, the pillars 19 can be concentrated in sections of the compressible adjunct 11 that do not receive staples when the surgical stapling and severing instrument 8010 is fired. In certain instances, the pillars 19 are arranged about an outer perimeter thereby defining side walls of the compressible adjunct 11, as illustrated in FIG. 6.

Each of the pillars 19 includes an intermediate standing portion 22 extending between a first end portion 18 secured to the first biocompatible layer 14 and a second end portion 20 secured to the second biocompatible layer 15. The end portions 18 and 20 can be embedded into the first biocompatible layer 14 and the second biocompatible layer 15, respectively. For example, the end portions 18 and 20 can be knitted or woven into the first biocompatible layer 14 and the second biocompatible layer 15, respectively. In certain instances, the end portions 18 and 20 can be welded onto the first biocompatible layer 14 and the second biocompatible layer 15, respectively, with heat or solvents. In certain instances, the end portions 18 and 20 can be glued, hooked, an/or fastened to the first biocompatible layer 14 and the second biocompatible layer 15, respectively, As illustrated in FIG. 6, The first biocompatible layer 14 and the second biocompatible layer 15 are woven layers. In certain instances, the first biocompatible layer 14 and/or the second biocompatible layer 15 can be knitted layers. In certain instances, the first biocompatible layer 14 and/or the second biocompatible layer 15 can be foam layers. In certain instances, the first biocompatible layer 14 and/or the second biocompatible layer 15 can be film layers.

Referring to FIG. 6B, a compressible adjunct 61 is stapled with a tissue (T). The compressible adjunct 61 includes a first biocompatible layer 64 which is configured to be positioned against and/or attached to a cartridge deck 16 of a staple cartridge 12. Looping members 69 protrude from the first biocompatible layer 64. The looping members 69 are directly positioned against the tissue captured between an anvil 8014 and the staple cartridge 12. Alternatively, the compressible adjunct 61 may include a second biocompatible layer is present, and the looping members 69 may maintain an average distance or separation between the biocompatible layers. In other words, the looping members 69 may lift or raise the second biocompatible layer over the first biocompatible layer 64.

The first biocompatible layer 64 and/or the second biocompatible layer can be woven layers. In certain instances, the first biocompatible layer 64 and/or the second biocompatible layer can be knitted layers. In certain instances, the first biocompatible layer 64 and/or the second biocompatible layer can be foam layers. In certain instances, the first biocompatible layer 64 and/or the second biocompatible layer can be film layers. One or more elongate flexible members such as, for example, monofilament and/or multifilament fibers can be used to form one or more looping members 69 by various techniques such as, for example, weaving and/or knitting. In at least one instance, an elongate flexible member can be threaded into the first biocompatible layer 64 to form a looping member 69, for example.

As illustrated in FIG. 6B, a looping member 69 includes a first end portion 69a, a second end portion 69b, and an intermediate curved portion 69c that extends between the first end portion 69a and the second end portion 69b. The end portions 69a and 69b are partially embedded and/or attached to the first biocompatible layer 64 while the intermediate curved portion 69c is lifted away or spaced apart from the first biocompatible layer 64 by the first end portion 69a and the second end portion 69b. The looping members 69 may have the same, or at least substantially the same, height. Alternatively, in certain instances, the looping members 69 may have different heights.

When the second biocompatible layer is present, the looping members 69 can be positioned between the first biocompatible layer 64 and the second biocompatible layer, and the intermediate curved portions 69c can be attached to the second biocompatible layer, for example. Various attachment techniques can be employed to secure the second biocompatible layer to the intermediate curved portions 69c such as, for example, using biocompatible glue. In certain instances, the intermediate curved portions 69c can be stitched with the second biocompatible layer.

As illustrated in FIG. 6B, the first biocompatible layer 64 comprises tethering islands 62 that are spaced apart from one another. The tethering islands 62 are arranged in parallel, or at least substantially parallel, rows. Each tethering island 62 is defined by a first end portion 69a and a second end portion 69b of a looping member 69 that intersect at that tethering island 62. In certain instances, the end portions 69a and 69b of a looping member 69 can be received by two tethering islands 62 that are spaced apart from one another, for example. In certain instances, only a single end portion 69a or 69b is received a tethering island 62, for example. Alternatively, a tethering island 62 can be configured to receive three or more of the end portions 69a and/or 69b, for example. A tethering island 62 can be configured to receive one or more of the end portions 69a but none of the end portions 69b, for example.

Further to the above, one or more of the looping members 69 includes a narrow neck portion 63a extending from a tethering island 62 and a wide head portion 63b extending from the narrow neck portion 63a. In certain instances, the head portions 63b can be positioned against the second biocompatible layer. Alternatively, the head portions 63b can be positioned against tissue (T).

As illustrated in FIG. 6B, the looping members 69 protrude from the first biocompatible layer 64 in a generally vertical direction, which causes the looping members 69 to bend in a disorganized manner in response to compressive forces transmitted through tissue (T) that is positioned against the compressible adjunct 61. In certain instances, the looping members 69 can be angled or slanted to favor an organized collapse in a first direction such as, for example, a proximal direction (P) in response to the compressive forces. In other instances, however, the looping members 69 can be angled or slanted to favor an organized collapse in a second direction different from the first direction such as, for example, a distal direction (D) in response to the compressive forces. In certain instances, a compressible adjunct 61 may include a first group of the looping members 69 that are angled or slanted to favor bending in a first direction, and a second group of the looping members 69 that are angled or slanted to favor bending in a second direction different from the first direction. In such instances, the different bending directions may cause the compressible adjunct 69 to bend in a disorganized manner.

Figure 7:
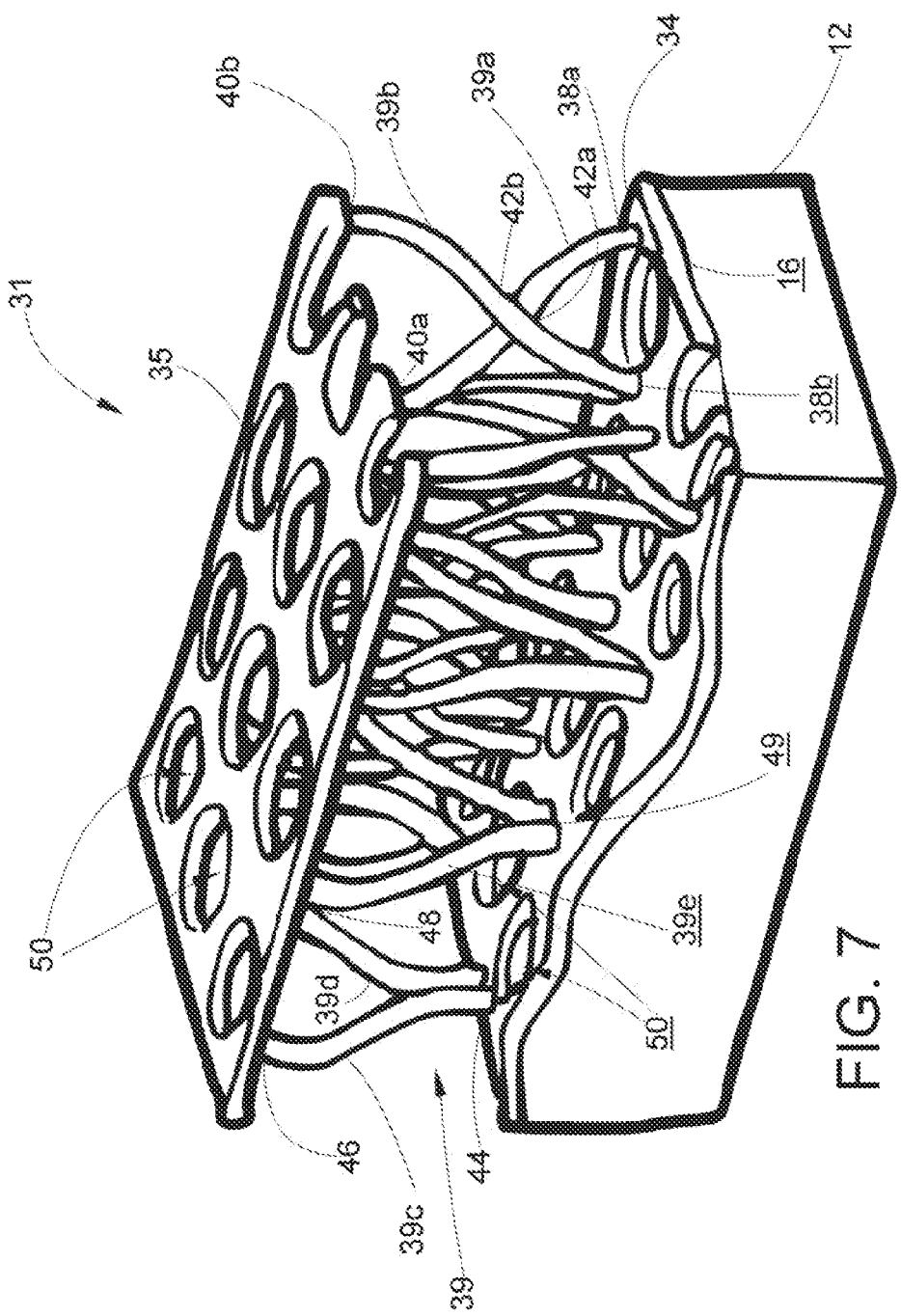
FIG. 7 is a partial perspective view of a staple cartridge assembly comprising an alternative compressible adjunct in accordance with at least one embodiment.

Referring to FIG. 7, a compressible adjunct 31 includes a first biocompatible layer 34 and a second biocompatible layer 35 that are perforated film layers, as described below in greater detail. The compressible adjunct 31 is similar in many respects to the compressible adjunct 11. For example, the compressible adjunct 31 comprises a plurality of pillars 39 which are similar in many respects to the pillars 19 of the compressible adjunct 11. Unlike the pillars 19, the pillars 39 are not arranged in parallel rows. The pillars 39 are configured to cross one another which can improve the stability of the compressible adjunct 31 by increasing resistance to collapsing under shear loads and/or compressive loads.

As illustrated in FIG. 7, a pillar 39a is configured to cross a pillar 39b. A first end portion 38a of the pillar 39a is aligned with a second end portion 40b of the pillar 39b such that a first transverse axis defined by the first end portion 38a and the second end portion 40b is perpendicular to the biocompatible layer 34 and a second biocompatible layer 35. Also, a first end portion 38b of the pillar 39b is aligned with a second end portion 40a of the pillar 39a such that a second transverse axis defined by the first end portion 38b and the second end portion 40a is perpendicular to the biocompatible layer 34 and a second biocompatible layer 35. Furthermore, intermediate portions 42a and 42b of the pillars 39a and 39b, respectively, can be attached to one another such as, for example, by welding. Alternatively, the intermediate portions 42a and 42b can be allowed to move freely relative to one another.

In a different arrangement, certain pillars 39 can be configured to share a bonding node or interface. As illustrated in FIG. 7, a pillar 39c and a pillar 39d are attached to the first biocompatible layer 34 at a bonding node 44. The pillars 39c and 39d extend from the bonding node 44 in different directions terminating at two different bonding nodes 46 and 48 on the second biocompatible layer 35. In addition, a pillar 39e extends from the bonding node 48 terminating at a bonding node 49 on the first biocompatible layer 34. Repetition of the arrangement of pillars 39c-39e between the biocompatible layers 34 and 35 can yield a zig-zag pattern therebetween. It should be understood that three or more pillars 39 may extend or emerge from one bonding node.

Further to the above, the perforated films of the biocompatible layers 34 and 35 can be produced by punching holes 50 in the films. The holes 50 may improve tissue ingrowth into the compressible adjunct 31. In certain instances, the holes 50 are created after the films are prepared. For example, a solvent or heat can be employed to remove sections of the films to create the holes 50. In other instances, the films can be prepared with the holes 50 using a mold, for example. As illustrated in FIG. 7, the holes 50 are arranged in rows. In addition, the holes 50 of the first biocompatible layer 34 are aligned with the holes 50 of the second biocompatible layer 35 to provide a path for the tissue growth through the compressible adjunct 31. Alternatively, the holes 50 can be randomly positioned. In at least one instance, the holes 50 are present in only one of the biocompatible layers 34 and 35.

Figure 8:
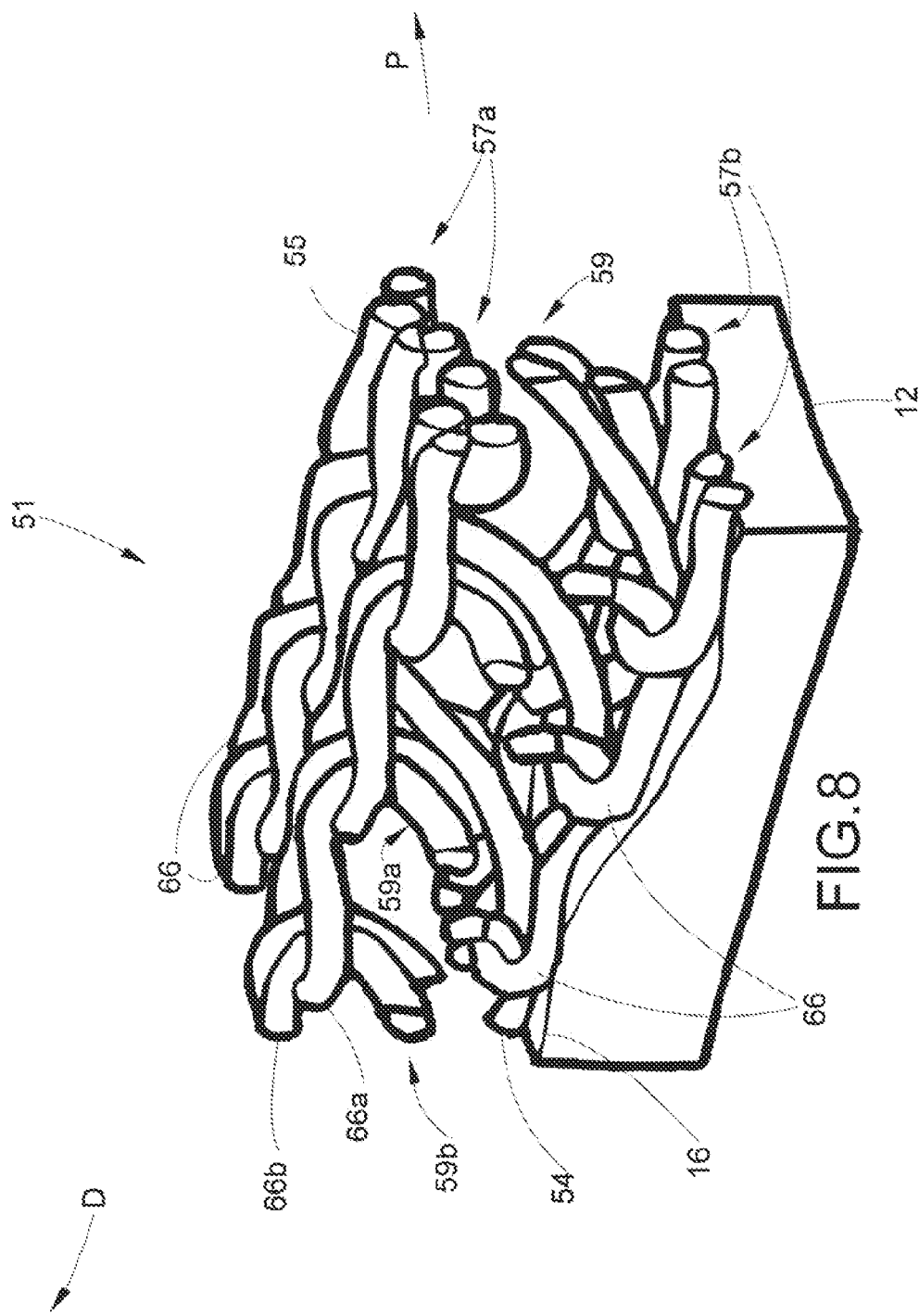
FIG. 8 is a partial perspective view of a staple cartridge assembly comprising an alternative compressible adjunct in accordance with at least one embodiment.

Referring to FIG. 8, a compressible adjunct 51 includes a first biocompatible layer 54 and a second biocompatible layer 55 that are spaced apart from one another by a plurality of support or standing pillars or fibers 59. The compressible adjunct 51 is similar in many respects to the compressible adjuncts 11 and 31. For example, the compressible adjunct 51 can be positioned against the cartridge deck 16 of the staple cartridge 12, as illustrated in FIG. 8. The compressible adjunct 51 comprises a weft knitted double fabric. In certain instances, the compressible adjunct 51 comprises two inter-looping sets of fibers that are configured to yield two tethered layers.

The compressible adjunct 51 includes a plurality of loops 66 running in parallel, or at least substantially in parallel, rows. Each loop 66 is positioned or starts at one of the biocompatible layers 54 and 55 and defines two standing fibers 59 that extend toward the other one of the biocompatible layers 54 and 55. The standing fibers 59 are angled or slanted to favor an organized collapse in a first direction such as, for example, a proximal direction (P) in response to compressive forces applied to the second biocompatible layer 55 through tissue (T) positioned against the second biocompatible layer 55. Alternatively, the standing fibers 59 can be angled or slanted to favor an organized collapse in a second direction opposite the first direction such as, for example, a distal direction (D) in response to the compressive forces. Alternatively, a compressible adjunct may include a first group of the standing fibers 59 that are angled or slanted to favor bending in the first direction and a second group of the standing fibers 59 that are angled or slanted to favor bending in the second direction. The different bending directions may cause the compressible adjunct 51 to bend in a disorganized manner.

As illustrated in FIG. 8, a first loop 66a originating in the second biocompatible layer 55 defines a first pair of standing fibers 59a extending from the second biocompatible layer 55 toward the first biocompatible layer 54. The first loop 66a holds a second pair of standing fibers 59b defined by a second loop 66b also originating in the second biocompatible layer 55. The second loop 66b is positioned at a distal location with respect to the first loop 66a. The second pair of standing fibers 59b also extends toward the first biocompatible layer 54. The described pattern is repeated at regular intervals. Likewise, similar loops 66 originating in the first biocompatible layer 54 define pairs of standing fibers 59 that extend from the first biocompatible layer 54 toward the second biocompatible layer 55.

The spacing between two consecutive pairs of standing fibers 59 can be increased or decreased to increase or decrease, respectively, the compressibility of the compressible adjunct 51. Generally, a greater number of standing fibers 59 at a certain section of the compressible adjunct 51 corresponds to a greater stability of that section of the compressible adjunct 51 under compressive forces.

The loops 66 of the first biocompatible layer 54 are arranged in parallel, or at least substantially parallel, rows 57a and the loops 66 of the second biocompatible layer 55 are arranged in parallel, or at least substantially parallel, rows 57b which are spaced apart from the rows 57a.

Figure 9:
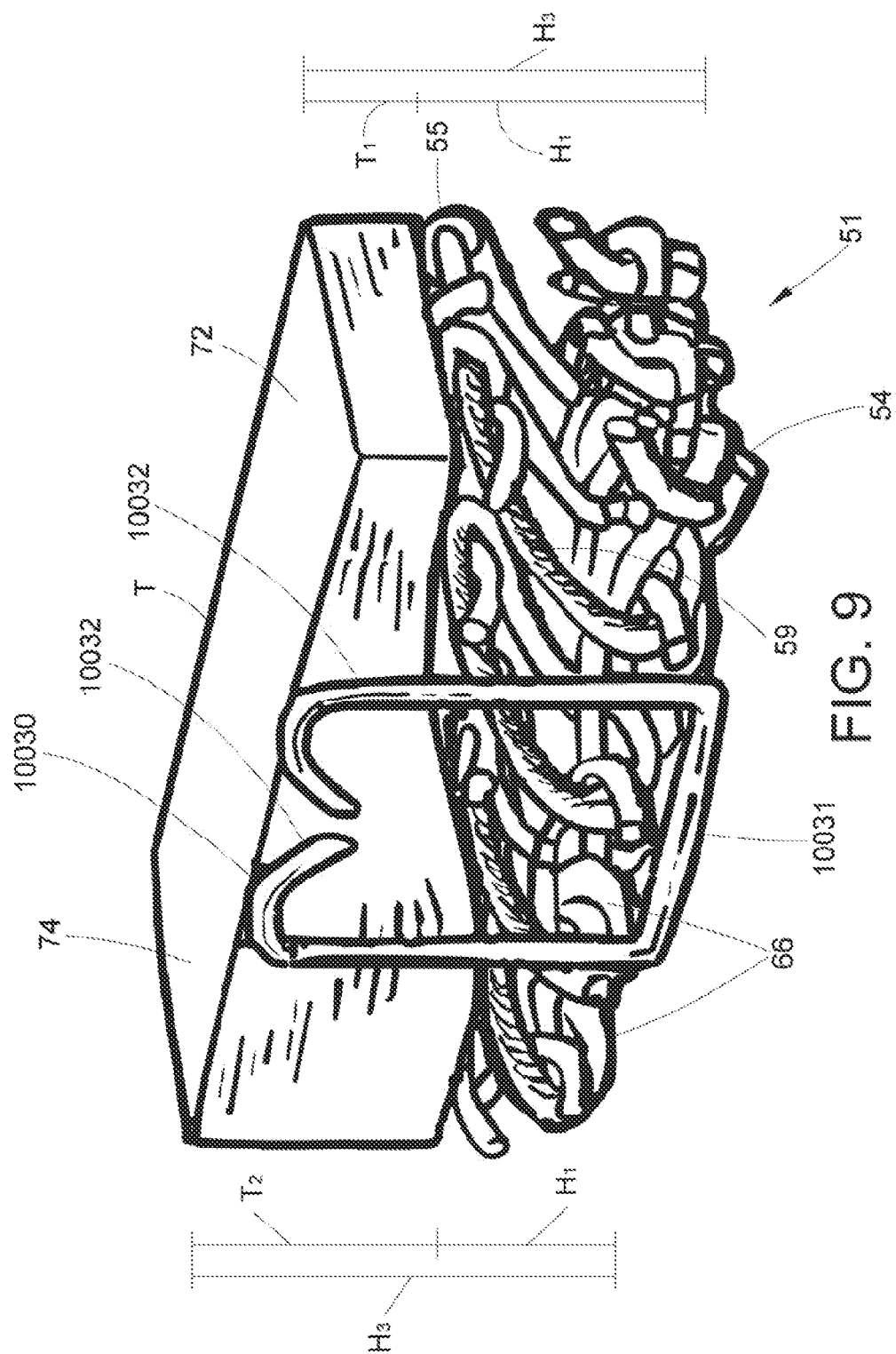
FIG. 9 is a partial perspective view of an alternative compressible adjunct implanted against tissue by at least one staple in accordance with at least one embodiment.

Referring to FIG. 9, a staple 10030 is fired into a compressible adjunct 51 and a tissue (T) comprising a first tissue portion 72 with an average tissue thickness (T1) and a second tissue portion 74 with an average tissue thickness (T2) greater than the tissue thickness (T1). The fired staple 10030 defines a space therein for accommodating the captured compressible adjunct 51 and the captured tissue (T). The space defined by the fired staple 10030 is limited, at least in part, by a height (H3) of the fired staple 10030, as illustrated in FIG. 9. The sum of the final thickness of the captured tissue (T) and final height of the collapsed compressible adjunct 51 is equal, or at least substantially equal, to the height (H3) of the fired staple 10030. To compensate for the variability in the thickness of the captured tissue (T), the portion of the compressible adjunct 51 positioned against the second tissue portion (T2) is compressed to a final height (H2) greater than a final height (H1) of the portion of the compressible adjunct 51 positioned against the first tissue portion (T1). The resilience of the standing fibers 59 permits the compressible adjunct 51 to be compressed to a greater degree against the second tissue portion 74 than the first tissue portion 72, which permits the compressible adjunct 51 to compensate for the different thicknesses of the tissue portions 72 and 74 within the space defined by the fired staples 10030. The material composition, porosity, frequency, size, and/or orientation of the standing fibers 59 can be tailored to control or tune the compressibility of the compressible adjunct 51.

Figure 10:
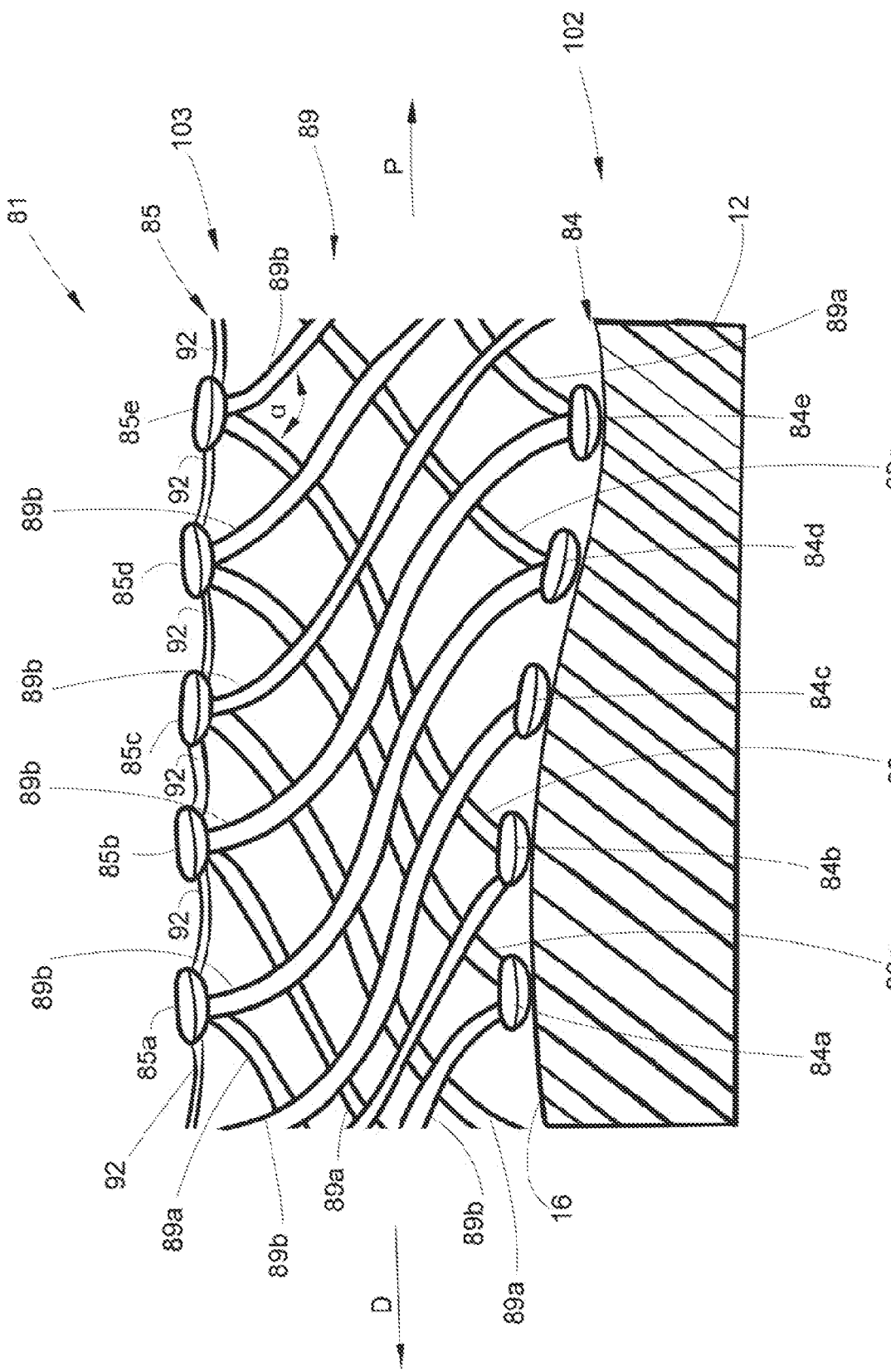
FIG. 10 is a partial cross-sectional view of a staple cartridge assembly comprising an alternative compressible adjunct in accordance with at least one embodiment.
Figure 11:
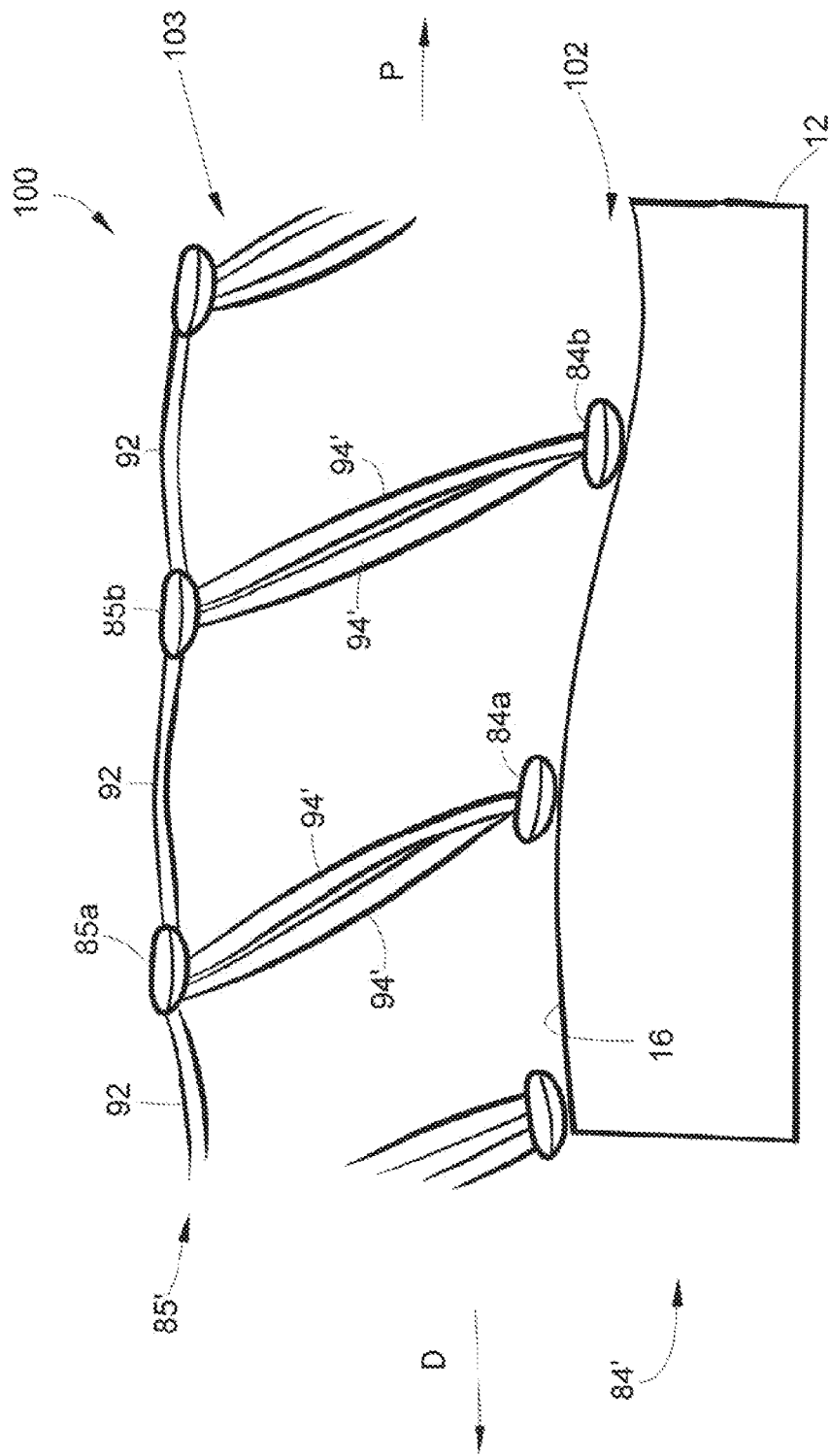
FIG. 11 is a partial cross-sectional view of a staple cartridge assembly comprising an alternative compressible adjunct in accordance with at least one embodiment.
Figure 12:
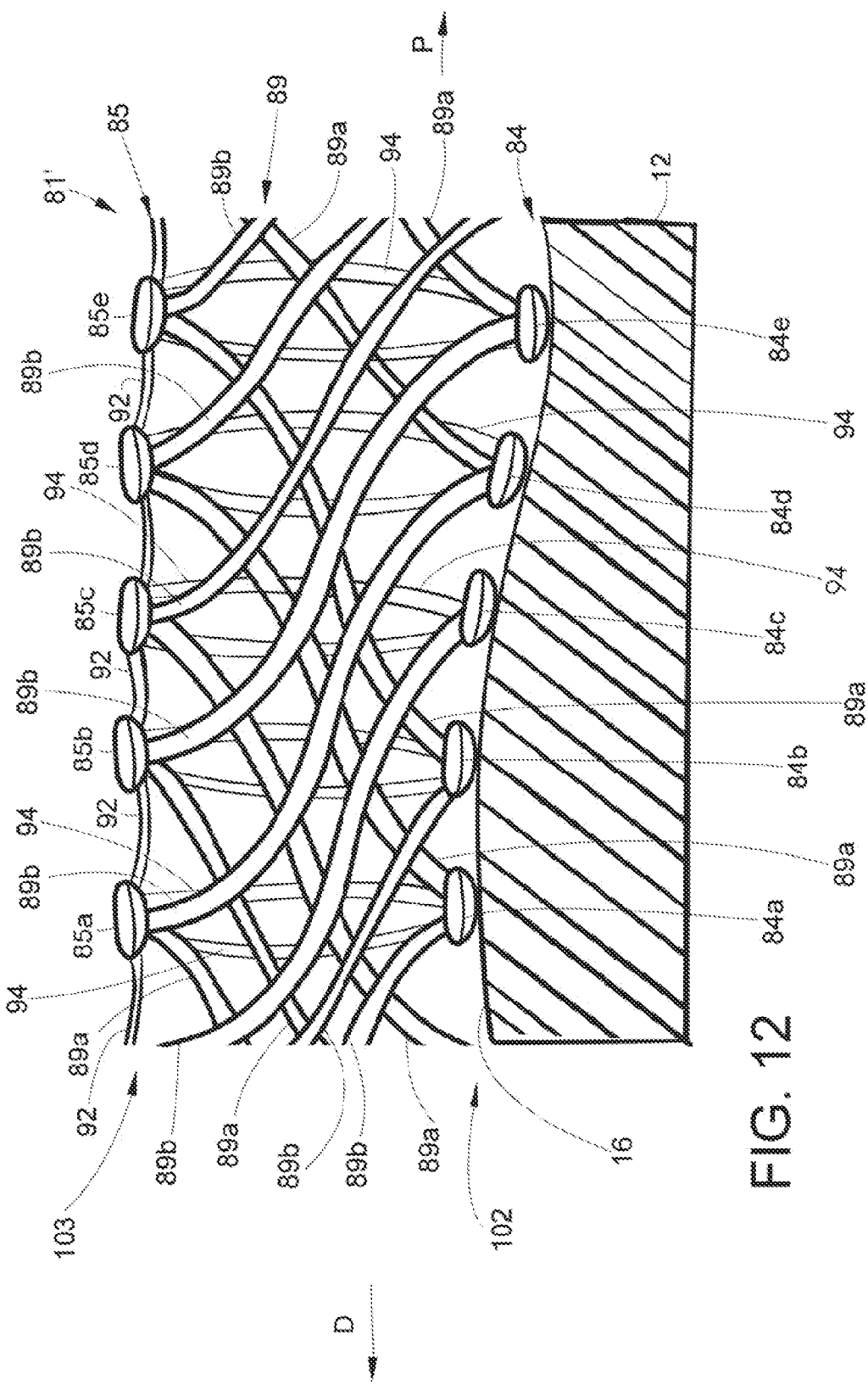
FIG. 12 is a partial cross-sectional view of a staple cartridge assembly comprising an alternative compressible adjunct in accordance with at least one embodiment.

Referring to FIGS. 10-12, various compressible adjuncts are positioned against the cartridge deck 16 of the staple cartridge 12. The compressible adjuncts of FIGS. 10-12 are similar in many respects to the compressible adjuncts 11, 31, and 51. The compressible adjuncts of FIGS. 10-12 are further characterized by bonding nodes or interfaces that are interconnected by one or more standing fibers. For example, as illustrated in FIG. 10, a compressible adjunct 81 includes a first series of bonding nodes 84a-84e defined in a first biocompatible layer 84 and a second series of bonding nodes 85a-85e defined in a second biocompatible layer 85 spaced apart from the first biocompatible layer 84. Spacer or standing fibers 89 extend from the first series of bonding nodes 84a-84e and/or the second series of bonding nodes 85a-85e.

The bonding nodes 84a-84e are vertically aligned, or at least substantially aligned, with corresponding bonding nodes 85*a*-85*e*. Moreover, the bonding nodes 84*a*-84*e* and the bonding nodes 85*a*-85*e* are arranged, or at least substantially arranged, in corresponding rows 102 and 103, respectively. Although only one row of bonding nodes is shown in each of the biocompatible layers 84 and 85, the biocompatible layer 84 and/or 85 may each include multiple rows of bonding nodes or interfaces.

As illustrated in FIG. 10, the standing fibers 89 may include a first group of standing fibers 89*a* and a second group of standing fibers 89*b* that are interlaced to form a mesh like structure. The standing fibers 89*a* generally follow parallel, or at least substantially parallel, paths that are angled or slanted in a proximal direction (P) with respect to a vertical axis. On the other hand, the standing fibers 89*b* generally follow parallel, or at least substantially parallel, paths that are angled or slanted in a distal direction (D) with respect to the vertical axis.

An angle α is defined between the fibers 89*a* and 89*b* extending from the a bonding node such as, for example, the bonding node 85*e*. The angle α is any angle in a range of about 100 to about 160°, for example. In certain instances, the angle α is any angle in a range of about 450 to about 135°, for example. In certain instances, the angle α is any angle in a range of about 60° to about 110°, for example.

As illustrated in FIG. 10, a standing fiber 89*b* extends in the proximal direction (P) from the bonding node 85*a* to the bonding node 84*d*. In other words, the standing fiber 89*b* connects a bonding node at a first position in the row 102 with a bonding node at a fourth position in the row 103. As a result, the standing fiber 89*b* crosses four of the standing fibers 89*a*. In certain instances, the standing fiber 89*b* can be attached to one or more of the four standing fibers 89*a* crossed by the standing fiber 89*b*.

Furthermore, a standing fiber 89*a* extends in the distal direction (D) from the bonding node 85*e* to the bonding node 84*b*. In other words, the standing fiber 89*a* connects a bonding node at a fifth position in the row 103 with a bonding node at a second position in the row 102. As a result, the standing fiber 89*a* crosses four of the standing fibers 89*b*. In certain instances, the standing fiber 89*a* can be attached to one or more of the four standing fibers 89*b* crossed by the standing fiber 89*a*. Crossing the standing fibers 89*a* and 89*b* improves the stability of the compressible adjunct 81 under compressive and/or shear forces.

In certain instances, a standing fiber may extend between a bonding node at a first position in a row of bonding nodes on a biocompatible layer and a bonding node at a second position in a row of bonding nodes on a different biocompatible layer. In certain instances, a standing fiber may extend between a bonding node at a first position in a row of bonding nodes on a biocompatible layer and a bonding node at a third position in a row of bonding nodes on a different biocompatible layer. In certain instances, a standing fiber may extend between a bonding node at a first position in a row of bonding nodes on a biocompatible layer and a bonding node at a fifth position in a row of bonding nodes on a different biocompatible layer. Various bonding nodes at various other positions can be connected by the standing fibers 89. In various instances, increasing the distances between the interconnected bonding nodes decreases stiffness of a compressible adjunct 81.

Referring to FIG. 12, the bonding nodes 81 of the biocompatible layer 85 are interconnected via bridging members 92 that extend between the bonding nodes of the biocompatible layer 85. As illustrated in FIG. 12, a bridging member 92 extends between the bonding nodes 85*a* and 85*b*. Another bridging member 92 extends between the bonding nodes 85*b* and 85*c*. Additional bridging member 92 may extend between various bonding nodes in the same row or different rows of the biocompatible layer 85.

In certain instances, the bonding nodes of at least one of the biocompatible layers 84 and 85 are interconnected via the bridging members 92. In certain instances, the bonding nodes of at least one of the biocompatible layers 84 and 85 are disconnected from one another. As illustrated in FIG. 10, the bonding nodes 84*a*-84*e* of the first biocompatible layer 84 are not directly connected to one another.

Referring to FIG. 12, a compressible adjunct 81' is depicted. The compressible adjunct 81' is similar in many respects to the compressible adjunct 81. In addition, each pair of vertically aligned bonding nodes of the biocompatible layers 84 and 85 is connected by a pair of standing fibers 94. For example, a pair of standing fibers 94 extends between the bonding node 85*a* and the bonding node 84*a*. The standing fibers 94 improve the stability of the compressible adjunct 81' under compressive and/or shear forces. In certain instances, only one standing fiber 94 extends between the vertically aligned bonding nodes of the biocompatible layers 84 and 85. In certain instances, three or more standing fibers 94 extend between the vertically aligned bonding nodes of the biocompatible layers 84 and 85.

Referring to FIG. 11, a compressible adjunct 100 is depicted. The compressible adjunct 100 is similar in many respects to the compressible adjuncts 81 and 81'. For example, the compressible adjunct 100 includes a first biocompatible layer 84', which includes bonding nodes 84*a* and 84*b*, and a second biocompatible layer 85', which includes connected bonding nodes 85*a* and 85*b*; however, the first biocompatible layer 84' is offset with the second biocompatible layer 85' such that the bonding nodes 84*a* and 84*b* of the first biocompatible layer 84' are not vertically aligned with the bonding nodes 85*a* and 85*b* of the second biocompatible layer 85'. In an alternative embodiment, however, bonding nodes of the first biocompatible layer 84' and corresponding bonding nodes of the second biocompatible layer 85' can be vertically aligned.

As illustrated in FIG. 11, the offset between the first biocompatible layer 84' and the second biocompatible layer 85' causes standing fibers 94', which extend between the bonding nodes 84*a* and 84*b* and the bonding nodes 85*a* 85*b*, to be angled or slanted to favor bending in a predetermined direction. For example, in the embodiment illustrated in FIG. 11, the first biocompatible layer 84' lags behind the second biocompatible layer 85' which causes the bonding node 85*a*, for example, to be ahead of the bonding node 84*a*. In result, the standing fibers 94' extending between the bonding nodes 85*a* and 84*a* favor bending in a distal direction (D). The standing fibers 94' extending between the bonding nodes 84*b* and 85*b* are also slanted or angled to favor bending in the distal direction (D). In an alternative embodiment, the standing fibers 94' can be oriented to favor bending in a proximal direction (P). The pattern is repeated such that the pairs of standing fibers are parallel, or at least substantially, parallel to one another. In at least one embodiment, one or more of the standing fibers 94' is oriented to favor bending the proximal direction (P) and one or more of the standing fibers 94' is oriented to favor bending in the distal direction (D). The bending direction of the standing fiber 94' can be chosen based, in part, on the type, position, and orientation of the treated tissue (T).

Referring again to FIGS. 10 and 12, the outer surfaces of the biocompatible layers 84 and 85 can be tailored to accommodate various staple cartridge decks and tissue surfaces. For example, as illustrated in FIGS. 10-12, the bonding nodes or interfaces of the biocompatible layer 84 are not directly connected to one another, which allows the biocompatible layer 84 additional flexibility to accommodate a stepped cartridge deck, for example. In certain instances, the standing fibers of a compressible adjunct may extend beyond a biocompatible layer to modify an outer surface of the biocompatible layer.

Figure 13:
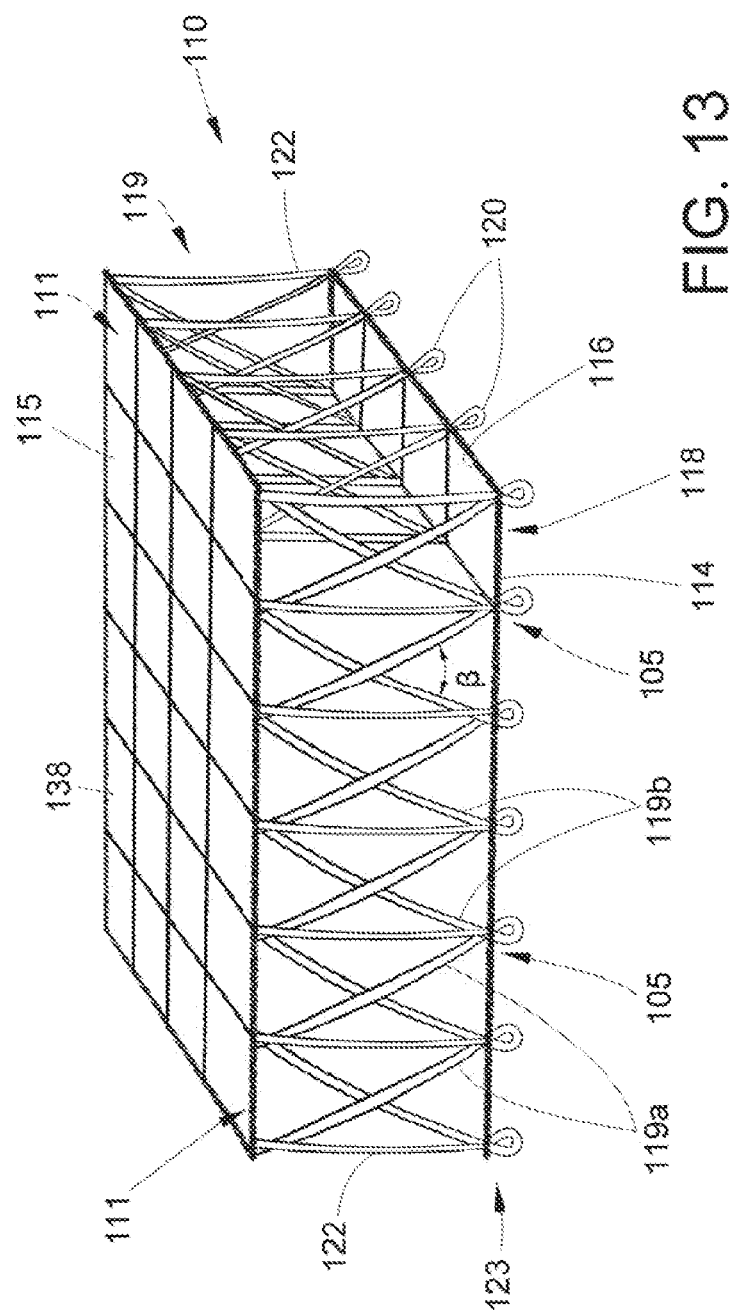
FIG. 13 is a partial perspective view of an alternative compressible adjunct in accordance with at least one embodiment.
Figure 14:
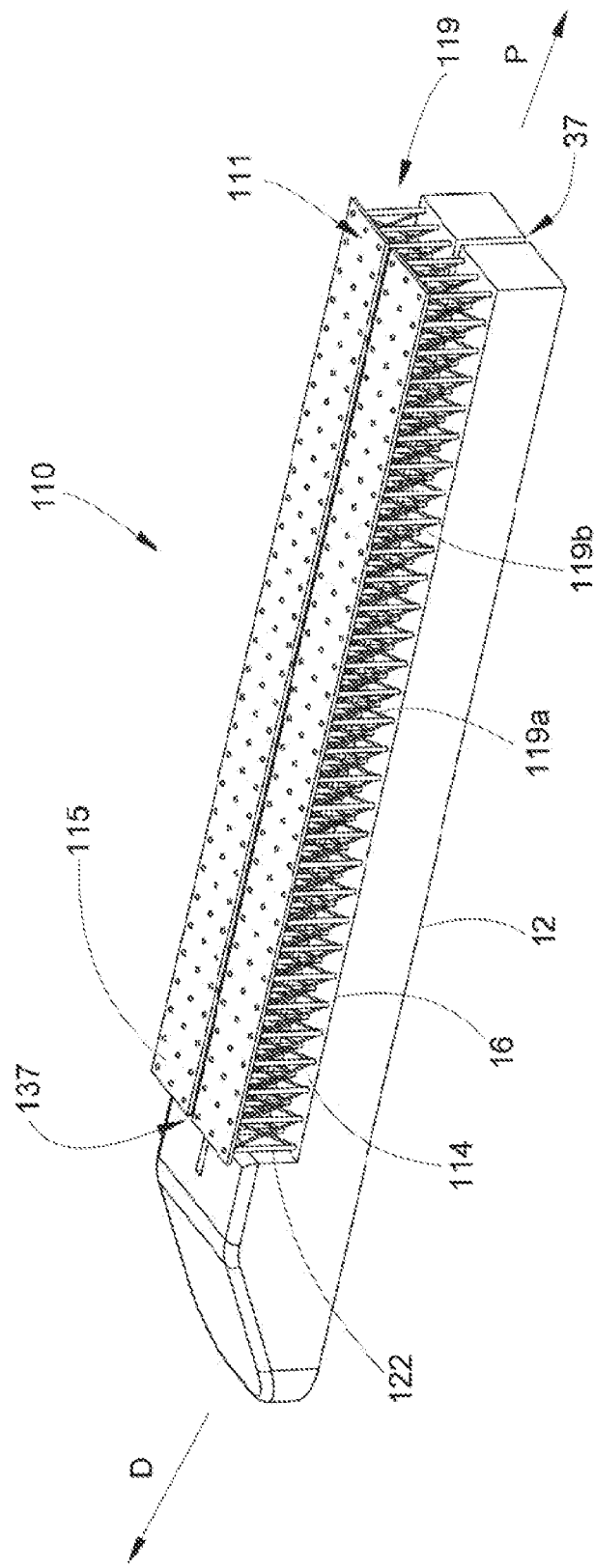
FIG. 14 is a perspective view of the compressible adjunct of FIG. 13 positioned against a cartridge deck of a staple cartridge.

Referring to FIGS. 13 and 14, a compressible adjunct 110 is similar in many respects to the compressible adjuncts 11, 31, 51, 81, 81', and 100. For example, the compressible adjunct 110 can be positioned against the cartridge deck 16 of the staple cartridge 12. Also, the compressible adjunct 110 includes a first biocompatible layer 114, a second biocompatible layer 115, and spacer or standing fibers 119 that are similar in many respects to the compressible layer 84, the compressible layer 85, and the standing fibers 89, respectively.

The standing fibers 119 are configured to provide structural support for the compressible adjunct 110. Adjacent fiber portions 119a and 119b are configured to cross one another, as illustrated in FIG. 13, to increase the stability of the compressible adjunct 110. Applying Compressive forces to the compressible adjunct 110 may cause the fiber portions 119a and 119b to bend and/or shift relative to one another.

As illustrated in FIG. 13-16, the compressible adjuncts 110 and 130 include building blocks 111 that are positioned at an outer perimeter of the compressible adjunct 110 and/or, in certain instances, at various other central positions. A building block 111 of the compressible adjunct 110 includes a pair of fiber portions 119a that is configured to cross a pair of fiber portions 119b at a plane defined at an intermediate distance between the compressible layers 114 and 115. In addition, four fiber portions 122 define four corners of the building block 111. Each of the four fiber portions 122 extends, or at least substantially extends, along a vertical axis transecting the biocompatible layers 114 and 115. In certain instances, the building blocks 111 do not include vertical fiber portions. Adjacent building blocks 111 share common fiber portions 122.

As illustrated in FIG. 13, Crossing fiber portions 119a and 119b define an angle β which can be any angle in a range of about 100 to about 170°, for example. In certain instances, the angle β can be any angle in a range of about 30° to about 100°, for example. In certain instances, the angle β can be any angle in a range of about 50° to about 70°, for example.

The standing fibers 119 of the compressible adjunct 110 further define gripping features that protrude from the first biocompatible layer 114. The gripping features can be in the form of traction loops 120. As illustrated in FIG. 13, two fiber portions 119a and 119b intersect at a bonding node or interface 105 at an inner surface 116 of the first biocompatible layer 114, and then extend through the first biocompatible layer 114 to form a loop 120 onto an outer surface 118 of the first biocompatible layer 114. A fiber 119 can be passed through the first biocompatible layer 114 to form several loops 120. Alternatively, the loops 120 can be formed onto the outer surface 118 independently of the fiber 119. For example, another fiber can be employed to form the loops 120 onto the first biocompatible layer 114. As illustrated in FIG. 13, the loops 120 are aligned with the bonding nodes or interfaces 105. Alternatively, in certain instances, the loops 120 are not aligned with the bonding nodes 105.

As illustrated in FIG. 13, the loops 120 are spaced apart and arranged in rows 123. The loops 120 can be positioned at an outer perimeter of the biocompatible layer 114 and/or, in certain instances, at various other positions on the first biocompatible layer 114 to provide traction against a cartridge deck 16 of a staple cartridge 12.

The frequency, position, arrangement, and/or size of the loops 120 at a particular section of the first biocompatible layer 114 can be controlled to achieve a desired degree of traction against the cartridge deck 16 at that section of the first biocompatible layer 114. For example, if additional traction against the cartridge deck 16 is desired at a proximal portion of the first biocompatible layer 114, a greater number of the traction loops 120 can be formed onto the proximal portion of the outer surface 118 of the first biocompatible layer 114 in comparison to the remainder of the outer surface 118.

In addition, the cartridge deck may also include attachment means for releasably holding the traction loops 120 to improve the traction between the compressible adjunct 110 and the cartridge deck 16, for example. Moreover, the first biocompatible layer 114 may be designed to include especially dense section(s) for thermoforming or bonding to the cartridge deck 16.

Figure 15:
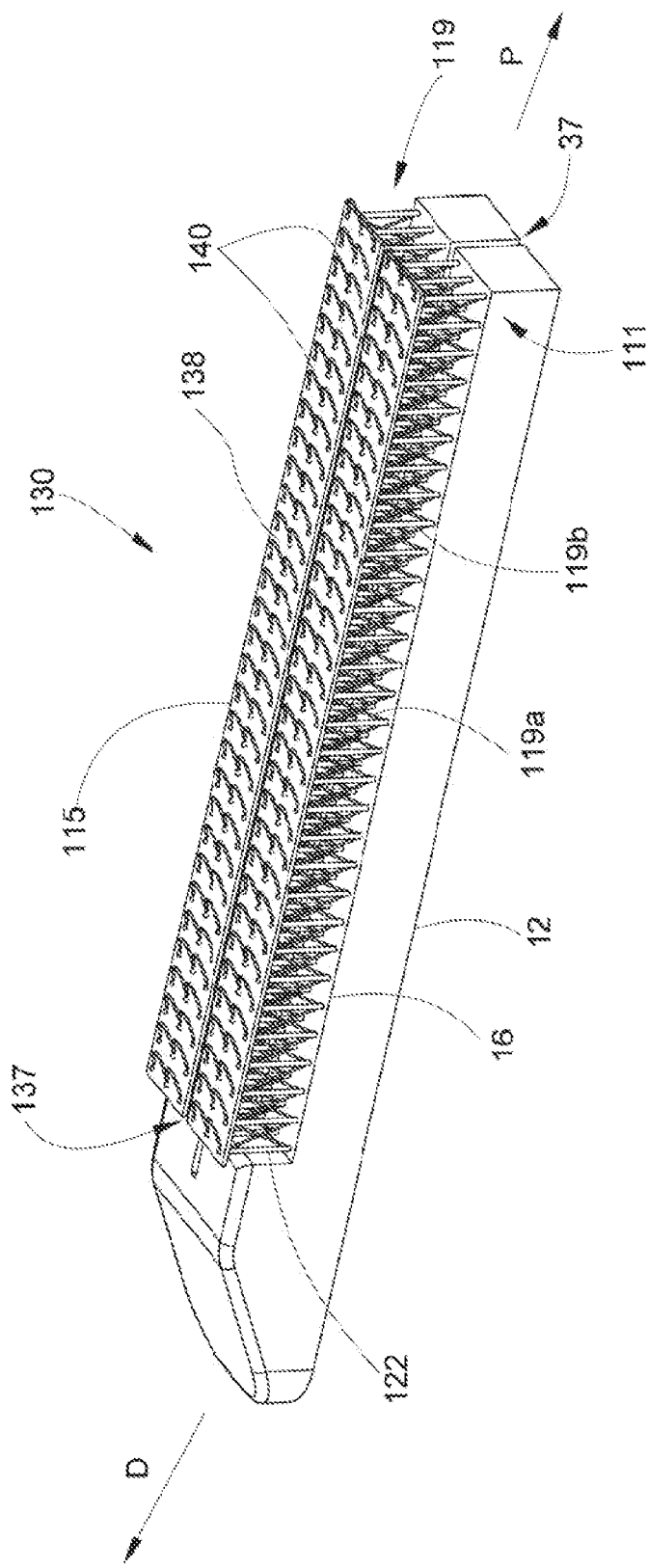
FIG. 15 is a perspective view of a staple cartridge assembly comprising an alternative compressible adjunct in accordance with at least one embodiment.
Figure 16:
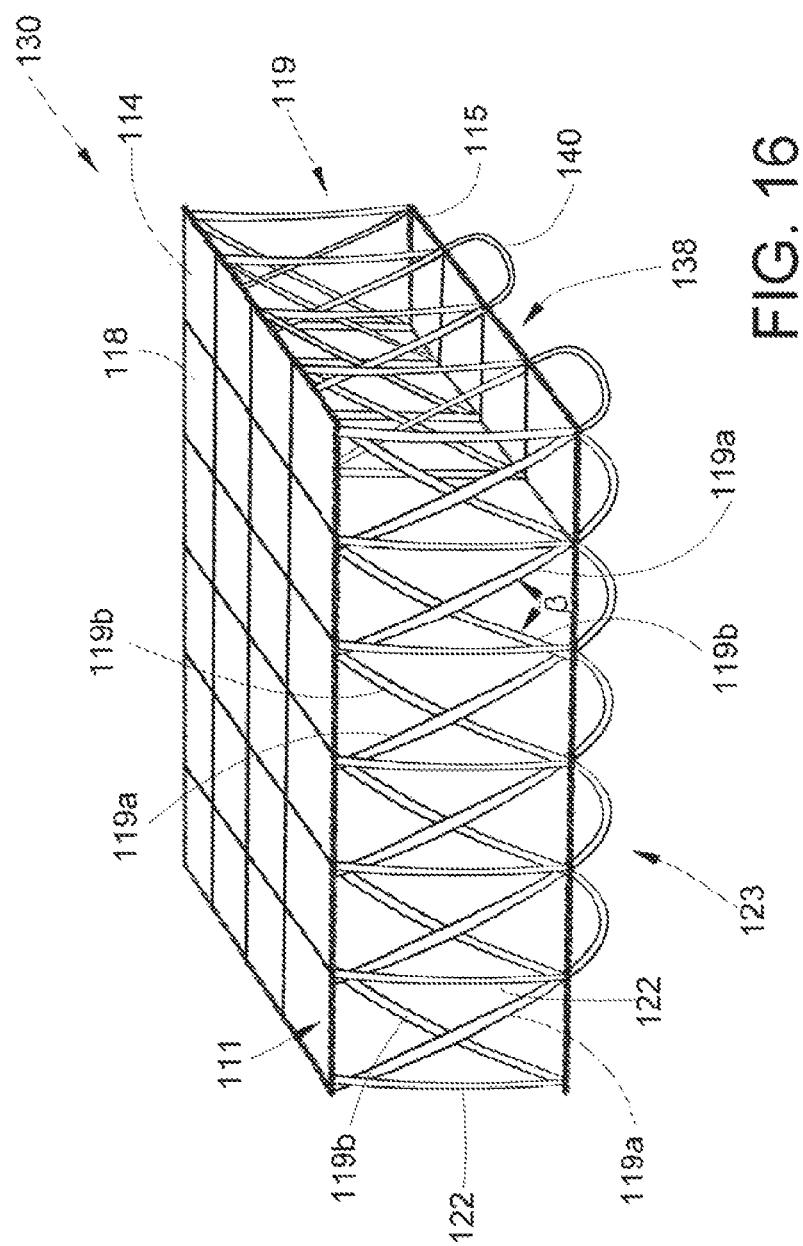
FIG. 16 is a partial perspective view of an alternative compressible adjunct in accordance with at least one embodiment.

Like the first biocompatible layer 114, the second biocompatible layer 115 can also include gripping features for providing traction against tissue. For example, as illustrated in FIGS. 15 and 16, a compressible adjunct 130 includes traction loops 140 that are similar in many respects to the traction loops 120. The traction loops 140 are positioned onto an outer surface 138 of a second biocompatible layer 115. Alternatively, the outer surface 138 of the second biocompatible layer 115 can be smooth, or at least substantially smooth, and/or treated to minimize tissue ingrowth and/or adhesion.

In various instances, the gripping features of the biocompatible layers 114 and 115, including the loops 120 and 140, can be knitted or woven directly onto the biocompatible layers 114 and 115, respectively. In at least one instance, the first biocompatible layer 114 and/or the second biocompatible layer 115 may include satin-type weaves with exposed threads that are longer in a first direction and shorter in a second direction crossing the first direction. The satin-type weaves can increase traction by resisting flow in the second direction. In various instances, the biocompatible layers 114 and 115 can be knitted from one or more multifilament fibers while the standing fibers 119 comprise monofilament fibers. The monofilament fibers 119 can be extended beyond the biocompatible layers 114 and 115 to form the loops 120 and 140. The extensions of the standing fibers 119 can be looped between the courses of the knitting pattern of the biocompatible layers 114 and 115, for example.

In various instances, the gripping features of the biocompatible layers 114 and 115, including the loops 120 and 140, can be angled or slanted to improve traction in a predetermined direction. For example, as illustrated in FIGS. 15 and 16, the loops 140 are slightly angled or slanted in a proximal direction (P) to resist flow of adjacent tissue in a distal direction (D). In an alternative embodiment, the loops 140 can be slightly angled or slanted in the distal direction (D) to resist flow of adjacent tissue in the proximal direction (P). In certain instances, some of the loops 140 can angled or slanted in the proximal direction (P) and some of the loops 140 can be angled or slanted in the distal direction (D). In various instances, increasing the height of a loop 140 increases its resistance to the flow of adjacent tissue.

Referring to FIGS. 14 and 16, a knife channel or slot 137 is defined in the body of each of the compressible adjuncts 110 and 130. When the compressible adjunct 110 and 114 are positioned against a staple cartridge 12, the knife slot 137 is aligned, or at least substantially aligned, with a knife slot 37 that is defined in the staple cartridge 12. The knife slots 37 and 137 are configured to accommodate the cutting edge 9116 as it is advanced to cut tissue captured by the surgical stapling and severing instrument 8010.

A compressible adjunct such as, for example, the compressible adjuncts 110 and/or 130 can be fabricated with a knife slot 137. For example, the knife slot 137 can be woven or knitted as a locally thin area with a reduced fiber density in the body of a compressible adjunct. Alternatively, the knife slot 137 can be created in a compressible adjunct after fabrication. For example, the knife slot 137 can be cut into a compressible adjunct using a solvent, a heat operation, a die cutting operation, a laser cutting operation, an ultrasonic cutting operation, or a combination of these techniques. The knife slot 137 helps to minimize the resistance of the compressible adjunct to the advancement of the cutting edge 9116 which, among other things, can improve the life of the cutting edge 9116 and/or reduce the force required to advance the cutting edge 9116.

Figure 17:
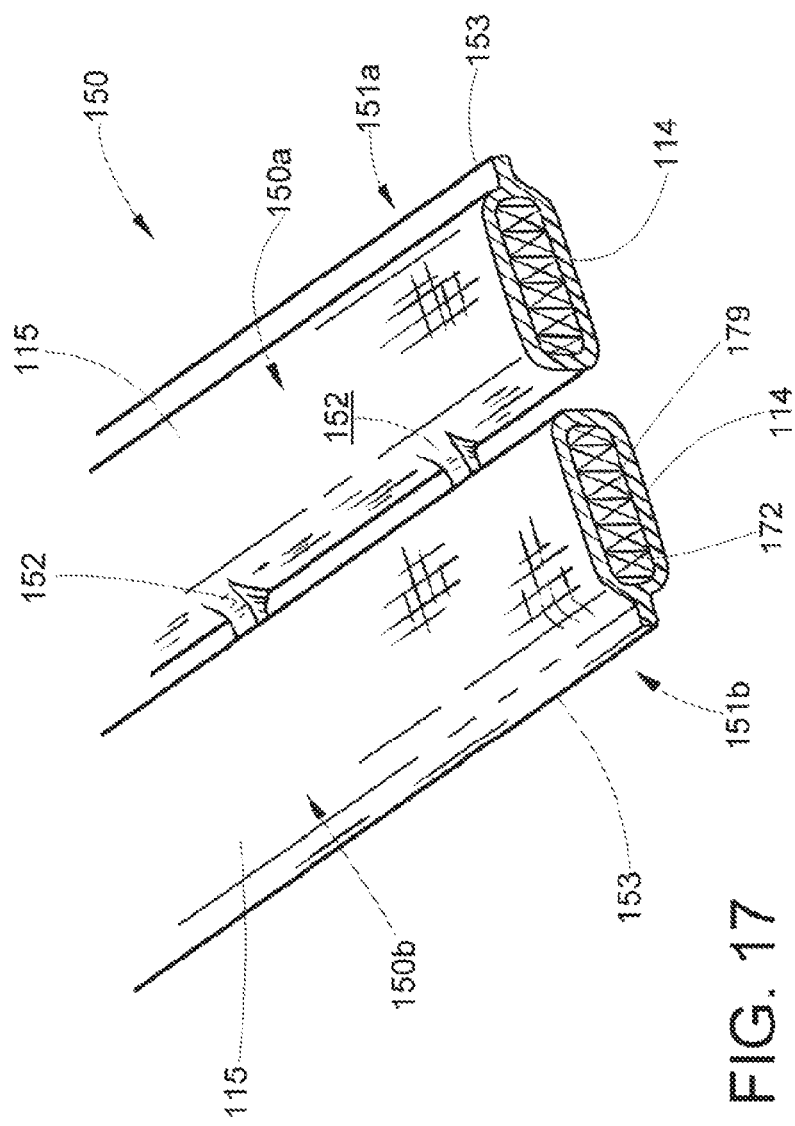
FIG. 17 is a partial perspective view of a compressible adjunct in accordance with at least one embodiment.
Figure 18:
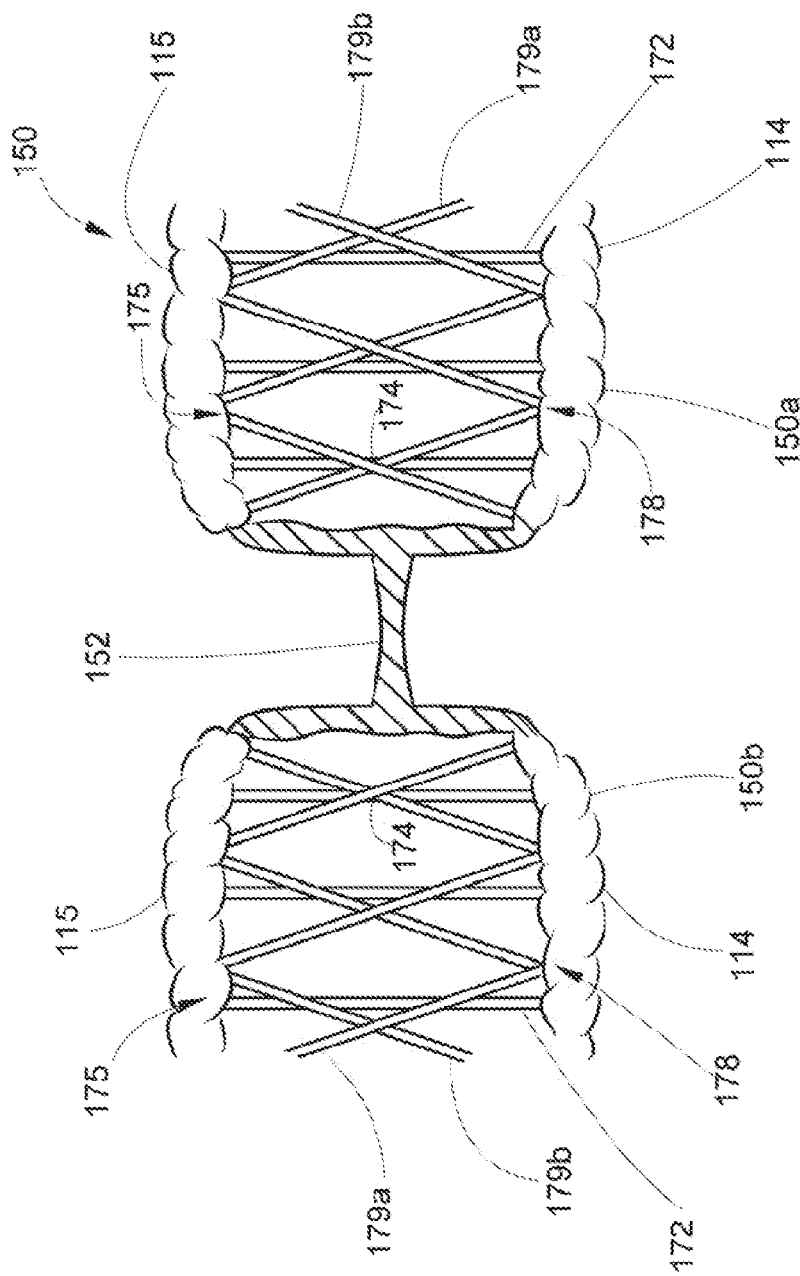
FIG. 18 is a cross-sectional view of the compressible adjunct of FIG. 17.

In certain instances, the knife slot 137 may separate a compressible adjunct into two completely separate portions. Alternatively, as illustrated in FIGS. 17 and 18, a knife slot 137 extending between two portions 150*a* and 150*b* of a compressible adjunct 150 can be interrupted by one or more bridging members 152 configured to tether the two portions 150*a* and 150*b*. Like the compressible adjuncts 110 and 130, each of the portions 150*a* and 150*b* of the compressible adjunct 150 includes a first biocompatible layer 114 positionable against a cartridge deck 16, a second biocompatible layer 115 positionable against the captured tissue, and spacer or standing fibers 179 which are similar in many respects to the standing fibers 119.

Figure 19:
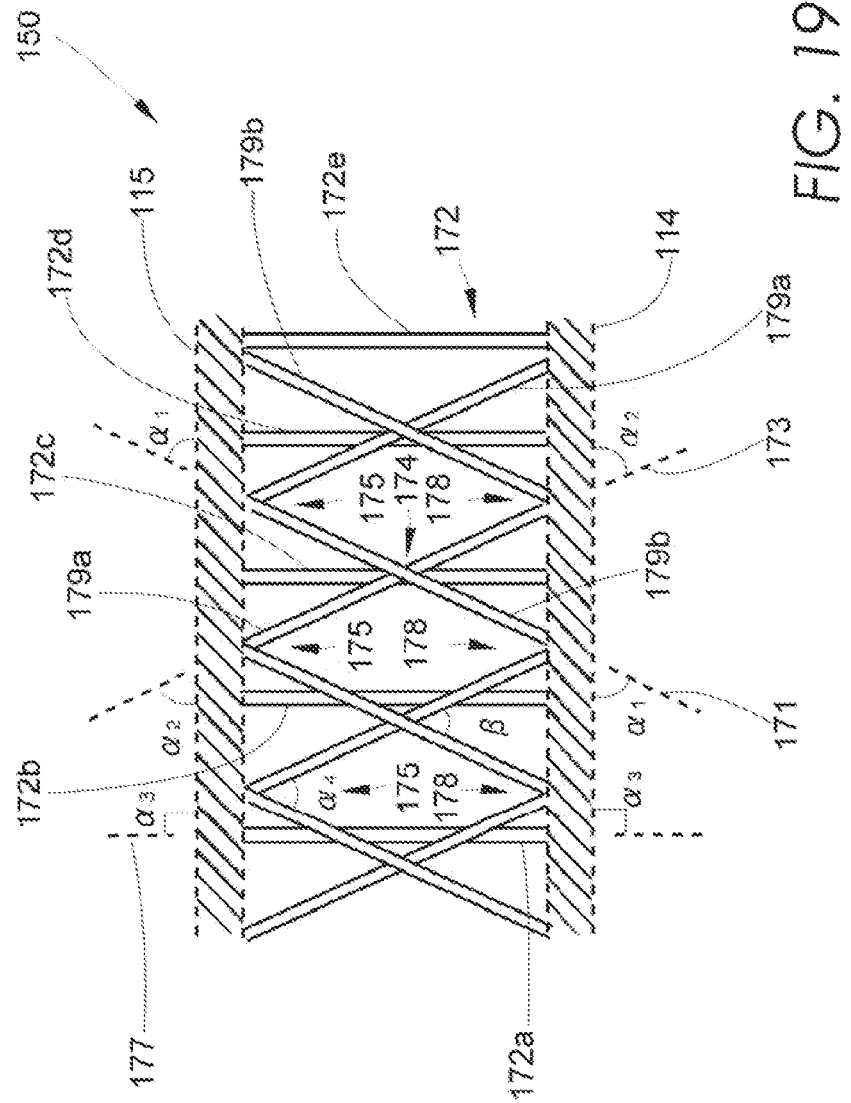
FIG. 19 is a detailed view of the cross-sectional view of FIG. 18.

Referring to FIGS. 17-19, the standing fibers 179 are configured to provide structural support for the compressible adjunct 150. Adjacent fiber portions 179*a* and 179*b* are configured to cross one another, as illustrated in FIGS. 17-19, to increase the stability of the compressible adjunct 150 under compressive and/or shear forces. Applying compressive forces to the compressible adjunct 150 may cause the fiber portions 179*a* and 179*b* to bend and or shift relative to one another. Like the compressible adjunct 51 (FIG. 9), the compressible adjunct 150 can accommodate tissue with portions of different thicknesses.

Referring to FIG. 19, the biocompatible layers 114 and 115 of the compressible adjunct 150 extend in parallel, or at least substantially parallel, with each other. Fiber portions 179*a*, 179*b*, and 172 extend between the biocompatible layers 114 and 115 to maintain a separation between the biocompatible layers 114 and 115. The fiber portions 179*a* are parallel, or at least substantially parallel, to one another. A fiber 179*a* extends, or at least substantially extends, along an axis 171 that intersects the biocompatible layers 114 and 115 at an angle $\alpha 1$. Likewise, the fiber portions 179*b* are parallel, or at least substantially parallel, to one another. A fiber 179*b* extends, or at least substantially extends, along an axis 173 that intersects the biocompatible layers 114 and 115 at an angle $\alpha 2$. In certain instances, the angles $\alpha 1$ and $\alpha 2$ are the same, or at least substantially the same.

The angle $\alpha 1$ can be any angle in a range of about 100 to about 170°, for example. In certain instances, the angle $\alpha 1$ can be any angle in a range of about 30° to about 100°, for example. In certain instances, the angle $\alpha 1$ can be any angle in a range of about 500 to about 70°, for example. Other values for the angle $\alpha 1$ are contemplated by the present disclosure.

The angle $\alpha 2$ can be any angle in a range of about 100 to about 170°, for example. In certain instances, the angle $\alpha 2$ can be any angle in a range of about 300 to about 100°, for example. In certain instances, the angle $\alpha 2$ can be any angle in a range of about 500 to about 70°, for example. Other values for the angle $\alpha 2$ are contemplated by the present disclosure.

As illustrated in FIG. 19, the fiber portions 179*a* and 179*b* may cross one another defining a plurality of "X-shaped" structures. Bonding nodes or interfaces 175 and 178 are defined in the biocompatible layers 115 and 114, respectively, between the neighboring X-shaped structures. Ends of the fiber portions 179*a* and 179*b* intersect at the bonding nodes 175 and 178. An angle $\beta$ is defined between crossing fiber portions 179*a* and 179*b*. The angle $\beta$ can be any angle in a range of about 100 to about 180°, for example. In certain instances, the angle $\beta$ can be any angle in a range of about 30° to about 100°, for example. In certain instances, the angle $\beta$ can be any angle in a range of about 500 to about 70°, for example. In at least one instance, the angle $\beta$ is equal, or at least substantially equal, to the angle $\alpha 1$ and/or the angle $\alpha 2$, for example.

Furthermore, fiber portions 172, including fiber portions 172*a*-172*e*, extend between the biocompatible layers 114 and 115. The fiber portions 172 are perpendicular, or at least substantially perpendicular, to the biocompatible layers 114 and 115. As illustrated in FIG. 19, a fiber portion 172*a* extends, or at least substantially extends, along an axis 177 that intersects the biocompatible layers 114 and 115 at an angle $\alpha 3$. The angle $\alpha 3$ can be any angle in a range of about 800 to about 100°, for example. In certain instances, the angle $\alpha 3$ can be any angle in a range of about 850 to about 95°, for example. In certain instances, the angle $\alpha 3$ can be any angle in a range of about 870 to about 93°, for example. Other values for the angle $\alpha 3$ are contemplated by the present disclosure.

Moreover, the fiber portions 172 are spaced apart from one another. The fiber portions 172 can be equidistant from one another or arranged in any other suitable configuration. As illustrated in FIG. 19, a fiber portion 172*c* passes through an intersection point 174 of an X-shaped structure defined by crossing fiber portions 179*a* and 179*b*. A fiber portion 172*d* partially passes through an intersection point 174 of an X-shaped structure defined by crossing fiber portions 179*a* and 179*b*. In certain instances, two or more fiber portions 172 can pass, or partially pass, through intersection points of X-shaped structures defined by crossing fiber portions 179*a* and 179*b*. In certain instances, bonding nodes or interfaces can be created at one or more of the intersection points 174 by using a biocompatible bonding medium such as, for example, biocompatible glue.

Referring to FIG. 19, a fiber portion 172*b* is positioned on a side of an X-shaped structure of crossing fiber portions 179*a* and 179*b* such that the fiber portion 172*b* intersects the crossing fiber portions 179*a* and 179*b* of such X-shaped structure. In certain instances, two or more fiber portions 172 can positioned like the fiber portion 172*b* with respect to two or more X-shaped structures.

As illustrated in FIG. 19, the bonding nodes 175 are vertically aligned, or at least substantially aligned, with the bonding nodes 178. In certain instances, fiber portions 172 may extend between the bonding nodes 175 and 178 that are vertically aligned such as, for example, the fiber portion 172*e*.

Referring to FIGS. 17 and 18, the bridging members 152 are severed by the cutting edge 9116 during advancement of the cutting edge 9116 to cut the tissue captured by the surgical stapling and severing instrument 8010. Alternatively, one or more of the bridging members 152 may be positioned outside the path of the cutting edge 9116, and may continue to tether the portions 150a and 150b after the surgical stapling and severing instrument 8010 is fired.

Referring to FIGS. 20-22, portions 150a and 150b of a compressible adjunct 160 are tethered via bridging members 162. As illustrated in FIG. 20, the bridging members 162 are spaced apart to provide discrete attachment means between the portions 150a and 150b along a length of the knife slot 137. One or more of the bridging members 162 can be severed by the cutting edge 9116 as it is advanced to cut tissue captured by the surgical stapling and severing instrument 8010.

As illustrated in FIGS. 21 and 22, the bridging members 162 are also configured to attach or tether the compressible adjunct 160 to a staple cartridge 12. Segments of the bridging members 162 are extended through cutouts or holes 164 in a bottom portion 17 of the staple cartridge 12 to secure the compressible adjunct 160 to the staple cartridge 12. The bridging members 162 can also passed through the knife slots 37 and 137. The bridging members 162 can be severed to release the portions 150a and 150b from each other and/or the staple cartridge 12 by shearing or cutting actions caused by the passing of the cutting edge 9116 as the cutting edge 9116 is advanced to cut tissue captured by the surgical stapling and severing instrument 8010.

As illustrated in FIGS. 21 and 22, the cutouts 164 are formed at discrete positions on opposite sides of the knife slot 37 of the staple cartridge 12. In certain instances, the bridging members 162 are in the form of sutures, for example, that are threaded through the cutouts 164 to attach the compressible adjunct 160 to the staple cartridge 12. In certain instances, the cutouts 164 can be replaced or used in combination with projections that extend from the bottom portion 17 of the staple cartridge 12. The projections can be configured to hold the segments of the bridging members 162 that attach the compressible adjunct 160 to the staple cartridge 12. Other attachment means can be formed in the staple cartridge 12 to facilitate attachment of the compressible adjunct 160 to the staple cartridge 12 by the bridging member 162.

Figure 23:
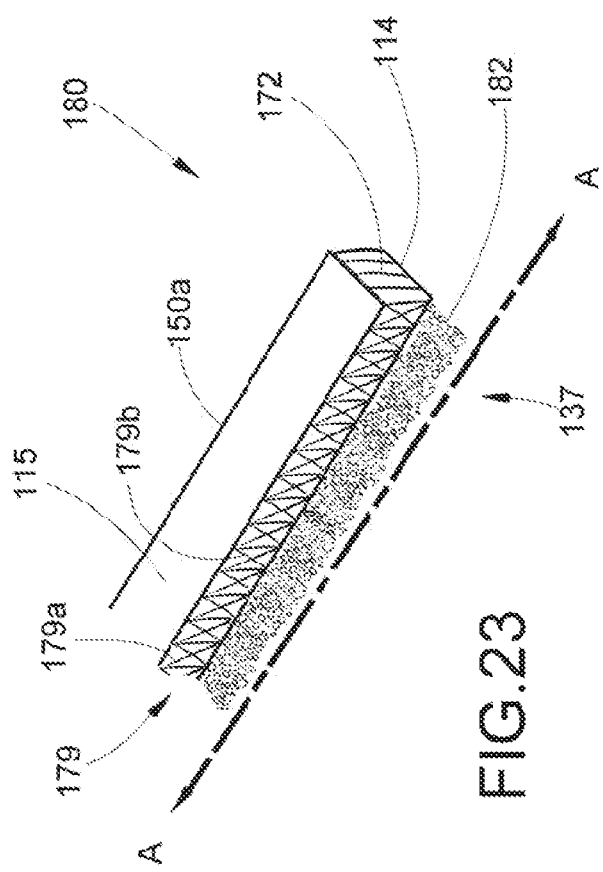
FIG. 23 is a partial perspective view of a compressible adjunct in accordance with at least one embodiment.

Referring to FIG. 23, a bridging sheath 182 may extend between two portions of a compressible adjunct 180. In FIG. 23, the bridging sheath 182 has been severed by the cutting edge 9116. Only one portion 150a of the compressible adjunct 180 is shown. Also, a portion of the severed bridging sheath 182 that remained attached to the portion 150a of the compressible adjunct 180 is shown. The cutting edge 9116 is advanced through the knife slots 37 and 137 along a path defined by a longitudinal axis AA to sever the bridging sheath 182.

In certain instances, as illustrated in FIG. 23, the bridging sheath 182 is defined between the portions of the compressible adjunct 180 at the bottom of the knife slot 137. In such instances, the bridging sheath 182 can be a part of the first biocompatible layer 114 that extends between the two portions of the compressible adjunct 180. Also, in such instances, when the compressible adjunct 180 is positioned against the cartridge deck 16 of the staple cartridge 12, the bridging sheath 182 separates, or at least partially separates, the knife slot 137 of the compressible adjunct 180 and the knife slot 37 of the staple cartridge 12.

In other instances, the bridging sheath 182 is defined between the portions of the compressible adjunct 180 at the top of the knife slot 137 of the compressible adjunct 180. In such instances, the bridging sheath 182 can be a part of the second biocompatible layer 115 that extends between the two portions of the compressible adjunct 180. Also, in such instances, when the compressible adjunct 180 is positioned against the cartridge deck 16 of the staple cartridge 12, the bridging sheath 182 does not separate the knife slot 137 of the compressible adjunct 180 from the knife slot 37 of the staple cartridge 12. Instead, the knife slots 137 and 37 are positioned below the bridging sheath 182. In yet other instances, the bridging sheath 182 may extend between the portions of the compressible adjunct 180 through, or at least substantially through, a plane defined between the biocompatible layers 114 and 115 of the compressible adjunct 180, for example.

Referring again to FIG. 23, the compressible adjunct 180 can be attached to the staple cartridge 16 by tethering the bridging sheath 182 to the bottom portion 17 of the staple cartridge 16. For example, attachment means such as sutures can be threaded through the bridging sheath 182 and the cutouts 164 to tether the bridging sheath 182 to the bottom portion of the staple cartridge 12. The sutures can be severed by the cutting edge 9116, for example, to progressively release the compressible adjunct 180 from the staple cartridge 12. Attaching the compressible adjunct 180 to the staple cartridge 16 by passing the sutures only through bridging sheath 182 at the bottom of the knife slot 137 frees the remainder of the compressible adjunct 180 to be compressed without losing attachment tension in the sutures. The same can be achieved by passing the sutures only through the first biocompatible layer 114, for example.

Figure 24:
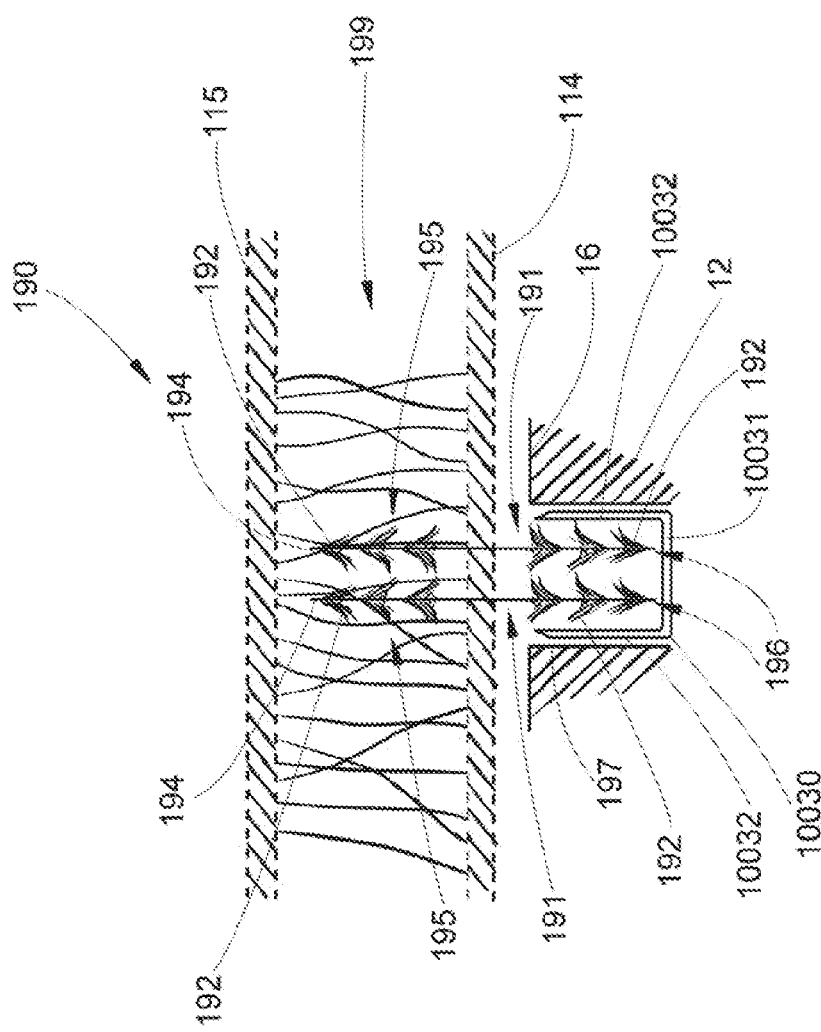
FIG. 24 is a partial cross-sectional view of a staple cartridge assembly in accordance with at least one embodiment.
Figure 25:
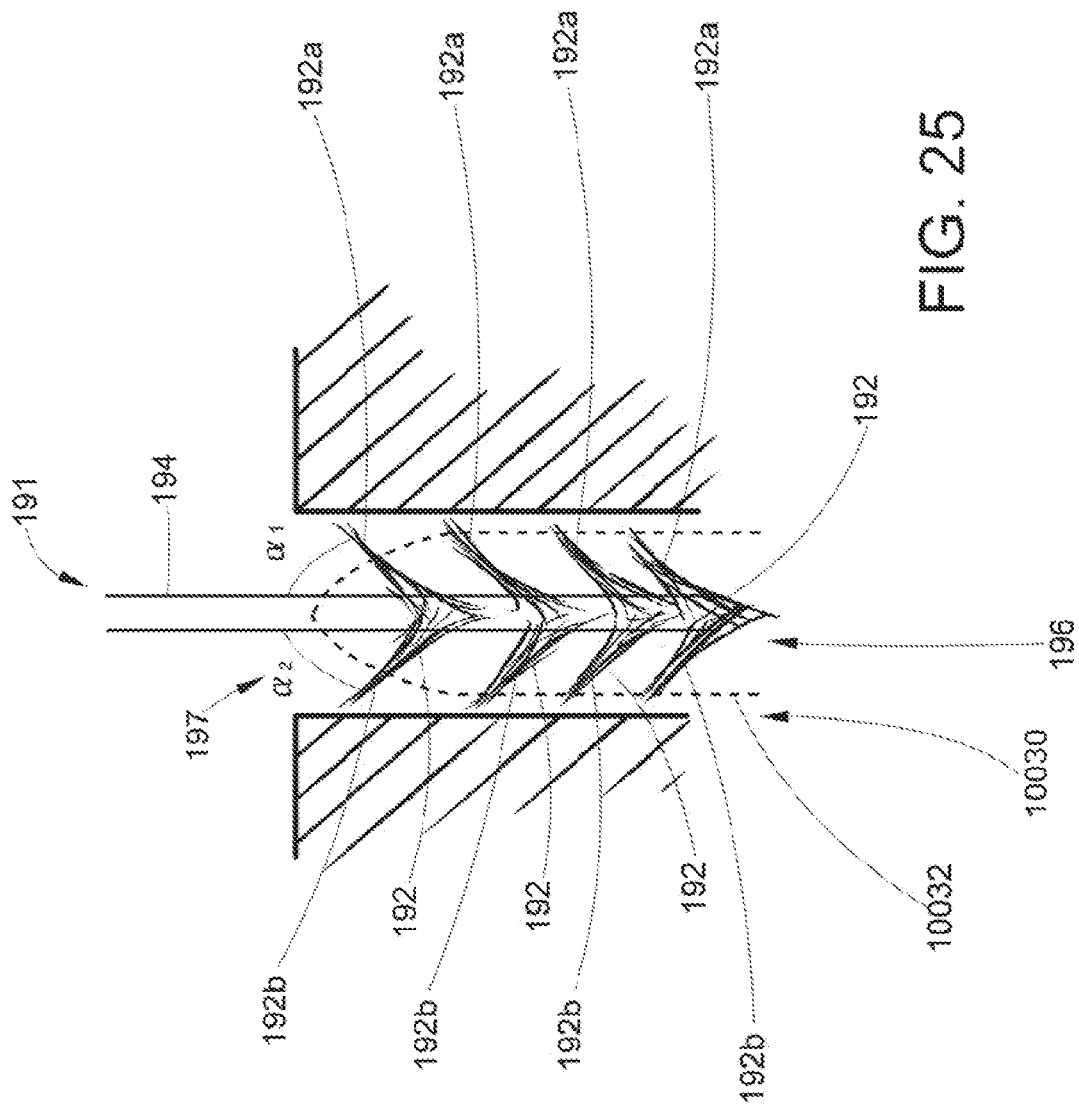
FIG. 25 is a partial cross-sectional view of a securing member inserted into a staple cavity of a staple cartridge in accordance with at least one embodiment.

Referring to FIGS. 24 and 25, a compressible adjunct 190 is positioned against a cartridge deck 16 of a staple cartridge 12. The compressible adjunct 190 is similar in many respects to the compressible adjuncts 11, 31, 51, 81, 81', 100, 110, 130, 150, and/or 180. For example, the compressible adjunct 190 includes a first biocompatible layer 114, a second biocompatible layer 115, and spacer or standing fibers 199 extending between the biocompatible layers 114 and 115.

As illustrated in FIG. 24, the compressible adjunct 190 is secured to the staple cartridge 12 by securing members 191 that include bendable barbs or projections 192 protruding from an elongate support member 194. The bendable projections 192 are shaped like arrow heads that are configured to pierce into a structure with relative ease but resist removal from the structure until sufficient force is applied to bend the bendable projections 192 away from the elongate support member 194.

The bendable projections 192 are arranged on opposite end portions 195 and 196 of the elongate support member 194. In at least one example, as illustrated in FIG. 24, three bendable projections 192 are positioned on each of the opposite end portions 195 and 196. The bendable projections 192 of each of the opposite end portions 195 and 196 are spaced apart with equal distances therebetween. More or less than three bendable projections 192 can be placed on each of the opposite end portions 195 and 196. Other arrangements of the bendable projections 192 with respect to the elongate support member 194 are contemplated by the present disclosure.

Referring to FIG. 24, two securing members 191 are employed to secure at least a portion of the compressible cartridge 190 to the staple cartridge 12. More or less than two securing members 191 can be employed to secure the compressible cartridge 190 to the staple cartridge 12. As illustrated in FIG. 24, end portions 195 of the securing members 191 are inserted through the biocompatible layer 114 while end portions 196 are inserted through the cartridge deck 16 into a staple cavity 197 of the staple cartridge 12. A staple 10030 is positioned in the staple cavity 197. The deployment of the staple 10030 from the staple cavity 197 is blocked, or at least partially blocked, by the end portions 196. As the staple 10030 is deployed from the staple cavity 197, the staple 10030 pushes the end portions 196 out of the staple cavity 197 freeing the securing members 191 from the staple cartridge 12.

End portions 196 of other securing members 191 can be progressively freed from other staple cavities 197 of the staple cartridge 12 during deployment of their respective staples 10030. Since the staples 10030 are progressively released from their respective staple cavities 197 by advancement of the wedge sled 9126 (FIG. 4), a corresponding progressive release of the compressible adjunct 190 is also achieved by the advancement of the wedge sled 9126 during the firing sequence of the surgical stapling and severing instrument 8010. Essentially, a securing member 191 with an end portion 196 that is inserted into a more proximal staple cavity is released before a securing member 191 with an end portion 196 that is inserted into a more distal staple cavity.

The progressive release of the compressible adjunct 190 maintains the relative positioning between the compressible adjunct 190 and staple cartridge 12 at discrete locations on the cartridge deck 16 until the staples 10030 at such locations are fired from their respective staple cavities 197. The securing members 191 also resist bunching of the compressible adjunct 190 that may occur as the cutting edge 9116 is advanced during the firing sequence of the surgical stapling and severing instrument 8010.

Referring to FIG. 24, the securing members 191 at a staple cavity 197 extend in parallel, or at least substantially in parallel, to one another. In at least one instance, the securing members 191 at a staple cavity 197 may cross one another defining an "X" shape, for example.

Referring to FIG. 24, the most exterior bendable projections 192 on each of the opposite end portions 195 and 196 of the elongate support member 194 can define piercing tips for penetrating through a structure. The piercing tips can be especially hardened to facilitate penetration into a structure. Furthermore, the arrow head shape of the bendable projections 192 may improve the stability of the attachment between the securing members 191 and the compressible adjunct 190 by entanglement of the bendable projections 192 with the standing fibers 199, for example.

Referring to FIG. 25, an end portion 196 of an elongate support member 194 of a securing member 191 is inserted into a staple cavity 197 of the staple cartridge 12. The end portion 196 includes four bendable projections 192 that define attachment portions 192a protruding from the elongate support member 194 on a first side of the elongate support member 194 and attachment portions 192b protruding from the elongate support member 194 on a second side of the elongate support member 194 opposite the first side. The attachment portions 192a define an angle α1 with the elongate support member 194 on the first side while the attachment portions 192b define an angle α2 with the elongate support member 194 on the second side.

In certain instances, the angle α1 and/or the angle α2 can be any angle in a range of about 10 to about 90°, for example. In certain instances, the angle α1 and or the angle α2 can be any angle in a range of about 30° to about 70°, for example. In certain instances, the angle α1 and or the angle α2 can be any angle in a range of about 40° to about 60°, for example. In at least one instance, the angle α1 is equal, or at least substantially equal, to the angle α2. In at least one instance, the angle α1 is different from the angle α2.

As illustrated in FIG. 25, the bendable projections 192 each include attachment portions 192a and 192b extending from a same position on the elongate support member 194. Alternatively, a bendable projection 192 may include only one of the attachment portions 192a and 192b. In at least one instance, the attachment portions 192a and 192b of the bendable projections 192 are made from biocompatible fibers that extend from the elongate support member 194. In at least one instance, the elongate support member 194 can also be made from biocompatible fibers.

In various instances, the edges of a compressible adjunct can be configured to improve attachment with a cartridge deck 16 of a staple cartridge 12 and/or improve the structural performance of the compressible adjunct. As illustrated in FIG. 17, edges 151a and 151b of the portions 150a and 150b, respectively, of the compressible adjunct 150 are each formed down to an outer lip 153 which defines an outer perimeter of the compressible adjunct 150, and can be attached to the cartridge deck 16, for example.

Figure 26:
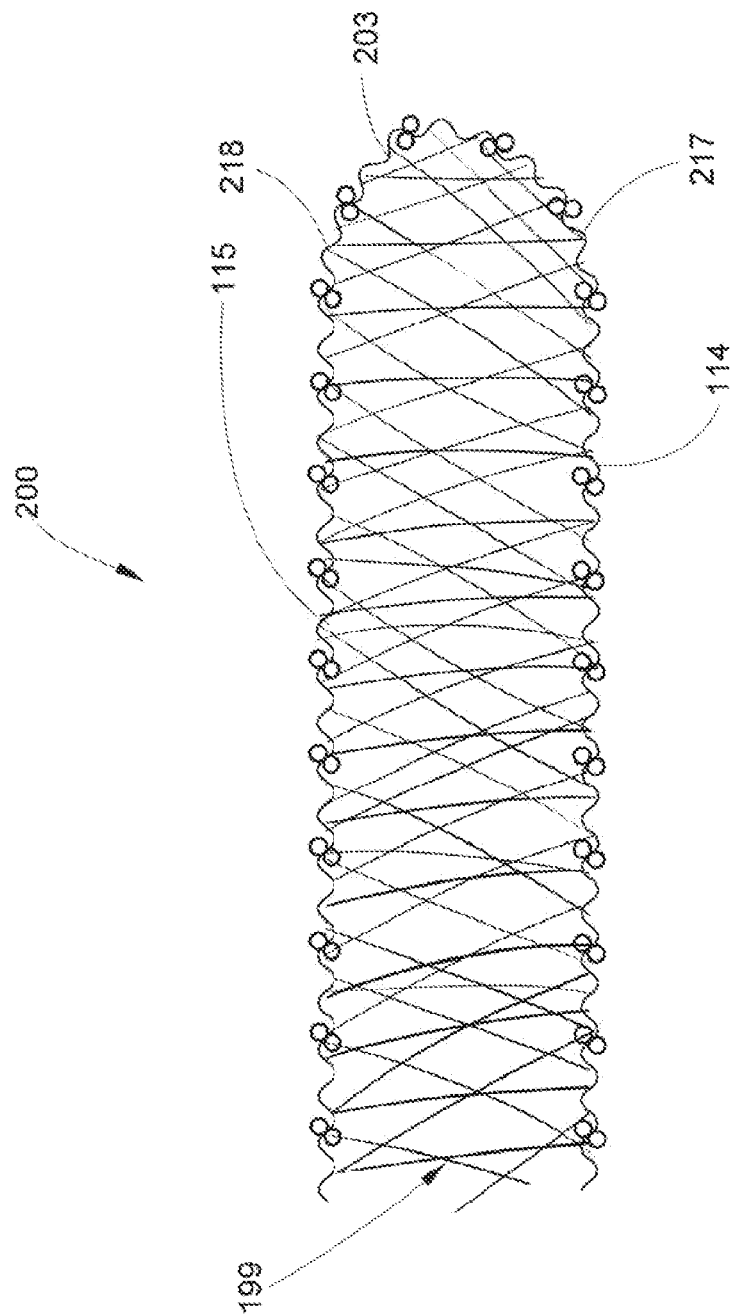
FIG. 26 is a partial cross-sectional view of a compressible adjunct in accordance with at least one embodiment.

In certain instances, an outer lip can be formed after fabrication of a compressible adjunct. For example, the outer perimeters of the biocompatible layers of a compressible adjunct can be subjected to heat and/or pressure to form the outer lips. In certain instances, outer lips can be formed by weaving or knitting, for example, outer perimeters of the biocompatible layers of a compressible adjunct into a united structure that defines the outer lips. As illustrated in FIG. 26, an outer lip 203 of a compressible adjunct 200 is formed by knitting outer perimeters 217 and 218 of the biocompatible layers 114 and 115, respectively, of a compressible adjunct 200 into a united structure that defines the outer lip 203.

Uniting the outer perimeters of the biocompatible layers of a compressible adjunct can help stabilize the compressible adjunct and/or minimize shear collapse during compression. In certain instances, however, it is desirable to maintain the spacing between the outer perimeters of the biocompatible layers of a compressible adjunct to minimize structural and/or other differences between the outer perimeters and the center of a compressible adjunct that may result from the modification.

Figure 27:
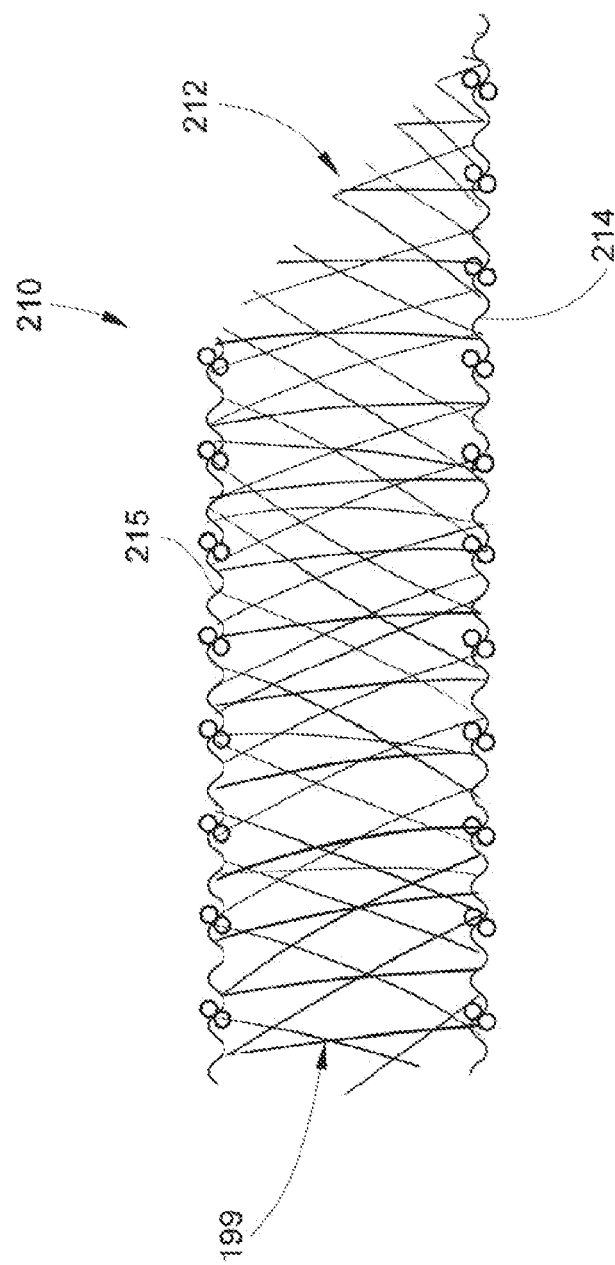
FIG. 27 is a partial cross-sectional view of a compressible adjunct in accordance with at least one embodiment.

Referring to FIG. 27, a tapered edge 212 is defined in a compressible adjunct 210. The compressible adjunct 210 includes a first biocompatible layer 214 which extends laterally beyond a second biocompatible layer 215. Alternatively, a compressible adjunct 210 can include a second biocompatible layer 215 that extends laterally beyond the first biocompatible layer 214.

The biocompatible layers 214 and 215 are similar in many respects to the biocompatible layers 114 and 115. For example, the first biocompatible layer 214 is configured to be positioned against and/or attached to the cartridge deck 16 and the second biocompatible layer 215 is configured to be positioned against tissue captured between the anvil 8014 and the staple cartridge 12. In at least one instance, a tapered edge 212 of the compressible adjunct 210 is formed by removing or cutting off a portion of the compressible adjunct 210. The cutting plane can be made at a predetermined angle depending on the desired sharpness of the tapered edge 212.

Figure 28:
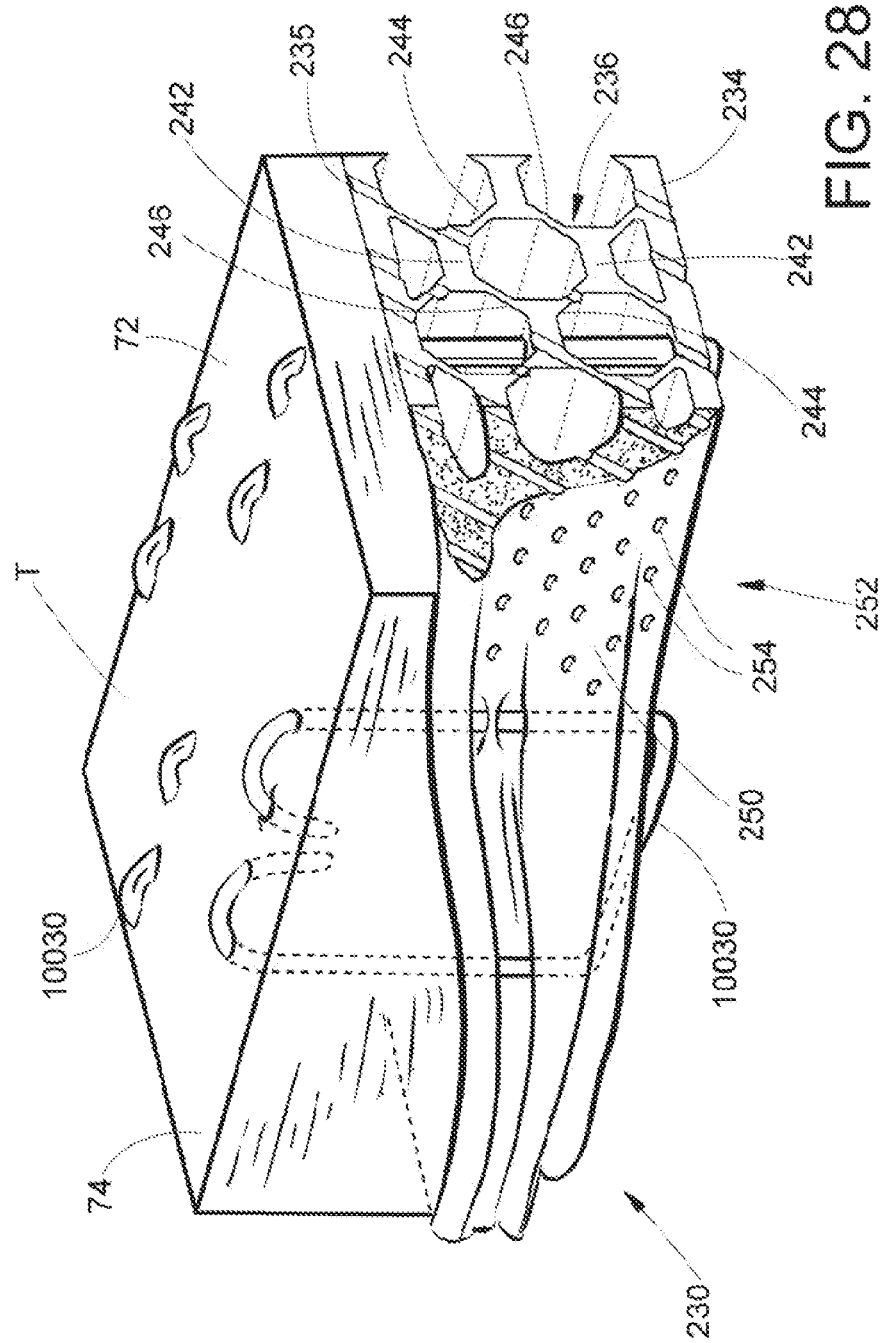
FIG. 28 is a partial perspective view of an alternative compressible adjunct implanted against tissue by at least one staple in accordance with at least one embodiment.
Figure 29:
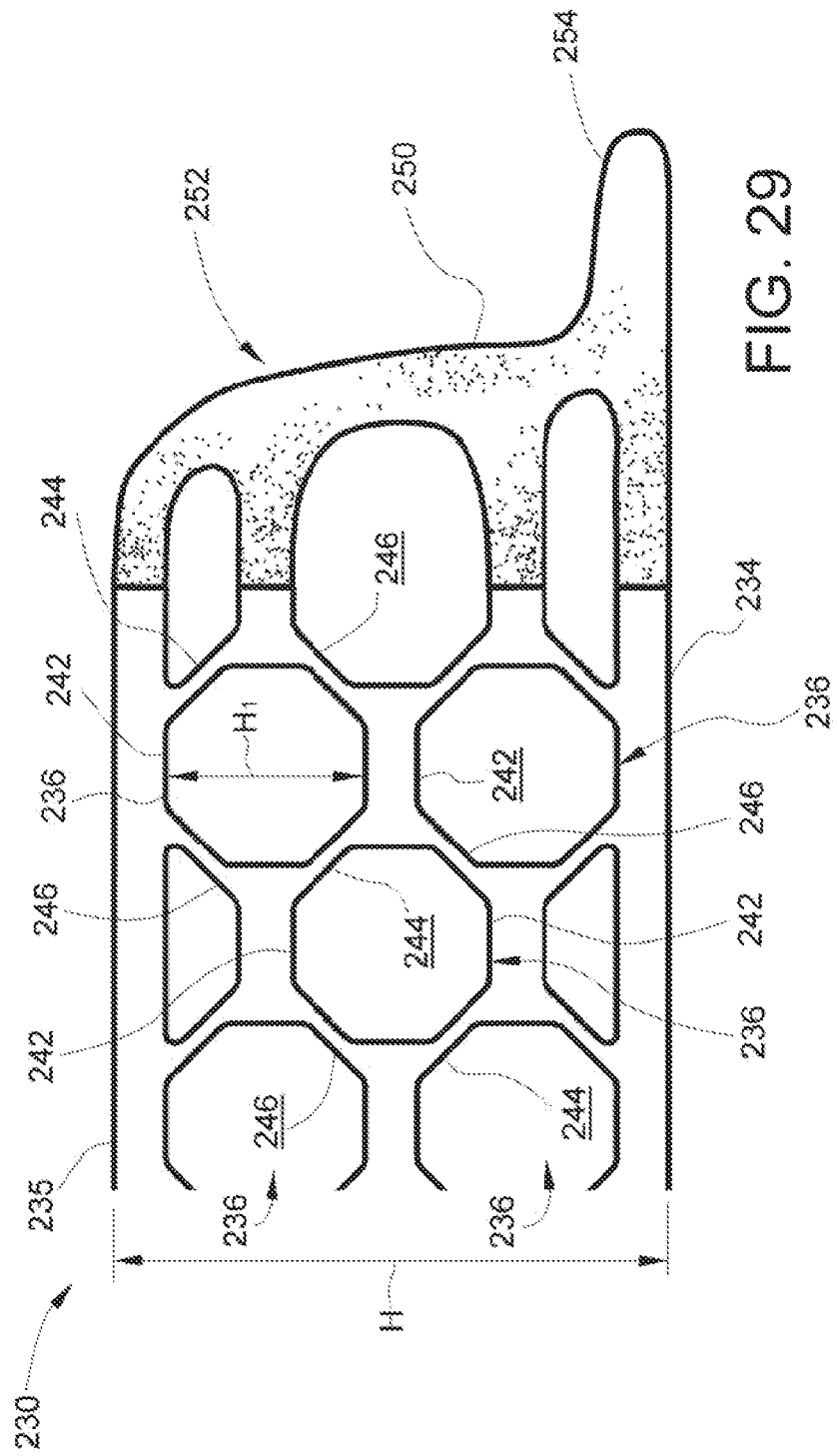
FIG. 29 is a partial cross-sectional view of the compressible adjunct of FIG. 28 without compression.
Figure 30:
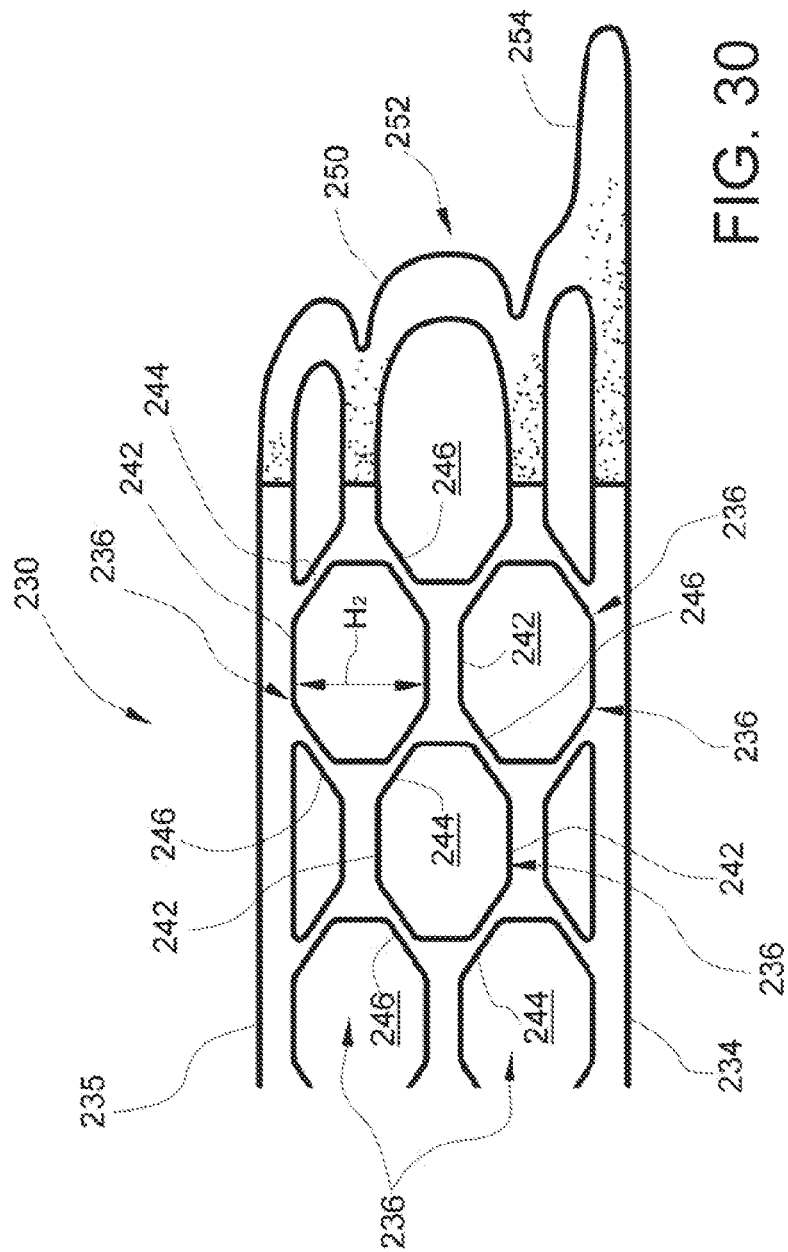
FIG. 30 is the partial cross-sectional view of FIG. 29 under compression.

Referring to FIGS. 28-30, a compressible adjunct 230 is depicted. The compressible adjunct 230 is similar to other compressible adjuncts described in the present disclosure. For example, like the compressible adjunct 51 (FIG. 9), the compressible adjunct 230 can compensate for the variability in the thickness of tissue (T) captured with the compressible adjunct 230 by the staples 10030. As illustrated in FIG. 28, the compressible adjunct 230 is configured to accommodate a tissue (T) with tissue portions 72 and 74 having different tissue thicknesses when the tissue portions 72 and 74 are captured with compressible adjunct 230 by the staples 10030.

Referring to FIG. 28, the compressible adjunct 230 includes a plurality of structural cells 236 positioned between a cartridge contacting surface 234 and a tissue contacting surface 235. One or more of the structural cells 236 can extend longitudinally along, or at least substantially along, an entire length of the compressible adjunct 230. A structural cell 236 is generally surrounded by walls that define an outer perimeter on the structural cell 236. Neighboring structural cells 236 may share one or more walls.

Referring to FIG. 29, a structural cell 236 is defined by six walls and comprises a hexagonal shape. In at least one instance, one or more of the structural cells 236 may each include three or more walls. The structural cells 236 of a compressible adjunct 230 may include the same number of walls. Alternatively, a first group of structural cells 236 may include a first number of walls while a second group of structural cells 236 may include a second number of walls different from the first number of walls, for example. In at least one instance, the structural cells 236 define a honeycomb shape that extends longitudinally along, or at least substantially along, at least a portion of the entire length of the compressible adjunct 230.

The honeycomb shape improves the stability of the compressible adjunct 230 under compressive and/or shear forces. In addition, the honeycomb-shaped structural cells 236 are bendable under compression applied to the compressible adjunct 230 and tissue (T) positioned against the second biocompatible layer 215 as an anvil 8014 is moved into a closed position opposite the staple cartridge 12. As illustrated in FIGS. 29 and 30, the honeycomb-shaped structural cells 236 are configured to experience a reduction in height when compressive forces are applied to the compressible adjunct 230 which permits the compressible adjunct 230 to accommodate tissue (T) with tissue portions 72 and 74 having different tissue thicknesses when the tissue portions 72 and 74 are captured with the compressible adjunct 230 by the staples 10030, as illustrated in FIG. 28.

Referring to FIGS. 29 and 30, a structural cell 236 has experienced a reduction in height from a first height (H1), as illustrated in FIG. 29, to a second height (H2), as illustrated in FIG. 30 in response to the compression forces applied to the compressible adjunct 230 as the anvil 8014 is moved into the closed position opposite the staple cartridge 12. The reduction in height may correspond to the thickness of the captured tissue (T) positioned against the compressible adjunct 230 where the structural cell 236 is located. In other words, the greater the thickness of a tissue portion, the greater the reduction in height of a structural cell 236 located at a portion of the compressible adjunct 230 positioned against that tissue portion.

The ratio of the second height (H2) to the first height (H1) can be any value from about 0.05 to about 0.95, for example. In certain instances, the ratio of the second height (H2) to the first height (H1) can be any value from about 0.2 to about 0.7, for example. In certain instances, the ratio of the second height (H2) to the first height (H1) can be any value from about 0.3 to about 0.6, for example. Other values for the ratio of the second height (H2) to the first height (H1) are contemplated by the present disclosure.

The walls of a structural cell 236 may comprise the same, or at least substantially the same, thickness. Alternatively, as illustrated in FIG. 29, the walls of a structural cell 236 may comprise different thicknesses. A pair of opposite walls 242 may comprise a first thickness (T1), a pair of opposite walls 244 may comprise a second thickness (T2), and a pair of opposite walls 246 may comprise a third thickness (T3), wherein at least two of the first thickness (T1), the second thickness (T2), and/or the third thickness (T3) are different from one another. For example, as illustrated in FIG. 29, the first thickness (T1) of the walls 242 is greater than the second thickness (T2) of the walls 244, and greater than the third thickness (T3) of the walls 246

Referring to FIGS. 28-30, the walls 242 of a structural cell 236 extend in parallel, or at least substantially in parallel, with the first biocompatible layer 234 and the second biocompatible layer 235. In certain instances, a wall 242 of a structural cell 236 may define a portion of the first biocompatible layer 234. In certain instances, a wall 242 of a structural cell 236 may define a portion of the second biocompatible layer 235.

As illustrated in FIG. 28, a building block of a compressible adjunct 230 includes five structural cells 236 that include a central structural cell 236 which shares walls with the other four structural cells 236. A height (H) of a compressible adjunct 230 can be defined by a stack of two structural cells 236 sharing a wall 244, as illustrated in FIG. 29. Alternatively, a height (H) of a compressible adjunct 230 can be defined by a stack of two four-walled structural cells 237 and one structural cell 236 extending between the structural cells 237, as illustrated in FIG. 29. The structural cell 236 shares a wall 242 with each of the structural cells 237. Other geometries and arrangements of the structural walls of a compressible adjunct 230 are contemplated by the present disclosure.

Various attachments can be fixed or secured to a compressible adjunct of the present disclosure. An attachment can be made from the same, or at least substantially the same, material(s) as the compressible adjunct. Alternatively, an attachment can be made from different material(s) than the compressible adjunct. In at least one instance, an attachment can be made from the same material(s) as the compressible adjunct but the material(s) are treated differently to modify one or more of the chemical and/or physical properties, for example, of the attachment.

In at least one instance, a compressible adjunct can be harder or softer than an attachment that is secured to the compressible adjunct. A harder attachment can provide a desirable stiffness for securing the attachment to a cartridge deck, for example. Alternatively, a softer attachment can yield a more delicate interaction with sensitive tissue, for example. In at least one instance, a compressible adjunct may comprise smoother or rougher surfaces than the surfaces of an attachment that is secured to the compressible adjunct. Ultimately, an attachment can be tailored to perform various functions in connection with a compressible adjunct. In various instances, an attachment may be in the form of a side attachment or an end cap for a compressible adjunct.

Referring to FIGS. 28-30, a side attachment 250 is fixed or secured to the compressible adjunct 230. In at least one instance, a side attachment 250 can be secured to the compressible adjunct 230 by welding using heat or a solvent, for example. The side attachment 250 defines a tapered edge 252 of the compressible adjunct 230.

Furthermore, the side attachment 250 can be employed to attach the compressible adjunct 230 to a cartridge deck 16 of a staple cartridge 12, for example. In at least one instance, the side attachment 250 can be welded onto the cartridge deck 16 by using heat or a solvent, for example. Other techniques for securing a side attachment 250 to a compressible adjunct 230 and/or to a cartridge deck 16 are contemplated by the present disclosure. For example, a tether 254 (FIG. 29) of a side attachment 250 can be secured to and/or wrapped around a staple cartridge 12.

A compressible adjunct and/or a side attachment can be configured to facilitate tissue ingrowth. For example, as illustrated in FIGS. 28-30, the compressible adjunct 230 and the side attachment 250 include perforations 254 configured to facilitate tissue ingrowth into the compressible adjunct 230 and the side attachment 250. The perforations 254 can be selectively created through the compressible adjunct 230 and/or the side attachment 250 in areas where tissue ingrowth is desirable.

In various instances, a compressible adjunct 230 and/or a side attachment 250 can be fabricated by various extrusion techniques, for example, and the perforations 254 can be laser drilled, for example, into desired portions of the compressible adjunct 230 and/or the side attachment 250. A side attachment 250 can be attached to a compressible adjunct 230 after extrusion, for example. A tailored compression resistance can be achieved in a compressible adjunct 230 by fabricating the walls of structural cells such as, for example, the structural cells 236 to predetermined thicknesses. Patterns of non-uniform wall thicknesses can be extruded, for example, to tune the flexibility of the structural cells within a compressible adjunct 230 to achieve a desired stiffness regardless of the material(s) used in the fabrication of the compressible adjunct 230.

Figure 31:
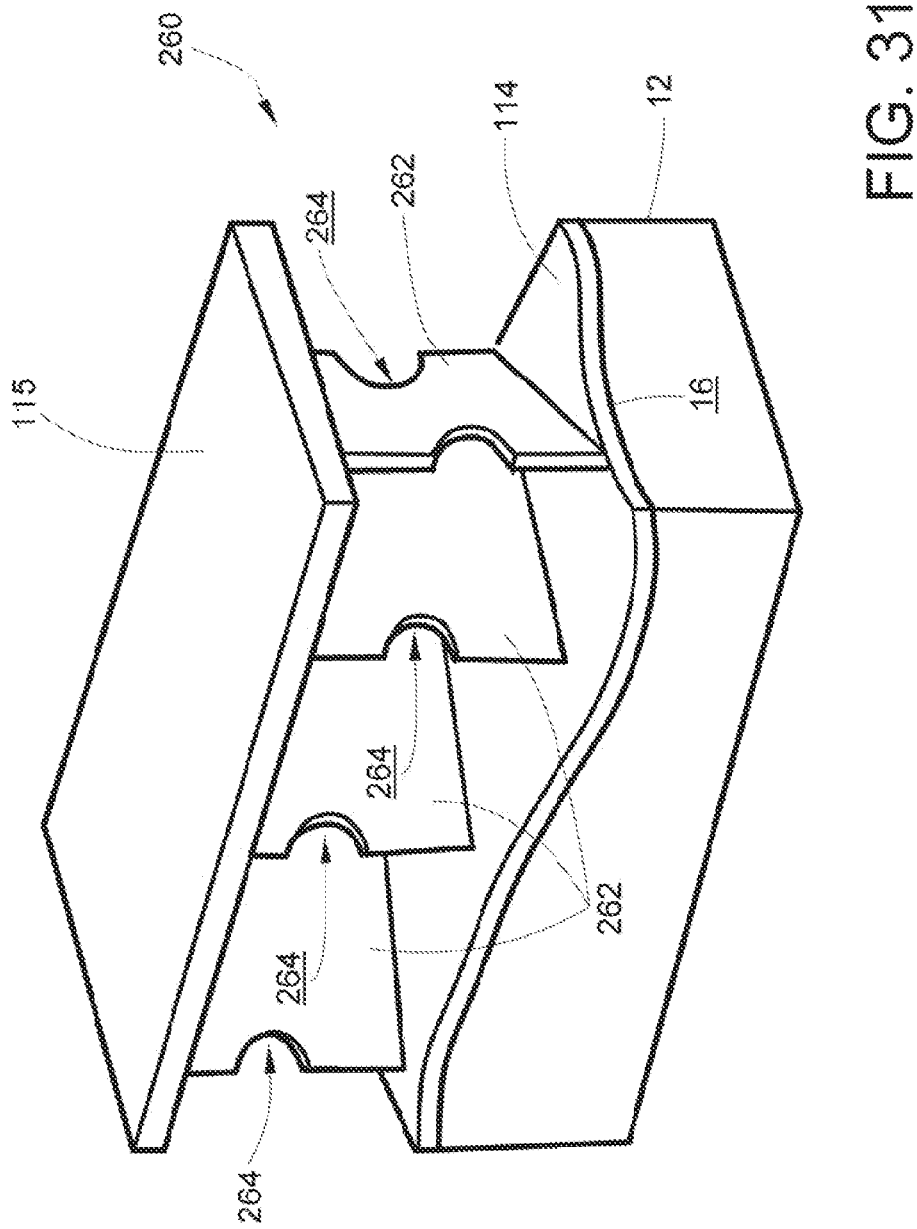
FIG. 31 is a perspective view of a staple cartridge assembly comprising an alternative compressible adjunct in accordance with at least one embodiment.

Referring to FIG. 31, a compressible adjunct 260 is depicted. The compressible adjunct 260 includes a first biocompatible layer 114 positioned against a cartridge deck 16 of a staple cartridge 12. In addition, the compressible adjunct 260 includes a second biocompatible layer 115 positionable against tissue (T). A plurality of standing or spacer walls 262 are defined between the biocompatible layers 114 and 115. The standing walls 262 are configured to maintain a space between the biocompatible layers 114 and 115, as illustrated in FIG. 31. In addition, the standing walls 262 are bendable under compression applied to the compressible adjunct 260 and tissue (T) positioned against the second biocompatible layer 115 as an anvil 8014 is moved into a closed position opposite the staple cartridge 12.

The standing walls 262 are attached to the biocompatible layers 114 and 115, and are spaced apart from one another. Alternatively, the standing walls 262 can be tethered or attached to one another. Some of the standing walls 262 are arranged in parallel, or at least substantially in parallel, to one another. Other standing walls 262, however, extend in intersecting planes.

Furthermore, the standing walls 262 comprise cutouts or gaps 264 that improve the flexibility of the standing walls 262. In at least one instance, one or more of the standing walls 262 can be fabricated with the cutouts 264 by extrusion, for example. Alternatively, the cutouts 264 can be created after fabrication of the standing walls 262 is completed. The cutouts 264 can be strategically positioned to achieve a desired flexibility of the compressible adjunct 260, for example.

Figure 32:
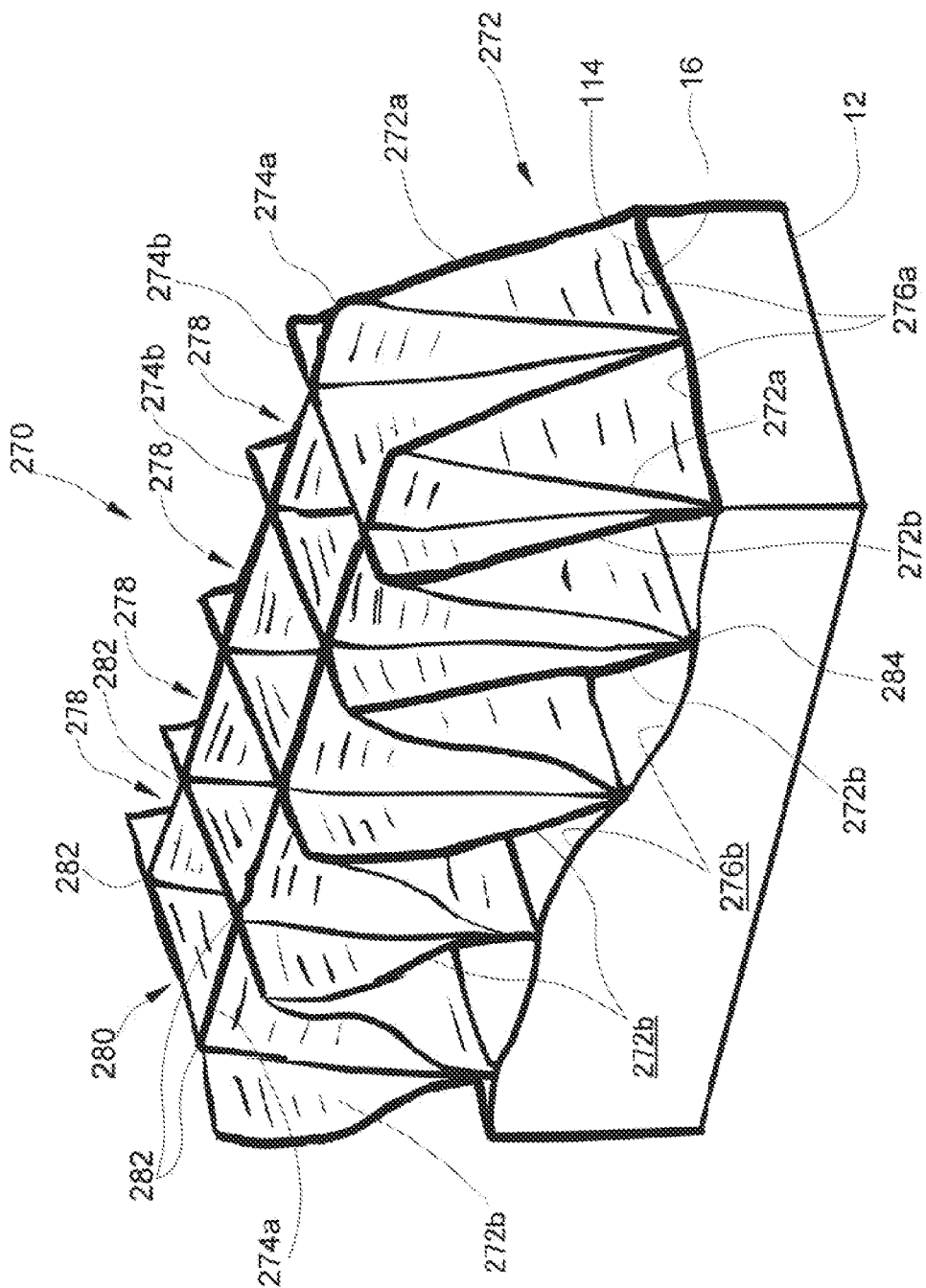
FIG. 32 is a perspective view of a staple cartridge assembly comprising an alternative compressible adjunct in accordance with at least one embodiment.

Referring to FIG. 32, a compressible adjunct 270 includes a first biocompatible layer 114 positioned against a cartridge deck 16 of a staple cartridge 12. The compressible adjunct 270 lacks a second biocompatible layer. Accordingly, tissue (T) is directly positioned against a plurality of spacer or standing walls 272 of the compressible adjunct 270. Alternatively, the compressible adjunct 270 can include a second biocompatible layer on an opposite side of the standing wall 272. In such instances, tissue (T) can be positioned against the second biocompatible layer. In addition, the standing walls 272 are bendable under compression applied to the compressible adjunct 270 and tissue (T) positioned against the standing walls 272 as an anvil 8014 is moved into a closed position opposite the staple cartridge 12.

The standing walls 272 include longitudinal walls 272a and transverse walls 272b intersecting the longitudinal walls 272a. The standing walls 272 comprise hollow, or at least substantially hollow, frames, as illustrated in FIG. 32. Alternatively, the standing walls 272 may comprise solid frames. In various instances, the standing walls 272 comprise the shape of a triangular prism, for example. The standing walls 272 comprise triangular cross-sectional areas. The standing walls 272 may comprise square-shaped, rectangular, and/or curved cross-sectional areas in addition to or instead of the triangular cross-sectional areas. As illustrated in FIG. 32, the longitudinal walls 272a comprise transverse cross-sectional areas that are triangle shaped and the transverse walls 272b comprise longitudinal cross-sectional areas that are triangle shaped.

A longitudinal wall 272a comprises a base 276a defined by the first biocompatible layer 114 and an apex 274a extending longitudinally in parallel, or at least substantially in parallel, with other apexes 274a of neighboring longitudinal walls 272a. A transverse wall 272b also comprises a base 276b defined by the first biocompatible layer 114 and an apex 274b extending transversely in parallel, or at least substantially in parallel, with other apexes 274b of neighboring transverse walls 272b.

As illustrated in FIG. 32, the compressible adjunct 272 includes structural cells 278 that comprise inverted pyramid shapes. A structural cell 278 is defined between two parallel, or at least substantially parallel, walls 272a and two parallel, or at least substantially parallel, walls 272b intersecting the walls 272a. A base 280 of a structural cell 278 comprises four corners 282 defined by the intersecting walls 272a and 272b. An apex 284 of a structural cell 278 is defined at the first biocompatible layer 114. Each structural cell 278 extends from an apex 284 and terminates at a base 280, as illustrated in FIG. 32.

In various instances, the second biocompatible layer of a compressible adjunct of the present disclosure such as, for example, the second biocompatible layer 115 of the compressible adjunct 110 is visible when the compressible adjunct 110 is positioned against a cartridge deck 16 of a staple cartridge 12. In various instances, certain information can be communicated to an operator through images, words, symbols, and/or colors that are knitted or printed onto the second biocompatible layer. For example, knitting lines can be employed to show knife travel length, which may help an operator to reduce the number of loads used in a procedure. Knitting lines can also be employed to show the positions of staple crowns. Moreover, knitting lines can also be employed to provide information about a staple cartridge employed with the compressible adjunct such as, for example staple heights. Furthermore, knitting lines can also be employed to outline an optimal location for positioning the treated tissue against the compressible adjunct.

Figure 33:
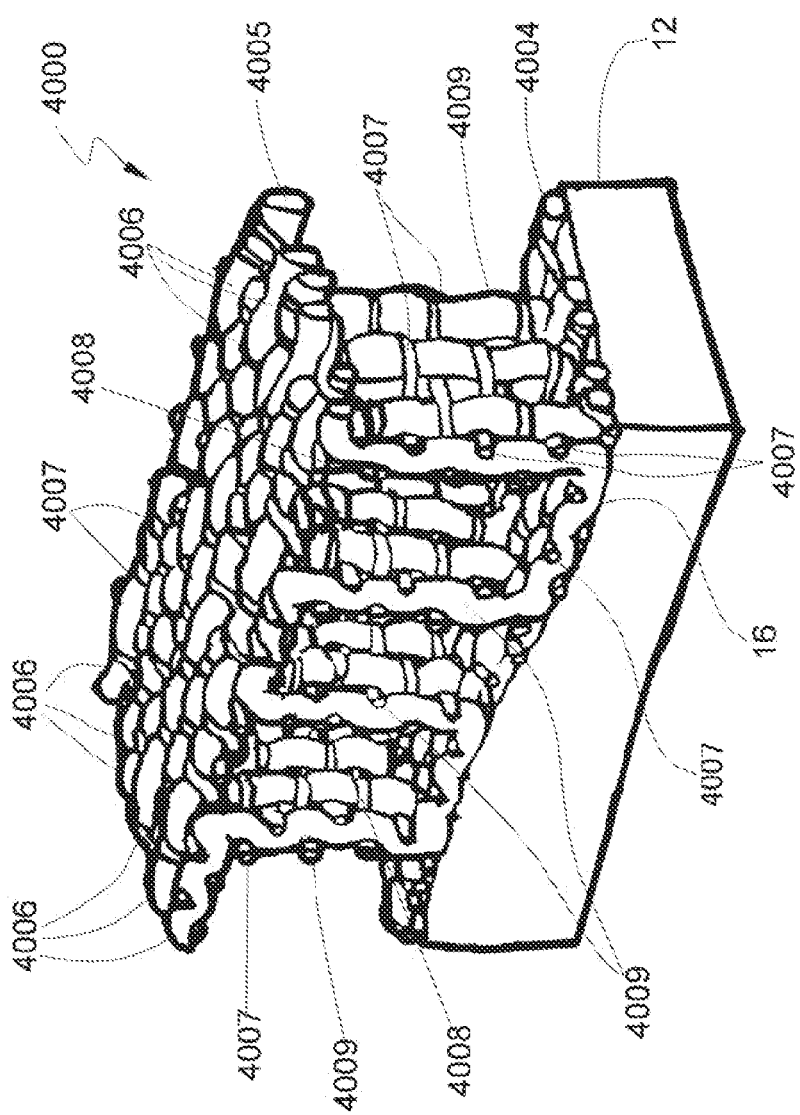
FIG. 33 is a partial perspective view of a staple cartridge assembly comprising an implantable adjunct in accordance with at least one embodiment.

A staple cartridge assembly comprising an implantable layer 4000 is depicted in FIG. 33. The staple cartridge assembly further comprises a cartridge body 12 including a deck 16 which supports the layer 4000. The layer 4000 comprises a bottom portion 4004 supported by the deck 16 and, in addition, a top portion 4005. The bottom portion 4004 and the top portion 4005 are connected by walls 4009. The walls 4009 extend laterally across the layer 4000; however, the walls 4009 can extend in any suitable direction, such as longitudinally, for example. In at least one embodiment, the cartridge body 12 comprises a longitudinal slot configured to receive a cutting member and the walls 4009 extend across the longitudinal slot.

Figure 34:
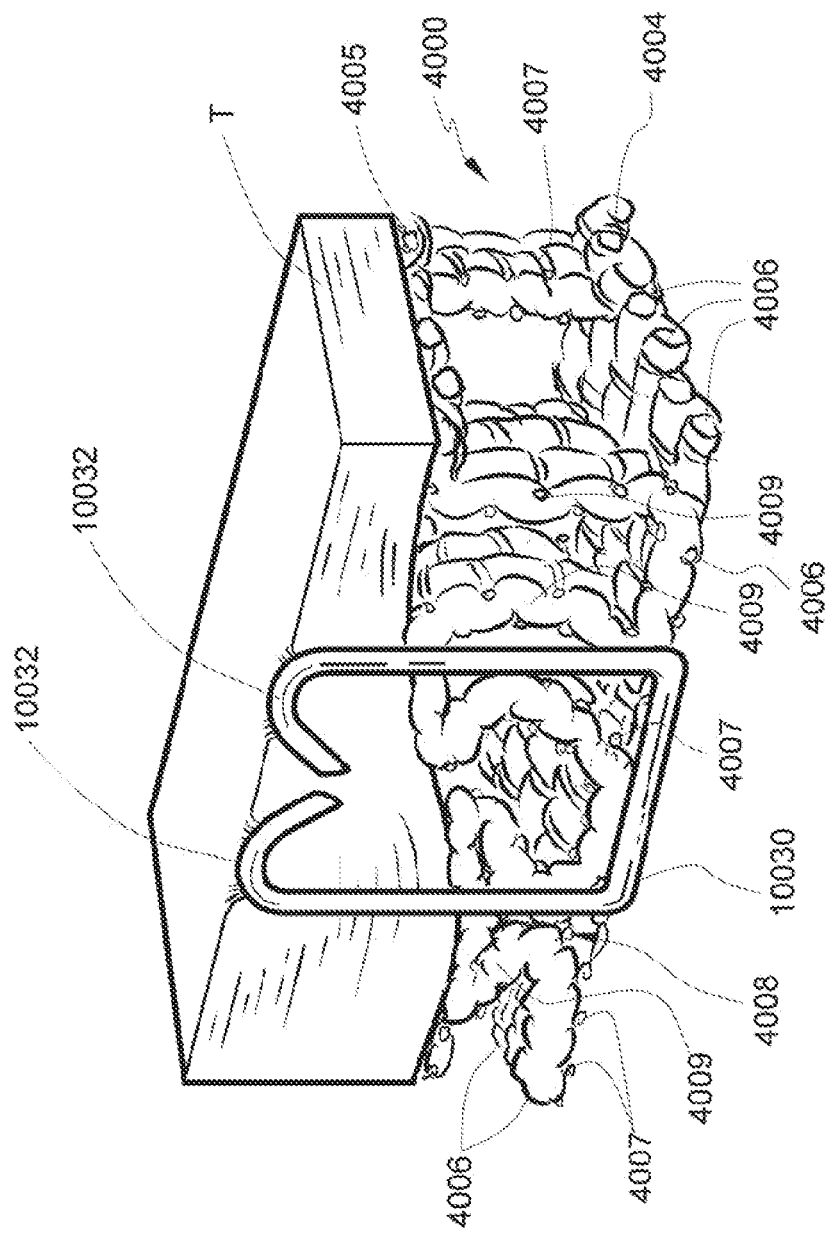
FIG. 34 is a partial perspective view of the adjunct of FIG. 33 implanted against tissue by at least one staple.

The walls 4009 define chambers 4008 therebetween. When a load is applied to the layer 4000, the chambers 4008 permit the walls 4009 to flex, deflect, and/or collapse. The amount in which the walls 4009 deflect is dependent on the thickness of the tissue clamped against the layer 4000. When tissue is pressed downwardly onto the layer 4000, the layer 4000 can adapt to the thickness of the tissue pressed against the layer 4000. Stated another way, the layer 4000 can provide local adaptations to local variations in tissue thickness, as illustrated in FIG. 34. In various instances, the walls 4009 define seams in the layer 4000. The seams can be lateral seams and/or longitudinal seams, for example. The arrangement of the seams can control the deflection of the layer 4000.

Further to the above, the layer 4000 comprises structural fibers 4006 and reinforcement fibers 4007. The structural fibers 4006 are arranged to form the bottom portion 4004, the top portion 4005, and the walls 4009. In at least one instance, as illustrated in FIG. 33, the structural fibers 4006 are arranged in longitudinal rows which form longitudinal seams therebetween. The structural fibers 4006 form columns or pillars which extend between and connect the bottom portion 4004 and the top portion 4005. The reinforcement fibers 4007 are interwoven within the bottom portion 4004, the top portion 4005, and/or the walls 4009. In at least one instance, the reinforcement fibers 4007 are knotted, looped, and/or wrapped around the structural fibers 4006. In various instances, the reinforcement fibers 4007 are interlocked with the structural fibers 4006.

The reinforcement fibers 4007 connect the structural fibers 4006 within the walls 4009. The reinforcement fibers 4007 hold or tie the pillars within the walls 4009 together to provide the walls 4009 with desirable structural properties. For instance, walls 4009 having a higher density of the reinforcement fibers 4007 are stronger than walls 4009 having a lower density. Similarly, the density of the reinforcement fibers 4007 within the bottom portion 4004 and/or the top portion 4006 can affect the strength of the portions 4004 and/or 4006.

As a result of the above, the structural pillars within a wall 4009 can flex and move together. Moreover, the structural fiber pillars 4006 within a wall 4009 are supported by the adjacent structural fiber pillars 2006 owing to the reinforcement fibers 4007. As illustrated in FIG. 33, the reinforcement fibers 4007 within one wall 4009 are not directly connected to the reinforcement fibers 4007 in an adjacent wall 4009; however, the reinforcement fibers 4007 in a first wall 4009 can be connected to the reinforcement fibers 4007 in a second wall 4009 via the bottom portion 4004 and/or the top portion 4006. In various alternative embodiments, reinforcement fibers 4007 can directly span between and connect the adjacent walls 4009.

The structural fibers 4006 and the reinforcement fibers 4007 can be attached to each other at knot interfaces. The knot interfaces can comprise any suitable knot type. The type of knot interfaces that are used can affect the stiffness of the layer 4000. For instance, if loose knots are used, the layer 4000 can be less stiff or have a lower modulus of elasticity. Alternatively, if tight knots are used, the layer 4000 can be stiffer or have a higher modulus of elasticity. The layer 4000 can utilize any suitable type, or types, of knots.

Further to the above, the knots between the structural fibers 4006 and the reinforcement fibers 4007 can be utilized to selectively provide different portions of the layer 4000 with different stiffnesses or moduli of elasticity. For instance, the types of knots and/or the frequency of the knots between the structural fibers 4006 and the reinforcement fibers 4007 can be selected to create a first compression zone and a second compression zone. The first compression zone has a first stiffness and the second compression zone has a second stiffness which is greater than the first stiffness. In at least one instance, the first compression zone is aligned with and positioned over a longitudinal slot defined in the deck 12 which is configured to receive a cutting member and the second compression zone is aligned with and positioned over staple cavities defined in the deck 12. Such an arrangement can facilitate the transection of the layer 4000 while providing desirable tissue thickness compensation properties within the staples 10030 that capture the layer 4000 against the tissue. In certain instances, the first compression zone is aligned with a proximal end of the deck 12 and the second compression zone is positioned distally with respect to the first compression zone. In at least one such instance, another first compression zone is positioned distally with respect to the second compression zone. Such an arrangement can facilitate the transection of the layer 4000 at the beginning and at the end of the cutting stroke of the cutting member.

The structural fibers 4006 comprise a first cross-sectional width, or diameter, and the reinforcement fibers 4007 comprise a second cross-sectional width, or diameter, that is different than the first cross-sectional width. As illustrated in FIGS. 33 and 34, the cross-sectional width of the structural fibers 4006 is wider than the cross-sectional width of the reinforcement fibers 4007. In at least one instance, the cross-sectional width of the structural fibers 4006 is twice as wide as the cross-sectional width of the reinforcement fibers 4007, for example.

The structural fibers 4006 are comprised of a first material and the reinforcement fibers 4007 are comprised of a second material which is different than the first material. In at least one embodiment, the structural fibers 4006 are comprised of a first polymeric material and the reinforcement fibers 4007 are comprised of a second polymeric material which has a lower modulus of elasticity than the modulus of elasticity of the first polymeric material. In an alternative embodiment, the structural fibers 4006 are comprised of a first polymeric material and the reinforcement fibers 4007 are comprised of a second polymeric material which has a higher modulus of elasticity than the modulus of elasticity of the first polymeric material. In certain embodiments, the structural fibers 4006 are comprised of more than one polymeric material and/or the reinforcement fibers 4007 are comprised of more than one polymeric material. In at least one such embodiment, the structural fibers 4006 and the reinforcement fibers 4007 have at least one material in common with one another and at least one material not in common.

Figure 35:
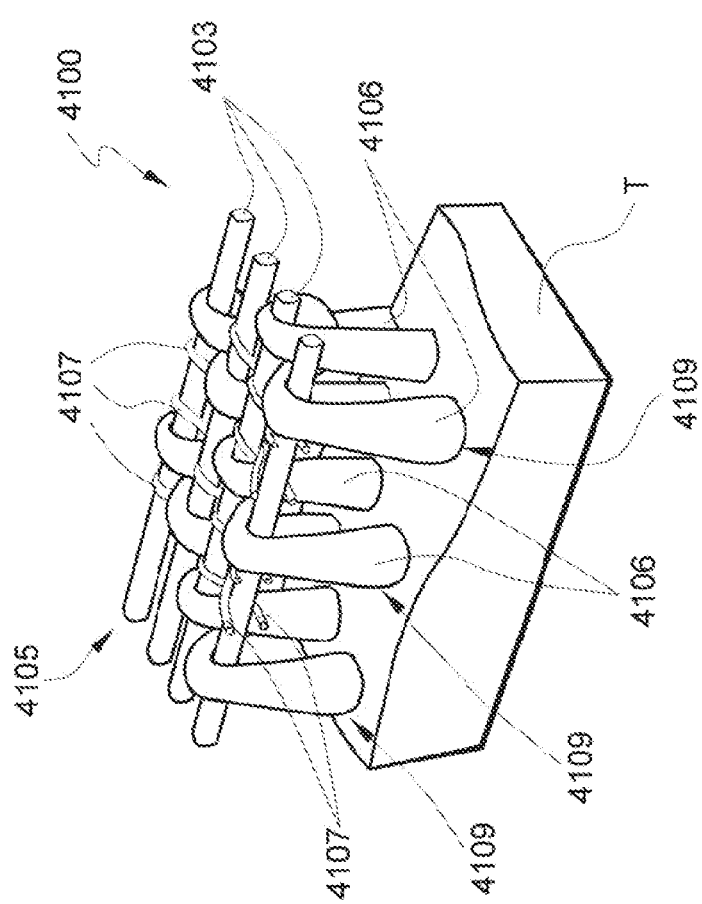
FIG. 35 is a partial perspective view of an implantable adjunct in accordance with at least one embodiment.
Figure 38:
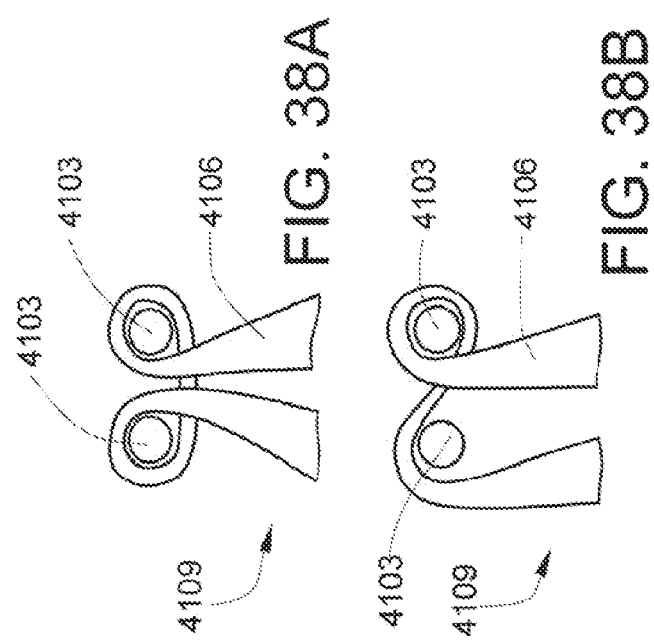
FIG. 38A is a detail view of a loop knot in accordance with at least one embodiment.
FIG. 38B is a detail view of a loop knot utilized by the adjunct of FIG. 35 in accordance with at least one embodiment.

Turning now to FIG. 35, an implantable layer 4100 comprises a top portion 4105 and pillar walls 4109 which support the top portion 4105. The top portion 4105 comprises longitudinal structures or fibers 4103 which are interconnected by structural fibers 4106 which comprise the pillar walls 4109. The structural fibers 4106 are looped, wrapped, and/or knotted around the longitudinal fibers 4103 in any suitable manner. FIGS. 38A and 38B disclose two exemplary manners in which the structural fibers 4106 are interconnected to the longitudinal fibers 4103.

Further to the above, FIG. 38A illustrates a double-looping wrap. A structural fiber 4106 is wrapped around a first longitudinal fiber 4103, bridged over to a second longitudinal fiber 4103, and wrapped around the second longitudinal fiber 4103. The double-looped structural fiber 4106 comprises two standing ends which comprise legs, or pillars, that are part of a pillar wall 4109. Both loops of the structural fiber 4106 comprise closed loops and/or at least one turn; however, alternative embodiments are envisioned in which the loops each include a round turn and/or more than one turn around the longitudinal fibers 4103. The double-looping wrap of FIG. 38A can also be referred to as an inner double-loop. More particularly, the pillars of the structural fiber 4106 both pass through a gap defined between the adjacent first and second longitudinal fibers 4103. In various embodiments, an outer double-loop could be utilized.

Figure 39:
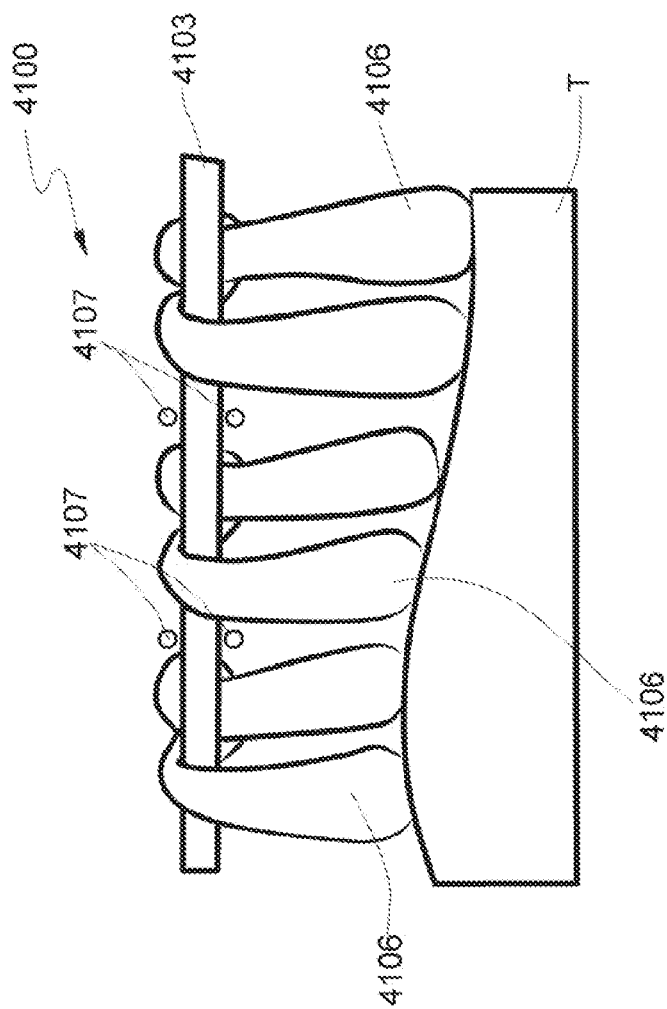
FIG. 39 is a partial elevational view of the implantable adjunct of FIG. 35.

Further to the above, FIGS. 38B and 39 illustrate a structural fiber 4106 wrapped around a first longitudinal fiber 4103, bridged over to a second longitudinal fiber 4103, and wrapped around the second longitudinal fiber 4103. The wrap around the first longitudinal fiber 4103 comprises an open loop; however, a closed loop and/or or one or more turns could be utilized, for example. The wrap around the second longitudinal fiber 4103 comprises a turn; however, a round turn could be utilized, for example. Similar to the above, the structural fiber 4106 of FIG. 38B comprises two standing ends which comprise legs, or pillars, that are part of a pillar wall 4109. The standing ends of the structural fiber 4106 extend through different gaps between the longitudinal fibers 4103.

Figure 36:
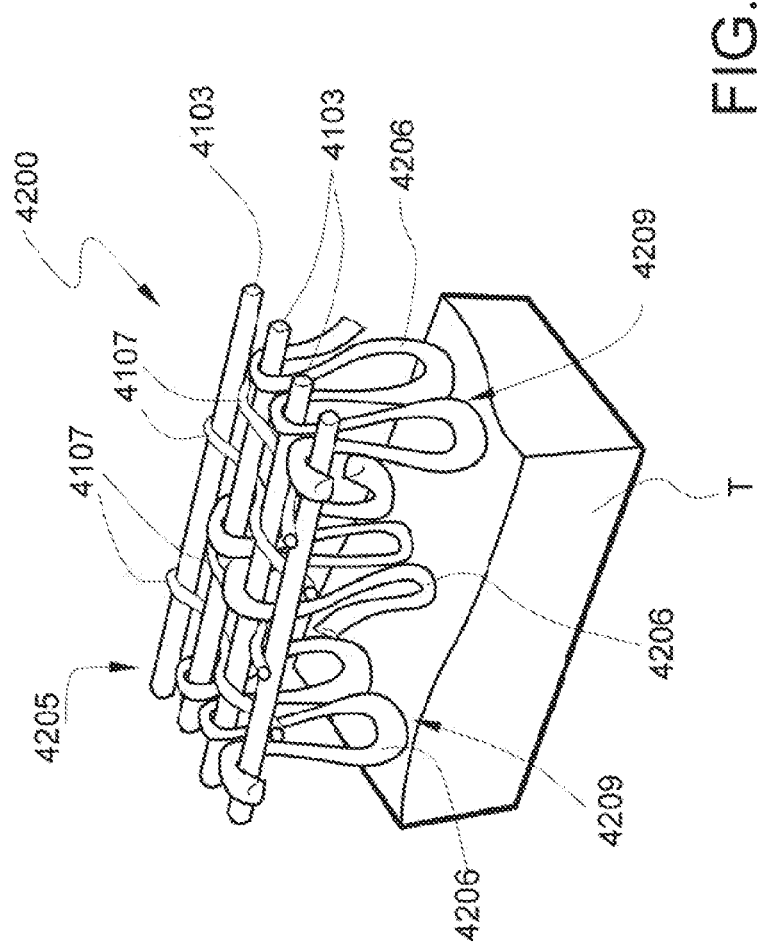
FIG. 36 is a partial perspective view of an implantable adjunct in accordance with at least one alternative embodiment.
Figure 37:
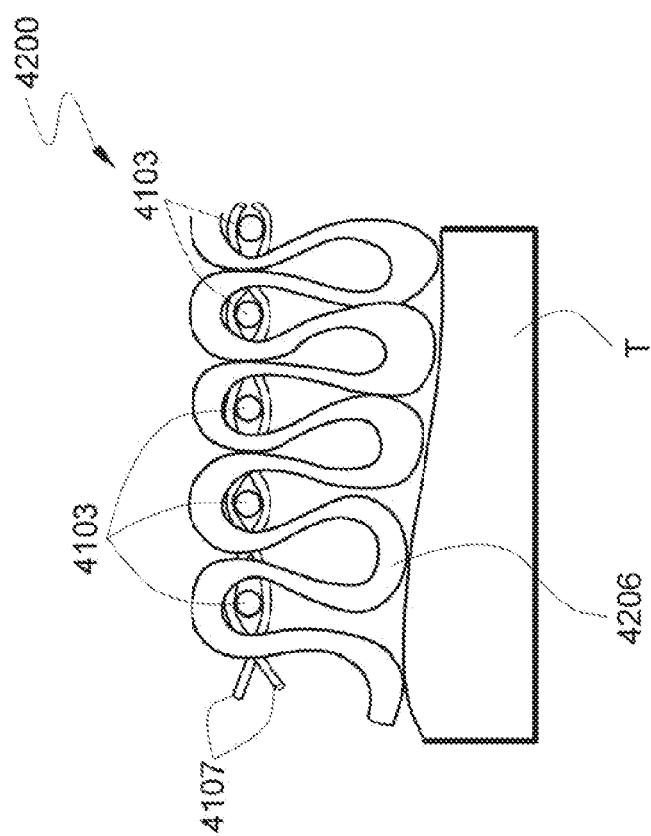
FIG. 37 is a partial elevational view of the implantable adjunct of FIG. 36.

Turning now to FIGS. 36 and 37, a layer 4200 comprises longitudinal structures or fibers 4103. The layer 4200 further comprises structural fibers 4206 and reinforcement fibers 4107. The reinforcement fibers 4107 are interweaved laterally within the longitudinal fibers 4103. The structural fibers 4206 are wrapped around a plurality of the longitudinal fibers 4013 to form walls 4209. As illustrated, each structural fiber 4206 is wrapped around four longitudinal fibers 4103, for example, to form a wall 4209. As a result of the above, each structural fiber 4206 forms several closed ended loop pillars which support the top portion 4205 of the layer 4200. The ends of the structural fibers 4206 do not support the top portion 4205; however, alternative embodiments are envisioned in which the ends of the structural fibers 4206 comprise structural pillars.

The embodiments disclosed herein can provide an organized fiber scaffold with compressive and bending properties interwoven with another scaffold in a manner that forms a larger matrix which has compressive and bending properties in multiple orientations. Such compressive and bending properties can be tuned by adjusting one or more of the characteristics disclosed herein. The walls of the matrix can define an array of macro voids. In various instances, the matrix can have a bi-modal nature with the macro voids defined between walls in the matrix and interstitial spaces defined between the fibers comprising the walls. Such macro voids and interstitial spaces can co-operate to encourage tissue ingrowth and integration of the matrix into the body.

Figure 40:
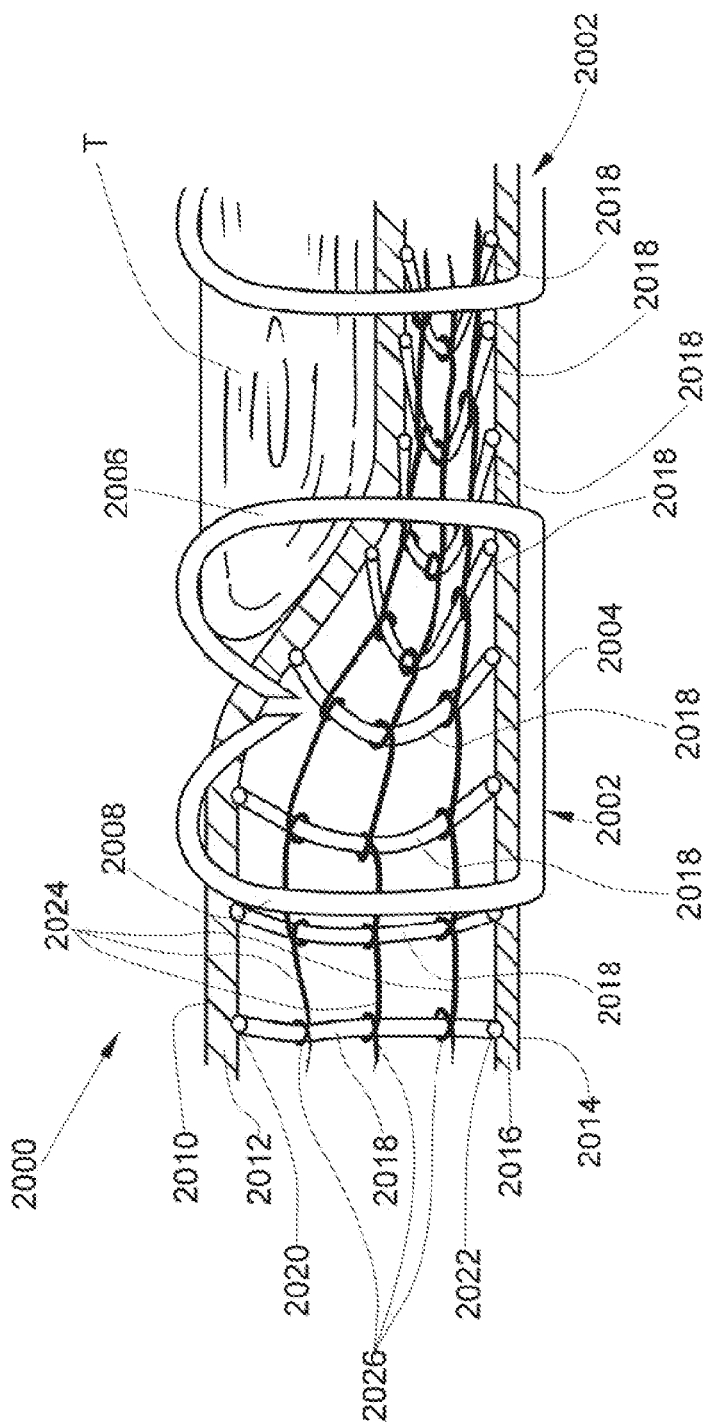
FIG. 40 is a partial cross-sectional view of a compressible adjunct including a plurality of standing fibers in accordance with at least one embodiment described herein.

FIG. 40 illustrates a tissue thickness compensator or compressible adjunct 2000. The compressible adjunct 2000 can be used with numerous devices. In at least one embodiment, the compressible adjunct 2000 can be employed with a surgical stapling and severing instrument 8010. The compressible adjunct 2000 can be attached to a staple cartridge deck 16 of a staple cartridge. Alternatively, in certain instances, the compressible adjunct 2000 can be attached to an anvil 8014.

Referring to FIG. 40, the compressible adjunct 2000 is shown in at least one embodiment partially compressed by tissue T. Staples 2002, which are similar in many respects to the staples 10030, engage the compressible adjunct 2000 when the staples 2002 are fired and formed by a surgical stapling and severing instrument 8010. The formed staples 2002 have a staple base 2004, first staple leg 2006, and second staple leg 2008. In the present embodiment, the first staple leg 2006 engages with the tissue T and compressible adjunct 2000.

The compressible adjunct 2000 includes a first portion 2012 having a tissue contacting interface 2010. When the compressible adjunct 2000 is engaged by tissue T, the tissue contacting interface 2010 contacts and interacts with tissue T. The compressible adjunct 2000 includes a second portion 2016 having a cartridge interface 2014. In the present embodiment, the cartridge interface 2014 can be releasably attached or positioned on or adjacent a staple cartridge deck 16.

The compressible adjunct 2000 includes a middle portion positioned between the first portion 2012 and the second portion 2016. The middle portion includes a plurality of standing fiber pillars 2018 and a plurality of interconnecting fibers 2024. The standing fiber pillars 2018 engage the first portion 2012 at a first portion/standing fiber pillar interface 2020. The standing fiber pillars 2018 engage the second portion 2016 at a second portion/standing fiber pillar interface 2022. The plurality of interconnecting fibers 2024 engage the plurality of standing fiber pillars 2018 at a standing fiber pillar/interconnecting fiber interface 2026.

The first portion 2012 and second portion 2016 comprise various biocompatible materials. The first and second portions 2012, 2016 can also be impregnated or coated with various agents, such as hemostatic agents, antibacterial agents, or antimicrobial agents, which may assist with the recovery time of a patient. The first portion 2012 can have various thicknesses, and material properties. In at least one embodiment, the first portion 2012 can have various densities and resiliencies to provide a first portion 2012 with desirable adaptive properties. Likewise, the second portion 2016 can have various thicknesses and material properties. In at least one embodiment, the second portion 2016 can have various densities and resiliencies to provide a second portion 2016 with desirable adaptive properties.

The standing fiber pillars 2018 comprise one or more biocompatible materials. A standing fiber pillar 2018 can be a resilient fiber with a suitable tensile strength and resiliency. The standing fiber pillar 2018 can comprise uniform material properties and characteristics; or the material properties and characteristics can be varied to provide a compressible adjunct 2100 with desirable adaptive properties. In at least one embodiment, the standing fiber pillars 2018 may be aligned in rows, and each row may have different material properties. When employed with a surgical stapler, the standing fiber pillars 2018 positioned closest to the knife slot of a surgical stapler or nearest an incision can have greater resiliency and require additional force before the standing fiber pillar 2018 are bent or buckled. This may create an increased pressure near the incision which may be beneficial in the treatment of a patient. Alternatively, in certain instances, the standing fiber pillars 2018 positioned closest to the knife slot of a surgical stapler or nearest an incision can have more elasticity and require less force before the standing fiber pillar 2018 are bent or buckled.

In other embodiments, the material properties of the standing fiber pillars 2018 may be varied proximally to distally to provide desirable adaptive properties for the compressible adjunct 2000. The plurality of standing fiber pillars 2018 can include different densities and cross-sectional areas or diameters. When a standing fiber pillar 2018 includes a relatively denser or greater cross-sectional area or diameter, the force required to affect the desired deflection of the standing fiber pillar 2018 may increase. Similarly, when a standing fiber pillar 2018 includes a relatively less dense or smaller cross-sectional area or diameter, the force required to affect the desired deflection may decrease. In addition, the density and cross-sectional areas or diameters of the standing fiber pillars 2018 can be varied to allow the standing fiber pillars 2018 to have different bending moments as forces increase or the compressible adjunct 2000 encounters tissue T with varying thicknesses. In one such embodiment, a standing pillar fiber 2018 can have a greater density in a portion closer to the second portion 2016 and can be less dense in a portion closer to the first portion 2012. This may permit increased resiliency of the compressible adjunct 2000 as additional compression forces are applied, and the force and compression profiles vary regarding displacement and compression of the compressible adjunct 2000

The standing fiber pillars 2018 engage the first portion 2012 at first portion/standing fiber pillar interfaces 2020. The first portion/standing fiber pillar interface 2020 can be one of a friction or resistance relationship where the standing fiber pillars 2018 are not fixably attached to the first portion 2012. In other embodiments, the standing fiber pillars 2018 can be fixably or releasably attached to the first portion 2012 at the first portion/standing fiber pillar interface 2020. In at least one embodiment the standing fiber pillars 2018 can be embedded in the first portion 2012. In alternative embodiments, the standing fiber pillars 2018 can be attached, glued, welded, melted, hooked, woven, knitted, or fastened to the first portion 2012.

The standing fiber pillars 2018 engage the second portion 2016 at second portion/standing fiber pillar interfaces 2022. The second portion/standing fiber pillar interfaces 2022 can be one of a friction or resistance relationship where the standing fiber pillars 2018 are not fixably attached to the second portion 2016. In other embodiments, the standing fiber pillars 2018 can be fixably or releasably attached to the second portion 2016 at the second portion/standing fiber pillar interfaces 2022. In at least one embodiment the standing fiber pillars 2018 can be embedded in the second portion 2016. In alternative embodiments, the standing fiber pillars 2018 can be attached, glued, welded, melted, hooked, woven, knitted, or fastened to the second portion 2016.

The plurality of interconnecting fibers 2024 comprise one or more biocompatible materials. An interconnecting fiber 2024 can be a resilient fiber with a suitable tensile strength and resiliency. The interconnecting fibers 2024 can comprise uniform material properties and characteristics; or the material properties and characteristics can be varied to provide desirable adaptive properties for the compressible adjunct 2000.

In at least one embodiment, the interconnecting fibers 2024 may be aligned in rows and columns to form a matrix and each row and/or column may have different material properties. When employed with a surgical stapler, the interconnecting fibers 2024 positioned closest to the knife slot of the surgical stapler or the incision can be more resilient while the interconnecting fibers 2024 further away from the knife slot can be more elastic. This may create and increased pressure near the incision which may be beneficial in the treatment of the patient. Alternatively, in certain instances, the interconnecting fibers 2024 positioned closest to the knife slot of the surgical stapler or the incision can be more elastic while the interconnecting fibers 2024 further away from the knife slot can be more resilient.

In other embodiments, the material properties of the interconnecting fibers 2024 may be varied proximally to distally depending on a patient's needs. The interconnecting fibers 2024 can include different densities and cross-sectional areas or diameters. When an interconnecting fiber 2024 that includes a relatively denser or greater cross-sectional area or diameter is used, the tension required to affect the desired deflection of the interconnecting fiber 2024 increases. Similarly, when an interconnecting fiber 2024 includes a less dense or smaller cross-section area or diameter, a tension required to affect a desired deflection of the interconnecting fiber 2024 decreases. In addition, the density and cross section areas or diameters of the interconnecting fibers 2024 can be varied between a proximal portion of the staple cartridge 12 and a distal portion of the staple cartridge 12 to allow the interconnecting fibers 2024 to have different physical properties and resiliency when the compressible adjunct 2000 encounters tissue T with varying thicknesses.

The standing fiber pillars 2018 and the interconnecting fibers 2024 engage one another at the standing fiber pillar/interconnecting fiber interfaces 2026. The standing fiber pillar/interconnecting fiber interfaces 2026 can be one of a friction or resistance relationship where the standing fiber pillars 2018 are not fixably attached to the interconnecting fibers 2024. In other embodiments, the standing fiber pillar 2018 can be fixably, releasably, or slidably attached to the interconnecting fibers 2024 at the standing fiber pillar/interconnecting fiber interfaces 2026. In at least one embodiment, the standing fiber pillars 2018 can be embedded in the interconnecting fibers 2024. In alternative embodiments, the standing fiber pillars 2018 can be attached, glued, welded, melted, hooked, woven, looped, or fastened to the interconnecting fibers 2024.

The interconnecting fibers 2024 can also create additional stability for each standing fiber pillar 2018 and for the overall compressible adjunct 2000. Referring again to FIG. 40, the interconnecting fibers 2024 are spaced apart between the first portion 2012 and the second portion 2016. Three interconnecting fibers 2024 are engaged with each standing fiber pillar 2018 spaced substantially equidistance from each other; however, any suitable number of interconnecting fibers 2024 can be employed. In other embodiments, the number of interconnecting fibers 2024 can be increased to increase the stability of the standing fiber pillars 2018 or to increase the resiliency and force required to compress the compressible adjunct 2000. In another embodiment, the spacing and the quantity of interconnecting fibers 2024 can be adjusted to provide a compressible adjunct 2000 with desirable adaptive properties. When the interconnecting fibers 2024 are positioned closer to the second portion 2016, the compressible adjunct 2000 has a higher stiffness in the portion of the compressible adjunct 2000 nearest the second portion 2016 and a lesser stiffness in the portion of the compressible adjunct 2000 nearest the first portion 2012.

Figure 41:
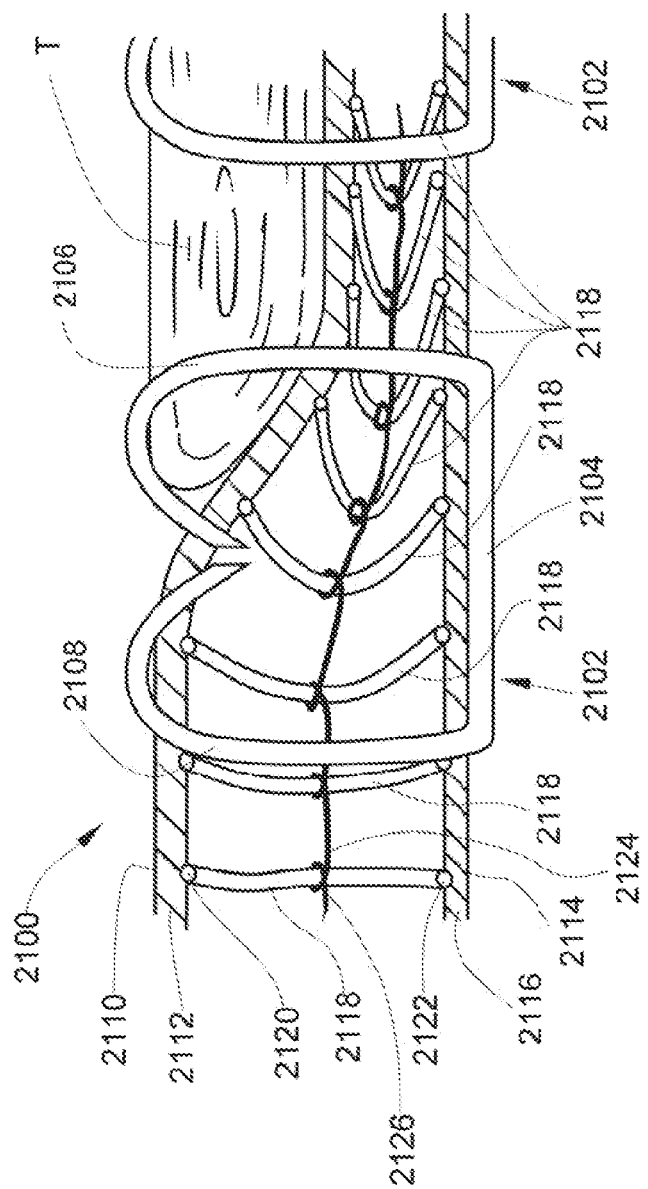
FIG. 41 is a partial cross-sectional view of a compressible adjunct including a plurality of standing fibers in accordance with at least one embodiment described herein.

Referring to FIG. 41, a compressible adjunct 2100 is shown in at least one embodiment partially compressed by tissue T. Staples 2102 engage the compressible adjunct 2100 when the staples 2102 are fired and formed by a surgical stapler. The formed staples 2102 have a staple base 2104, first staple leg 2106, and second staple leg 2108. In the present embodiment, the first staple leg 2106 engages the tissue T and compressible adjunct 2100.

The compressible adjunct 2100 includes a first portion 2112 having a tissue contacting interface 2110. When the compressible adjunct 2100 engages tissue T, the tissue contacting interface 2110 contacts and interacts with tissue T. The compressible adjunct 2100 includes a second portion 2116 having a cartridge interface 2114. The cartridge interface 2114 can be releasably attached or positioned on or adjacent a staple cartridge deck 16.

The compressible adjunct 2100 includes a middle portion positioned between the first portion 2112 and the second portion 2116. The middle portion includes a plurality of standing fiber pillars 2118 and an interconnecting fiber 2124; however any suitable number of interconnecting fibers 2124 can be used. The standing fiber pillars 2118 engage the first portion 2112 at a first portion/standing fiber pillar interface 2120. The standing fiber pillars 2118 engage the second portion 2116 at a second portion/standing fiber pillar interface 2122. The interconnecting fiber 2124 engages the plurality of standing fiber pillars 2118 at a standing fiber pillar/interconnecting fiber interface 2126.

The first portion 2112 and second portion 2116 comprise one or more biocompatible materials. The first and second portions 2112, 2116 can also be impregnated or coated with various agents, such as hemostatic agents, antibacterial agents, or antimicrobial agents, which may assist with the recovery time of a patient. The first portion 2112 can have various thicknesses, and material properties. In at least one embodiment, the first portion 2112 can have various densities and resiliencies to provide a first portion 2112 with desirable adaptive properties. Likewise, the second portion 2116 can have various thicknesses and material properties. In at least one embodiment, the second portion 2116 can have various densities and resiliencies to provide a second portion 2116 with desirable adaptive properties.

The standing fiber pillars 2118 comprise one or more biocompatible materials. A standing fiber pillar 2118 can be a resilient fiber with a suitable tensile strength and resiliency. The standing fiber pillars 2118 can comprise uniform material properties and characteristics; or the material properties and characteristics can be varied to provide a compressible adjunct 2100 with desirable adaptive properties. In at least one embodiment, the standing fiber pillars 2118 may be aligned in rows and each row may have different material properties. When employed with a surgical stapler, the standing fiber pillars 2118 positioned closest to the knife slot of a surgical stapler or nearest an incision can have greater resiliency and require additional force before the standing fiber pillar 2118 are bent or buckled. This may create an increased pressure near the incision which may be beneficial in the treatment of a patient. Alternatively, in certain instances, the standing fiber pillars 2118 positioned closest to the knife slot of a surgical stapler or nearest an incision can have more elasticity and require less force before the standing fiber pillar 2118 are bent or buckled.

In other embodiments, the material properties of the standing fiber pillars 2118 may be varied proximally to distally to provide desirable adaptive properties for the compressible adjunct 2100. The plurality of standing fiber pillars 2118 can include different densities and cross-sectional areas or diameters. When a standing fiber pillar 2118 includes a relatively denser or greater cross-sectional area or diameter, the force required to affect the desired deflection of the standing fiber pillar 2118 may increase. Similarly, when a standing fiber pillar 2118 includes a relatively less dense or smaller cross-sectional area or diameter, the force required to affect the desired deflection may decrease. In addition, the density and cross-sectional areas or diameters of the standing fiber pillars 2118 can be varied to allow the standing fiber pillars 2118 to have different bending moments as forces increase or the compressible adjunct 2100 encounters tissue T with varying thicknesses. In one such embodiment, a standing pillar fiber 2118 can have a greater density in a portion closer to the second portion 2116 and can be less dense in a portion closer to the first portion 2112. This may permit increased resiliency of the compressible adjunct 2100 as additional compression forces are applied, and the force and compression profiles vary regarding displacement and compression of the compressible adjunct 2100.

The standing fiber pillars 2118 engage the first portion 2112 at first portion/standing fiber pillar interfaces 2120. The first portion/standing fiber pillar interface 2120 can be one of a friction or resistance relationship where the standing fiber pillars 2118 are not fixably attached to the first portion 2112. In other embodiments, the standing fiber pillars 2118 can be fixably or releasably attached to the first portion 2112 at the first portion/standing fiber pillar interface 2120. In at least one embodiment the standing fiber pillars 2118 can be embedded in the first portion 2112. In alternative embodiments, the standing fiber pillars 2118 can be attached, glued, welded, melted, hooked, woven, knitted, or fastened to the first portion 2112.

The standing fiber pillars 2118 engage the second portion 2116 at second portion/standing fiber pillar interfaces 2122. The second portion/standing fiber pillar interfaces 2122 can be one of a friction or resistance relationship where the standing fiber pillars 2118 are not fixably attached to the second portion 2116. In other embodiments, the standing fiber pillars 2118 can be fixably or releasably attached to the second portion 2116 at the second portion/standing fiber pillar interfaces 2122. In at least one embodiment the standing fiber pillars 2118 can be embedded in the second portion 2116. In alternative embodiments, the standing fiber pillars 2118 can be attached, glued, welded, melted, hooked, woven, knitted, or fastened to the second portion 2116.

The interconnecting fiber 2124 comprises one or more biocompatible materials. The interconnecting fiber 2124 can be a resilient fiber with a suitable tensile strength and resiliency. The interconnecting fiber 2124 can comprise uniform material properties and characteristics; or the material properties and characteristics can be to provide desirable adaptive properties for the compressible adjunct 2100.

In other embodiments, the material properties of the interconnecting fiber 2124 may be varied proximally to provide desirable adaptive properties. The interconnecting fiber 2124 can include different densities and cross sectional areas.

When an interconnecting fiber 2124 that includes a relatively denser or greater cross-sectional area or diameter is used, the tension required to affect the desired deflection of the interconnecting fiber 2124 increases. Similarly, when an interconnecting fiber 2124 includes a less dense or smaller cross-section area or diameter, a tension required to affect a desired deflection of the interconnecting fiber 2024 decreases. In addition, the density and cross section area or diameter of the interconnecting fiber 2124 can be varied between a proximal portion of the staple cartridge 12 and a distal portion of the staple cartridge 12 to allow the interconnecting fiber 2124 to have different physical properties and resiliency when the compressible adjunct 2100 encounters tissue T with varying thicknesses.

The standing fiber pillars 2118 and the interconnecting fiber 2124 engage one another at the standing fiber pillar/interconnecting fiber interface 2126. The standing fiber pillar/interconnecting fiber interface 2126 can be one of a friction or resistance relationship where the standing fiber pillars 2118 are not fixably attached to the interconnecting fiber 2124. In other embodiments, the standing fiber pillar 2118 can be fixably, releasably, or slidably attached to the interconnecting fiber 2124 at the standing fiber pillar/interconnecting fiber interface 2126. In at least one embodiment, the standing fiber pillars 2118 can be embedded in the interconnecting fiber 2124. In alternative embodiments, the standing fiber pillars 2118 can be attached, glued, welded, melted, hooked, knitted, woven, looped, or fastened to the interconnecting fiber 2124.

The interconnecting fiber 2124 can also create additional stability for the overall compressible adjunct 2100 and for each standing fiber pillar 2118. Referring again to FIG. 41, a single interconnecting fiber 2124 is spaced between the first portion 2112 and the second portion 2116. The single interconnecting fiber 2124 engages each standing fiber pillar 2118 substantially at the midpoint of the standing fiber pillars 2118. In other embodiments, the number of interconnecting fibers 2124 can be increased to increase the stability of the standing fiber pillars 2118 or to increase the resiliency and force required to compress the compressible adjunct 2100. In another embodiment, spacing of interconnecting fiber 2124 can be adjusted to provide a compressible adjunct 2100 with desirable adaptive properties. When the interconnecting fiber 2124 is positioned closer to the second portion 2116, the compressible adjunct 2100 has a higher stiffness in the portion of the compressible adjunct 2100 nearest the second portion 2116 and a lesser stiffness in the portion of the compressible adjunct 2100 nearest the first portion 2112.

Referring to FIG. 41, the interface 2126 can be in the form of slip joints that permit the interconnecting fiber 2124 to slip, move, and/or shift between the standing fiber pillars 2118. This feature allows the standing fiber pillar 2118 to freely bend to different degrees while maintaining a coupling engagement with the other standing fiber pillars 2118 through the slip joint interface defined by the interconnecting fiber 2124.

Figure 42:
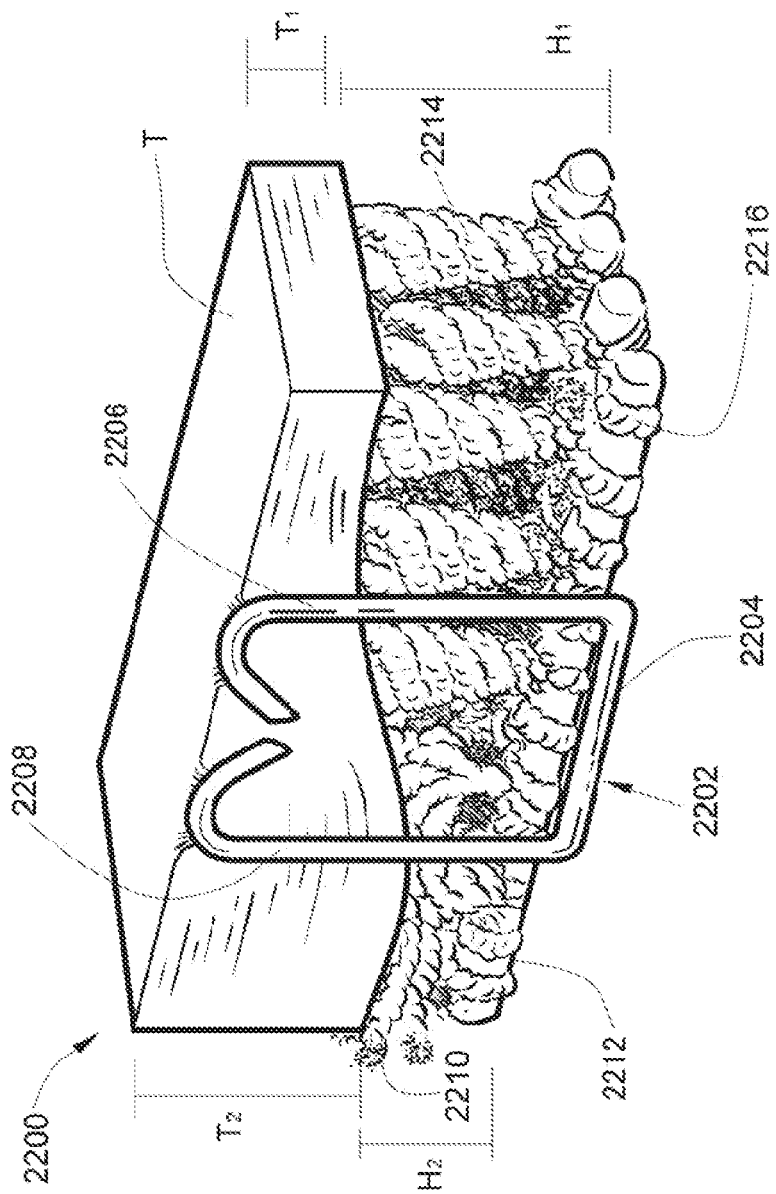
FIG. 42 is a partial perspective view of a compressible adjunct implanted against tissue by at least one staple in accordance with at least one embodiment described herein.

Referring to FIG. 42, a compressible adjunct 2200 is depicted. The compressible adjunct 2200 is engaged with tissue T having various tissue thicknesses. Tissue T has a first tissue thickness T1 and a second tissue thickness T2. At least one Staple 2202 engages the compressible adjunct 2200. The staple 2202 has a staple base 2204, and a first staple leg 2206 and a second staple leg 2208 extending from the staple base 2204. The staple 2202 is formed and a portion of the first staple leg 2206 and second staple leg 2208 engage tissue T and the compressible adjunct 2200.

The compressible adjunct 2200 includes a tissue contacting interface 2210 configured to interact with adjacent tissue T. The compressible adjunct 2200 can be used with various surgical procedures and can be employed in surgical staplers or staple cartridges. The compressible adjunct 2200 includes a cartridge interface 2214 that can rest or be fixably attached to a deck 16 of a staple cartridge 12. The compressible adjunct 2200 can include a plurality of standing fiber support portions 2214 and a compressible adjunct base portion 2216. The plurality of standing fiber support portions 2214 can extend from the compressible adjunct base portion 2216.

The compressible adjunct 2200 is engaged with tissue T having various thicknesses, T1, T2. In response to the tissue thicknesses, the compressible adjunct 2200 is compressed to a first compressed height H1 and a second compressed height H2. In the present embodiment, the compressible adjunct 2200 is responsive and conforming regarding tissue T having varying thicknesses. The compressible adjunct 2200 comprises one or more biocompatible materials.

The standing fiber support portions 2214 can be adapted and configured to have various material properties. The standing fiber support portions 2214 can have various densities, cross section areas and diameters, and porosities. The standing fiber support portions 2214 can include multiple woven or twisted fibers in each standing fiber support portion 2214. These individual fibers can have various densities, cross section areas and diameters, and porosities. Each standing fiber support portion 2214 contains at least two twisted fibers and is fixably attached to the compressible adjunct base portion 2214. Alternatively, the standing fiber support portions 2214 can be releasably or slidably attached to the compressible adjunct base portion 2216. In at least one embodiment, the standing fiber support portions 2214 can be embedded in the compressible adjunct base portion 2216. In alternative embodiments, the standing fiber support portions 2214 can be attached, glued, welded, melted, hooked, woven, knitted, looped, or fastened to the compressible adjunct base portion 2216.

In at least one embodiment, each standing fiber support portion 2214 can include at least two fibers twisted or mated together. The twisted fibers can be adjusted to affect the desired resiliency and compressibility of the compressible adjunct 2200. In at least one embodiment, the fibers of the standing fiber support portion 2214 can be more tightly twisted or wound at a portion of the standing fiber support portion 2214 near the compressible adjunct base portion 2216. Similarly, the fibers of the standing fiber support portion 2214 can be more loosely twisted or wound at a portion of the standing fiber support portion 2214 near the tissue contacting interface 2210. The variable tightness of the fibers of the standing fiber support portions 2214 permits different compressibility of the compressible adjunct 2200. In another embodiment, the fibers of the standing fiber support portions 2214 can be configured to untwist or unwind when the compressible adjunct 2200 encounters tissue having a greater thickness or the standing fiber support portions 2214 encounter greater resistance.

In another embodiment, the axial strength of the standing fiber support portions 2214 can be adjusted and adapted to provide desirable adaptive properties for the compressible adjunct 2200. The standing fiber support portions 2214 can also create a dynamic system where the fibers of the standing fiber support portions 2214 may unravel closer to the tissue contacting interface 2210 and compress near the compressible adjunct base portion 2216. The dynamic system permits the compressible adjunct 2200 to dynamically interact with tissue having varying thicknesses. When the standing fiber support portions 2214 engage a portion of tissue having a greater thickness, they can adaptively adjust to permit greater compressibility of the compressible adjunct 2200. Where the standing fiber support portions 2214 engage a portion of tissue having a thinner thickness, the compressible adjunct 2200 can remain more rigid to compensate for the varying tissue thickness. The dynamic ability to adjust to tissue having varying thicknesses helps facilitate proper staple formation and compression to secure the engaged tissue T.

Figure 43:
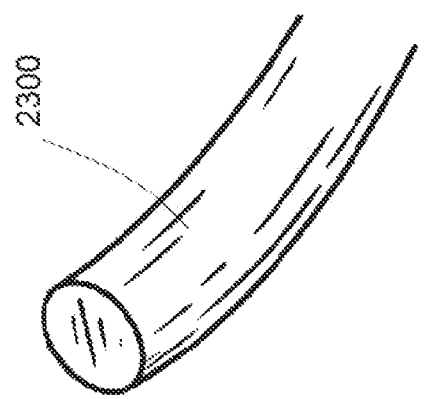
FIG. 43 is a partial perspective view of a fiber in accordance with at least one embodiment described herein.

Referring to FIG. 43, a fiber 2300 is depicted. The fiber 2300 can have various material and physical properties and can be made to different shapes, sizes and lengths. As illustrated in FIG. 43, the fiber 2300 comprises a cylindrical, or at least substantially cylindrical, shape. In other embodiments, the fiber 2300 may have a square, rectangular, oval, octagonal, or any other transverse cross-sectional shape. The fiber 2300 can be flexible and elastic and can be used in manufacturing various compressible adjuncts of the present disclosure. The fiber 2300 comprises one or more biocompatible materials.

The material composition, height, and/or transverse cross-sectional area of the fiber 2300 affect its stiffness or ability to bend under compression. The stiffness of the fiber 2300 can be adjusted to tune the compressibility of a compressible adjunct to one or more desired values.

Figure 44:
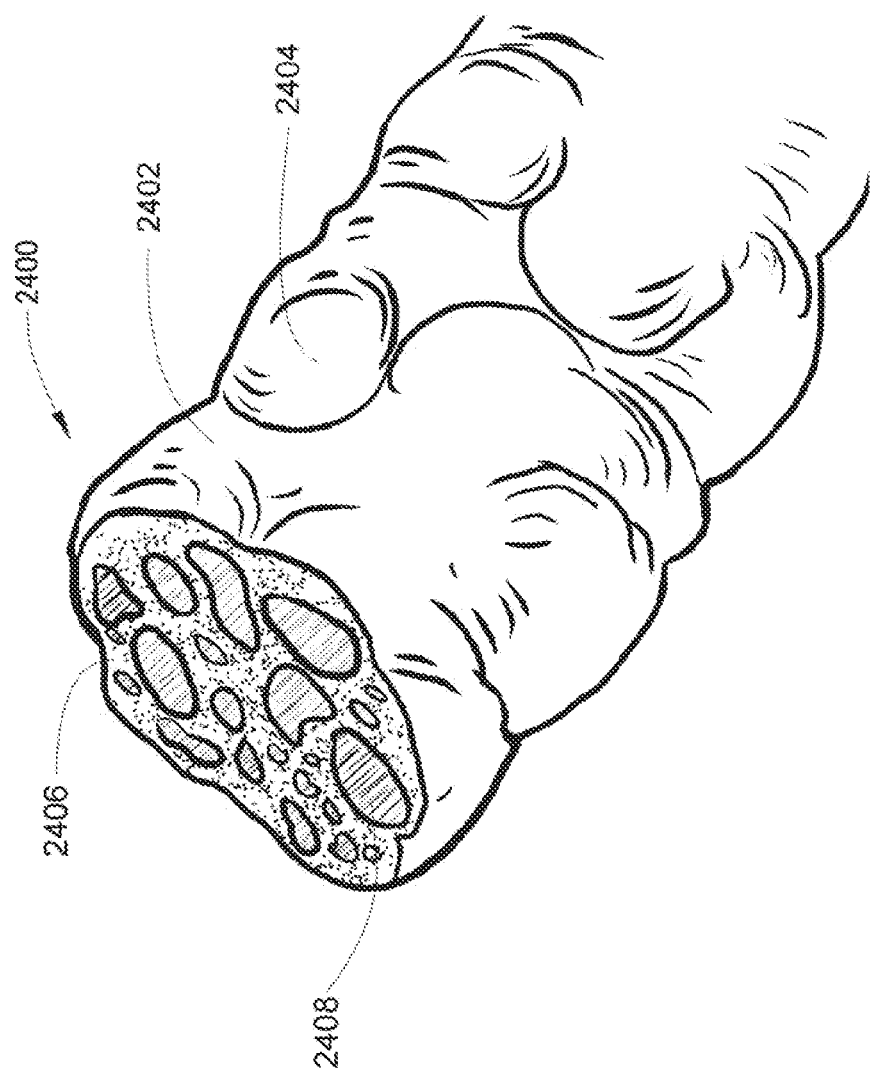
FIG. 44 is a partial perspective view of a fiber in accordance with at least one embodiment described herein.

Referring to FIG. 44, a fiber 2400 is depicted. The fiber 2400 has undergone a gas sorption process. The gas sorption process impregnates a fiber inner portion 2406 of the fiber 2400 with a plurality of fiber inner pores 2408. An outer fiber surface 2402 of the fiber 2400 can also be transformed through the gas sorption process to include a plurality of outer fiber surface pores 2404.

Batch foaming through a gas sorption process includes selecting a substrate or fiber 2400 to be used. The method further includes forcing gas into the fiber 2400 or substrate at elevated pressures. Then the pressure is dropped and, as a result, the subjected fiber 2400 or substrate may expand. The expanded fiber 2400 or substrate can have an increased porosity, a reduced density, and/or increased cross section surface area and diameter. The gas sorption process may be advantageous over other conventional methods as it permits the adjustment and tuning of the material characteristics such as, for example, the stiffness of a fiber 2400 without requiring chemical solvents.

A gas sorption batch foaming process can be applied to various substrates. In at least one embodiment, the gas sorption batch foaming method may be applied to biocompatible polymer films that can be used as an implantable device or compressible adjunct. Gas at elevated pressures can be forced into the polymer films. Then the polymer films can be expanded into a closed cell construct by dropping the pressure. The polymer film can become a compressible closed cell structure without requiring chemical solvents.

Another desirable substrate for the gas sorption process includes melt-blown non-woven constructs. In various instances, a melt blowing process comprises extruding a molten polymer through orifices, and attenuating the extrudates into fibers by action of a high-temperature/high-speed gas that blows the molten polymer from near the orifices onto a conveyer or a take-up screen to form fibrous non-woven constructs.

The melt-blown non-woven constructs rapidly increase in stiffness as they increase in thickness. In certain instances, a compressible adjunct with a greater thickness is desired without the accompanying increase in stiffness. This presents a limitation of the melt blowing process. In certain instances, a compressible adjunct with a greater thickness and suitable stiffness can be obtained using chemical solvents.

Figure 45:
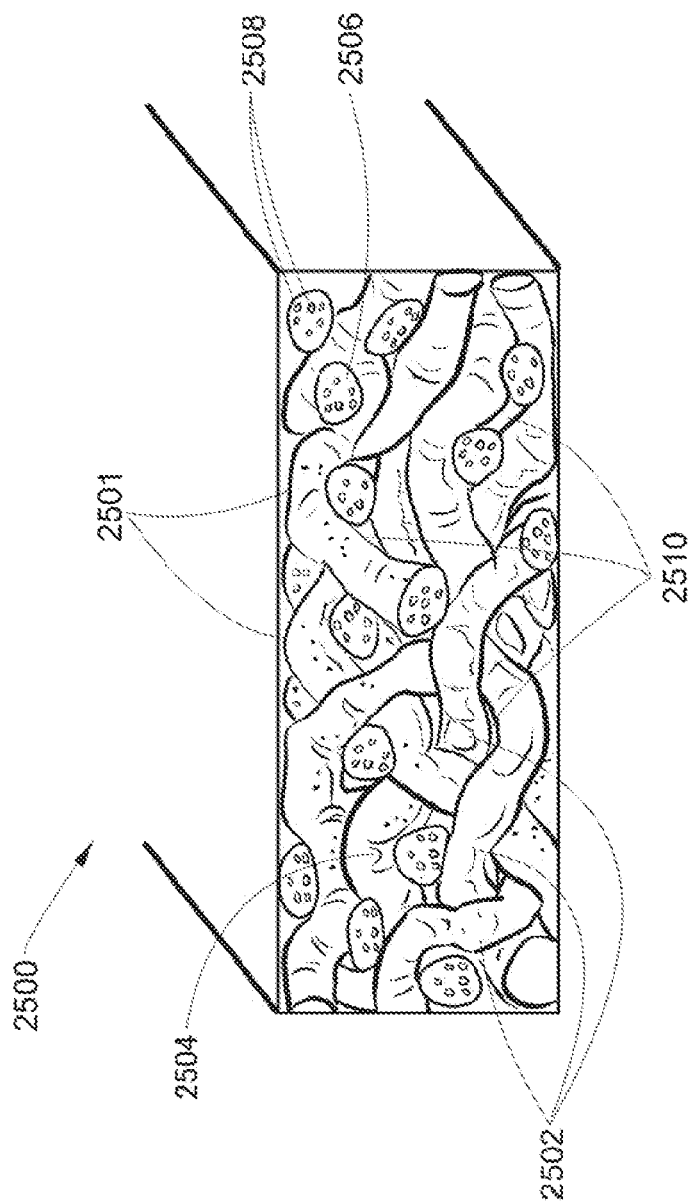
FIG. 45 is a partial perspective view of a compressible adjunct in accordance with at least one embodiment described herein.

Referring to FIG. 45, a compressible adjunct 2500 comprising a greater thickness and suitable stiffness is produced without resorting to chemical solvents. The compressible adjunct 2500 is made through a melt blowing process that yields a melt-blown non-woven intermediate substrate with a plurality of fibers 2501. The melt-blown non-woven intermediate substrate is further processed by a gas sorption process to yield a suitable stiffness. By further processing the melt-blown non-woven substrate through a gas sorption process, the intermediate substrate can be expanded and the density, compressibility, and/or porosity can be adjusted to desired parameters.

The melt-blown non-woven intermediate substrate is produced using a melt blowing process. Other suitable techniques can be employed to produce a suitable substrate for the gas sorption process. In at least one instance, an electrospinning process can be used. In at least one instance, a substrate can be produced by knitting, weaving, or any other suitable process.

One or more of the compressible adjuncts of the present disclosure can be modified by a gas sorption process to adjust their densities, compressibilities, and/or porosities to desired parameters. Various pillars, spacer fibers, standing fibers, and/or looping members of the compressible adjuncts of the present disclosure can be modified by a gas sorption process to adjust their densities, compressibilities, and/or porosities to desired parameters.

Referring to FIG. 45, the gas sorption process may cause outer fiber surfaces 2502 to form outer fiber surface pores 2504. In addition, the gas sorption process can impregnate a fiber inner portion 2506 with a plurality of fiber inner pores 2508. Through the gas sorption process, the intermediate substrate can be expanded in volume while decreasing the density and increasing the porosity of the substrate. Some potential benefits of the combination process may include greater tissue ingrowth into a compressible adjunct 2500 due to the greater porosity achieved by combining the melt blowing process and the gas sorption process. The compressible adjunct 2500, as illustrated in FIG. 45, includes a plurality of pores 2510 generated between the fibers 2501 in the melt blowing process in addition to the pores generated by the gas sorption process within the individual fibers 2501.

Once the compressible adjunct 2500 is formed to the desirable characteristics, further processing may be done. In at least one embodiment, multiple compressible adjuncts 2500 may be layered to increase the thickness of the overall construct or add different material characteristics. In at least one embodiment, compressible adjuncts 2500 made of different materials or of different porosities and densities may be used. In one example, the density and porosity nearer a tissue interface may be greater to allow greater tissue ingrowth. Multiple compressible adjuncts can be attached through melting, fastening, gluing, knitting, weaving, hooking, and other attachment techniques.

The compressible adjunct 2500 can be further enhanced through coating or embedding the compressible adjunct 2500 with various substances. In at least one embodiment, it may be beneficial to coat or impregnate the compressible adjunct 2500 with hemostatic agents, antibacterial agents, or antimicrobial agents.

Various embodiments are disclosed including adjuncts attached to and/or positioned on a staple cartridge. It should be understood that such teachings are applicable to embodiments in which an adjunct is attached to and/or positioned on an anvil of a surgical instrument. In fact, embodiments are envisioned in which a first adjunct is attached to and/or positioned on a cartridge and a second adjunct is attached to and/or positioned on an anvil.

The compressible adjuncts of the present disclosure can be positioned against a cartridge deck of a staple cartridge such as, for example, the cartridge deck 16 of the staple cartridge 12. In at least one instance, a compressible adjunct can be positioned against a cartridge deck of a staple cartridge prior to loading the staple cartridge onto a surgical instrument such as, for example, the surgical stapling and severing instrument 8010 (FIG. 1). Alternatively, a compressible adjunct can be positioned against a cartridge deck of a staple cartridge after the staple cartridge has been loaded into the surgical stapling and severing instrument. A loading unit can be employed to deposit a compressible adjunct onto the cartridge deck of the staple cartridge. The loading unit may include various attachment features and/or placement features for manipulating and positioning the compressible adjunct against the cartridge deck. Once the compressible adjunct is correctly positioned against the cartridge deck, the loading unit can release the compressible adjunct.

Further to the above, a compressible adjunct can be positioned against a cartridge deck without attachment to the staple cartridge. Alternatively, a compressible adjunct can be attached to the staple cartridge prior to or after the staple cartridge is loaded into the surgical stapling and severing instrument. For example, the compressible adjunct can be partially melted onto the cartridge deck then resolidified by cooling which causes the compressible adjunct to bond to the cartridge deck. Various attachment features can also be employed to attach a compressible adjunct to a staple cartridge such as, for example, sutures, straps, barbs, and/or other mechanical attachment mechanisms.

EXAMPLES

Example 1—A compressible adjunct for use with a surgical instrument including a staple cartridge, wherein the compressible adjunct comprises a first biocompatible layer, a second biocompatible layer spaced apart from the first biocompatible layer, and a plurality of supporting pillars extending between the first biocompatible layer and the second biocompatible layer.

Example 2—The compressible adjunct of Example 1, wherein each of the supporting pillars comprises a first end portion attached to the first biocompatible layer and a second end portion attached to the second biocompatible layer.

Example 3—The compressible adjunct of Example 2, wherein the first end portion and the second end portion define a transverse axis intersecting the first biocompatible layer and the second biocompatible layer.

Example 4—The compressible adjunct of Example 3, wherein the transverse axis defines a first angle with the first biocompatible layer, wherein the transverse axis defines a second angle with the second biocompatible layer, and wherein the first angle and the second angle are selected from a range of about 80° to a about 100°.

Example 5—The compressible adjunct of Examples 2, 3, or 4, wherein the first end portion is woven into the first biocompatible layer.

Example 6—The compressible adjunct of Examples 2, 3, 4, or 5, wherein the first end portion is welded to the first biocompatible layer.

Example 7—The compressible adjunct of Examples 1, 2, 3, 4, 5, or 6, wherein the plurality of supporting pillars comprises a first supporting pillar and a second supporting pillar crossing the first supporting pillar.

Example 8—The compressible adjunct of Examples 1, 2, 3, 4, 5, 6, or 7, wherein at least one of the first biocompatible layer and the second biocompatible layer comprises a woven matrix.

Example 9—The compressible adjunct of Examples 1, 2, 3, 4, 5, 6, 7 or 8, wherein at least one of the first biocompatible layer and the second biocompatible layer comprises a knitted matrix.

Example 10—The compressible adjunct of Examples 1, 2, 3, 4, 5, 6, 8 or 9, wherein at least one of the first biocompatible layer and the second biocompatible layer comprises a film.

Example 11—The compressible adjunct of Examples 1, 2, 3, 4, 5, 6, 8, 9, or 10, wherein the second biocompatible layer comprises an outer surface configured to grip tissue.

Example 12—The compressible adjunct of Example 11, wherein the outer surface comprises a plurality of gripping features, and wherein each of the gripping features defines an acute angle with the outer surface.

Example 13—The compressible adjunct of Examples 1, 2, 3, 4, 5, 6, 8, 9, 10, 11, or 12, wherein the first biocompatible layer comprises a greater density than the second biocompatible layer.

Example 14—The compressible adjunct of Examples 1, 2, 3, 4, 5, 6, 8, 9, 10, 11, 12, or 13, further comprising a body portion and an outer edge at least partially surrounding the body portion, wherein the body portion comprises a greater thickness than the outer edge.

Example 15—The compressible adjunct of Example 14, wherein the outer edge is tapered.

Example 16—The compressible adjunct of Examples 14 or 15, wherein the outer edge comprises a first outer edge portion extending from the first biocompatible layer and a second outer edge portion extending from the second biocompatible layer, wherein the first outer edge portion and the second outer edge portion are united into a continuous side portion configured to join the first biocompatible layer and the second biocompatible layer.

Example 17—The compressible adjunct of Examples 1, 2, 3, 4, 5, 6, 8, 9, 10, 11, 12, 13, 14, 15, or 16, further comprising a knife slot configured to receive a knife for cutting tissue captured by the surgical instrument, wherein the knife slot defines two sides, and wherein the knife passes between the two sides.

Example 18—The compressible adjunct of Example 17, further comprising a tether extending between the two sides, wherein the knife is configured to cut the tether to separate the two sides.

Example 19—A staple cartridge assembly for use with a surgical stapling instrument, wherein the staple cartridge assembly comprises a staple cartridge comprising a plurality of staples and a cartridge deck comprising an outer surface. The staple cartridge assembly further comprises a compressible adjunct positionable against the outer surface, wherein the compressible adjunct comprises a tissue-facing biocompatible layer, a deck-facing biocompatible layer positionable against the outer surface, wherein the tissue-facing biocompatible layer is spaced apart from the deck-facing biocompatible layer, and spacer fibers intersecting the tissue-facing biocompatible layer and the deck-facing biocompatible layer, wherein the spacer fibers are configured to lift the tissue-facing biocompatible layer over the deck-facing biocompatible layer.

Example 20—A compressible adjunct for use with a surgical instrument including a staple cartridge, wherein the compressible adjunct comprises a first biocompatible layer, a second biocompatible layer spaced apart from the first biocompatible layer, and an elongate flexible member interconnecting the first biocompatible layer and the second biocompatible layer, wherein the elongate flexible member is configured to form a plurality of supporting structures standing between the first biocompatible layer and the second biocompatible layer.

Example 21—A staple cartridge assembly for use with a surgical stapling instrument, wherein the staple cartridge assembly comprises a staple cartridge comprising a plurality of staples and a cartridge deck. The staple cartridge assembly further comprises a compressible adjunct positionable against the cartridge deck, wherein the staples are deployable into tissue captured against the compressible adjunct, and wherein the compressible adjunct comprises a first biocompatible layer comprising a first portion, a second biocompatible layer comprising a second portion, and crossed spacer fibers extending between the first portion and the second portion.

Example 22—A staple cartridge assembly for use with a surgical stapling instrument, wherein the staple cartridge assembly comprises a staple cartridge comprising a plurality of staples and a cartridge deck. The staple cartridge assembly further comprises a compressible adjunct positionable against the cartridge deck, wherein the staples are deployable into tissue captured against the compressible adjunct, and wherein the compressible adjunct comprises a tissue-facing layer comprising a first bonding node and a second bonding node arranged in a first row with the first bonding node. The compressible adjunct further comprises a deck-facing layer, wherein the tissue-facing layer is spaced apart from the deck-facing layer, and wherein the deck-facing layer comprises a third bonding node vertically aligned with the first bonding node and a fourth bonding node vertically aligned with the second bonding node, wherein the fourth bonding node is arranged in a second row with the third bonding node. The compressible adjunct further comprises a first spacer fiber extending between the first bonding node and the fourth bonding node and a second spacer fiber extending between the second bonding node and the third bonding node, wherein the first spacer fiber crosses the second spacer fiber.

Example 23—The staple cartridge assembly of Example 22, wherein the first row is parallel to the second row.

Example 24—The staple cartridge assembly of Examples 22 or 23, wherein the first row further comprises a fifth bonding node between the first bonding node and the second bonding node.

Example 25—The staple cartridge assembly of Example 24, further comprising a first fiber portion interconnecting the first bonding node and the fifth bonding node.

Example 26—The staple cartridge assembly of Examples 24 or 25, further comprising a second fiber portion interconnecting the second bonding node and the fifth bonding node.

Example 27—The staple cartridge assembly of Examples 22, 23, 24, 25, or 26, wherein the second row further comprises a sixth bonding node between the third bonding node and the fourth bonding node.

Example 28—The staple cartridge assembly of Example 27, further comprising a third fiber portion interconnecting the third bonding node and the sixth bonding node.

Example 29—The staple cartridge assembly of Examples 27 or 28, further comprising a fourth fiber portion interconnecting the fourth bonding node and the sixth bonding node.

Example 30—The staple cartridge assembly of Examples 27, 28, or 29, wherein the fifth bonding node is vertically aligned with the sixth bonding node.

Example 31—A staple cartridge assembly for use with a surgical stapling instrument, wherein the staple cartridge assembly comprises a staple cartridge comprising a plurality of staples and a cartridge deck defining a proximal end and a distal end. The staple cartridge assembly further comprises a compressible adjunct positionable against the cartridge deck, wherein the staples are deployable into tissue captured against the compressible adjunct, and wherein the compressible adjunct comprises a tissue-facing layer comprising a first bonding node and a second bonding node arranged in a first row with the first bonding node. The compressible adjunct further comprises a deck-facing layer, wherein the tissue-facing layer is spaced apart from the deck-facing layer, and wherein the deck-facing layer comprises a third bonding node and a fourth bonding node, wherein the fourth bonding node is arranged in a second row with the third bonding node. The compressible adjunct further comprises a first spacer fiber extending from the first bonding node to the third bonding node, a second spacer fiber extending from the first bonding node toward the deck-facing surface in a proximal direction, and a third spacer fiber extending from the first bonding node toward the deck-facing surface in a distal direction. The compressible adjunct further comprises a fourth spacer fiber extending from the second bonding node to the fourth bonding node.

Example 32—The staple cartridge assembly of Example 31, further comprising a fifth spacer fiber extending from the second bonding node toward the deck-facing surface in the proximal direction.

Example 33—The staple cartridge assembly of Examples 31 or 32, further comprising a sixth spacer fiber extending from the second bonding node toward the deck-facing surface in the distal direction.

Example 34—The staple cartridge assembly of Example 33, wherein the sixth spacer fiber crosses the second spacer fiber.

Example 35—The staple cartridge assembly of Examples 31, 32, 33, or 34, further comprising a seventh spacer fiber extending from the first bonding node to the third bonding node.

Example 36—The staple cartridge assembly of Examples 31, 32, 33, 34, or 35, further comprising an eighth spacer fiber extending from the second bonding node to the fourth bonding node.

Example 37—The staple cartridge assembly of Examples 31, 32, 33, 34, 35, or 36, wherein the first bonding node is vertically aligned with the third bonding node.

Example 38—The staple cartridge assembly of Examples 31, 32, 33, 34, 35, 36, or 37, wherein the second bonding node is vertically aligned with the fourth bonding node.

Example 39—A staple cartridge assembly for use with a surgical stapling instrument, wherein the staple cartridge assembly comprises a staple cartridge comprising a plurality of staples and a cartridge deck defining a proximal end and a distal end. The staple cartridge assembly further comprises a compressible adjunct positionable against the cartridge deck, wherein the staples are deployable into tissue captured against the compressible adjunct, and wherein the compressible adjunct comprises a tissue-facing layer and a deck-facing layer, wherein the tissue-facing layer is spaced apart from the deck-facing layer, and wherein the deck-facing layer comprises an outer surface and an inner surface. The compressible adjunct further comprises a first spacer fiber extending from the tissue-facing layer toward the inner surface, a second spacer fiber extending from the tissue-facing layer toward the inner surface, wherein the first spacer fiber and the second spacer fiber extend through the deck-facing layer, and a loop defined by the first spacer fiber and the second spacer fiber on the outer surface.

Example 40—The staple cartridge assembly of Example 39, wherein the first spacer fiber and the second spacer fiber intersect at the deck-facing layer.

Example 41—The staple cartridge assembly of Examples 39 or 40, further comprising a third spacer fiber extending from the tissue-facing layer, wherein the third spacer fiber intersects the first spacer fiber and the second spacer fiber at the deck-facing layer.

Example 42—A compressible adjunct for use with a surgical instrument including a staple cartridge, wherein the compressible adjunct comprises a biocompatible layer and a plurality of biocompatible looping members protruding from the biocompatible layer. Each of the biocompatible looping members comprises a first end portion attached to the biocompatible layer, a second end portion attached to the biocompatible layer, and an intermediate curved portion extending between the first end portion and the second end portion, wherein the intermediate curved portion is further away from the biocompatible layer than the first end portion and the second end portion.

Example 43—The compressible adjunct of Example 42, further comprising another biocompatible layer spaced apart from the biocompatible layer.

Example 44—The compressible adjunct of Example 43, wherein the plurality of biocompatible looping members is positioned between the biocompatible layer and the another biocompatible layer.

Example 45—The compressible adjunct of Examples 43 or 44, wherein the intermediate curved portion is attached to the another biocompatible layer.

Example 46—The compressible adjunct of Examples 43, 44, or 45, wherein the another biocompatible layer comprises a woven layer.

Example 47—The compressible adjunct of Examples 42, 43, 44, 45, or 46, wherein the biocompatible layer comprises a plurality of tethering islands that are spaced apart from one another, and wherein each of the tethering islands is defined by the first end portion and the second end portion of at least one of the biocompatible looping members.

Example 48—The compressible adjunct of Example 47, wherein the tethering islands are arranged in parallel rows.

Example 49—The compressible adjunct of Examples 42, 43, 44, 45, 46, or 47, wherein each of the biocompatible looping members comprises a wide head portion and narrow neck portion extending between the wide head portion and the biocompatible layer.

Example 50—The compressible adjunct of Examples 42, 43, 44, 45, 46, 47, or 48, wherein each of the biocompatible looping members is comprised of a fiber.

Example 51—The compressible adjunct of Example 50, wherein the fiber is a multifilament fiber.

Example 52—The compressible adjunct of Examples 42, 43, 44, 45, 46, 47, 48, 49, 50, or 51, wherein the biocompatible looping members are configured to bend in a disorganized manner in response to a compression force.

Example 53—The compressible adjunct of Examples 42, 43, 44, 45, 46, 47, 48, 49, 50, or 51, wherein the biocompatible looping members are configured to bend in an organized manner in response to a compression force.

Example 54—A compressible adjunct for use with a surgical instrument including a staple cartridge, wherein the compressible adjunct comprises a first biocompatible layer comprising first fiber loops arranged in a plurality of first rows, a second biocompatible layer spaced apart from the first biocompatible layer, wherein the second biocompatible layer comprises second fiber loops arranged in a plurality of second rows spaced apart from the plurality of first rows, and a pair of first fiber portions extending from each of the first fiber loops toward the second biocompatible layer. The compressible adjunct further comprises a pair of second fiber portions extending from each of the second fiber loops toward the first biocompatible layer.

Example 55—The compressible adjunct of Example 54, wherein the first fiber portions are slanted to favor bending in a first direction in response to a compression force.

Example 56—The compressible adjunct of Example 55, wherein the second fiber portions are slanted to favor bending in the first direction in response to the compression force.

Example 57—The compressible adjunct of Examples 54, 55, or 56, wherein the first fiber portions and the second fiber portions are configured to bend in a disorganized manner in response to a compression force.

Example 58—The compressible adjunct of Examples 54, 55, or 56, wherein the first fiber portions and the second fiber portions are configured to bend in an organized manner in response to a compression force.

Example 59—A staple cartridge assembly for use with a surgical stapling instrument, wherein the staple cartridge assembly comprises a staple cartridge comprising a plurality of staples and a cartridge deck defining a proximal end and a distal end. The staple cartridge assembly further comprises a compressible adjunct positionable against the cartridge deck, wherein the compressible adjunct comprises a first biocompatible layer and a second biocompatible layer spaced apart from the first biocompatible layer. The second biocompatible layer comprises a first fiber loop, a pair of first fiber portions extending from the first fiber loop toward the first biocompatible layer, a second fiber loop proximal to the first fiber loop, wherein the pair of first fiber portions passes through the second fiber loop, and a pair of second fiber portions extending from the second fiber loop toward the first biocompatible layer.

Example 60—The staple cartridge assembly of Example 59, wherein the second biocompatible layer comprises a third fiber loop proximal to the second fiber loop, wherein the pair of second fiber portions passes through the third fiber loop and a pair of third fiber portions extending from the third fiber loop toward the first biocompatible layer.

Example 61—The staple cartridge assembly of Examples 59 or 60, wherein the second layer is a knitted layer.

Example 62—A staple cartridge assembly comprising a cartridge body comprising a deck and a plurality of staple cavities defined in the deck, a plurality of staples removably stored in the staple cavities, and an implantable layer positioned over the staple cavities, wherein the implantable layer comprises structural fibers weaved into a top surface, a bottom surface, and pillar walls extending between the top surface and the bottom surface and reinforcement fibers interwoven within the pillar walls.

Example 63—The staple cartridge assembly of Example 62, wherein the reinforcement fibers are interwoven within the top surface and the bottom surface.

Example 64—The staple cartridge assembly of Examples 62 or 63, wherein the reinforcement fibers are looped around the structural fibers.

Example 65—The staple cartridge assembly of Examples 62, 63, or 64, wherein the implantable layer comprises a first compression zone comprising a first density of loops between the reinforcement fibers and the structural fibers and a second compression zone comprises a second density of loops between the reinforcement fibers and the structural fibers, wherein the second density is greater than the first density.

Example 66—The staple cartridge assembly of Example 65, wherein the cartridge body further comprises a longitudinal slot configured to receive a cutting member, wherein the first compression zone is aligned with the longitudinal slot, and wherein the second compression zone is aligned with the staple cavities.

Example 67—The staple cartridge assembly of Examples 62, 63, 64, 65, or 66, wherein the cartridge body comprises a proximal end and a distal end, wherein the first compression zone is aligned with the proximal end, and wherein the second compression zone is positioned distally with respect to the first compression zone.

Example 68—The staple cartridge assembly of Examples 62, 63, 64, 65, 66, or 67, wherein the cartridge body further comprises a longitudinal slot configured to receive a cutting member, and wherein the pillar walls extend across the longitudinal slot.

Example 69—The staple cartridge assembly of Examples 62, 63, 64, 65, 66, 67, or 68, wherein each the structural fiber comprises a longitudinal seam that extends between a proximal end and a distal end of the cartridge body.

Example 70—The staple cartridge assembly of Examples 62, 63, 64, 65, 66, 67, 68, or 69, wherein each the reinforcement fiber comprises a lateral seam that extends through a pillar wall.

Example 71—The staple cartridge assembly of Examples 62, 63, 64, 65, 66, 67, 68, 69, or 70, wherein the structural fibers are comprised of a first material, and wherein the reinforcement fibers are comprised of a second material which is different than the first material.

Example 72—The staple cartridge assembly of Examples 62, 63, 64, 65, 66, 67, 68, 69, 70, or 71, wherein the reinforcement fibers are knotted with the structural fibers.

Example 73—The staple cartridge assembly of Examples 62, 63, 64, 65, 66, 67, 68, 69, 70, 71, or 72, wherein the implantable layer comprises a first compression zone comprising a first density of knots between the reinforcement fibers and the structural fibers and a second compression zone comprises a second density of knots between the reinforcement fibers and the structural fibers, wherein the second density is greater than the first density.

Example 74—A staple cartridge assembly comprising a cartridge body comprising a deck and a plurality of staple cavities defined in the deck, a plurality of staples stored in the staple cavities, and an implantable layer positioned over the staple cavities, wherein the implantable layer comprises interconnected structural walls comprised of interwoven fibers and pockets defined between the structural walls.

Example 75—The staple cartridge assembly of Example 74, wherein the structural walls are comprised of structural fibers weaved into a top surface, a bottom surface, and pillar walls extending between the top surface and the bottom surface and reinforcement fibers interwoven within the pillar walls.

Example 76—The staple cartridge assembly of Example 75, wherein the reinforcement fibers are looped around the structural fibers.

Example 77—The staple cartridge assembly of Examples 75 or 76, wherein the implantable layer comprises a first compression zone comprising a first density of loops between the reinforcement fibers and the structural fibers and a second compression zone comprises a second density of loops between the reinforcement fibers and the structural fibers, wherein the second density is greater than the first density.

Example 78—The staple cartridge assembly of Example 77, wherein the cartridge body further comprises a longitudinal slot configured to receive a cutting member, wherein the first compression zone is aligned with the longitudinal slot, and wherein the second compression zone is aligned with the staple cavities.

Example 79—The staple cartridge assembly of Examples 77 or 78, wherein the cartridge body comprises a proximal end and a distal end, wherein the first compression zone is aligned with the proximal end, and wherein the second compression zone is positioned distally with respect to the first compression zone.

Example 80—The staple cartridge assembly of Examples 75, 76, 77, 78, or 79, wherein the structural fibers are comprised of a first material, and wherein the reinforcement fibers are comprised of a second material which is different than the first material.

Example 81—The staple cartridge assembly of Examples 75, 76, 77, 78, 79, or 80, wherein the cartridge body further comprises a longitudinal slot configured to receive a cutting member, and wherein the structural walls extend across the longitudinal slot.

Example 82—The staple cartridge assembly of Examples 75, 76, 77, 78, 79, 80, or 81, wherein the structural walls comprise longitudinal seams that extend between a proximal end and a distal end of the cartridge body.

Example 83—The staple cartridge assembly of Example 82, wherein the structural walls further comprise lateral seams that extend transversely to the longitudinal seams.

Example 84—A staple cartridge assembly comprising a cartridge body comprising a deck and a plurality of staple cavities defined in the deck, a plurality of staples stored in the staple cavities, and an implantable layer positioned over the staple cavities, wherein the implantable layer comprises a top portion, a bottom portion, and walls interwoven between the top portion and the bottom portion.

Example 85—A compressible adjunct comprising a first portion, a second portion, and a middle portion, wherein the middle portion is disposed between the first portion and the second portion, and wherein the middle portion comprises a first pillar, a second pillar, wherein the first pillar and the second pillar extend substantially between the first portion and the second portion, and an interconnecting member, wherein the interconnecting member is configured to engage at least the first pillar and the second pillar, wherein when the compressible adjunct is compressed by a force, the first pillar is configured to deflect a first deflection and the second pillar is configured to deflect a second deflection, and wherein the first deflection differs from the second deflection.

Example 86—The compressible adjunct of Example 85, wherein the interconnecting member fixably engages the first pillar and the second pillar.

Example 87—The compressible adjunct of Examples 85 or 86, wherein the interconnecting member slidingly engages the first pillar and the second pillar.

Example 88—The compressible adjunct of Examples 85, 86, or 87, wherein the first pillar comprises a first cross sectional diameter, wherein the second pillar comprises a second cross sectional diameter, and wherein the first diameter differs from the second diameter.

Example 89—The compressible adjunct of Example 88, wherein the first cross sectional diameter is greater than the second cross sectional diameter, and wherein the second deflection is greater than the first deflection.

Example 90—The compressible adjunct of Examples 85, 86, 87, 88, or 89, wherein the first pillar comprises a first density, wherein the second pillar comprises a second density, and wherein the first density differs from the second density.

Example 91—The compressible adjunct of Example 90, wherein the first density is greater than the second density, and wherein the second deflection is greater than the first deflection.

Example 92—The compressible adjunct of Examples 85, 86, 87, 88, 89, 90, or 91, wherein the first pillar comprises a first cross sectional diameter, wherein the second pillar comprises a second cross sectional diameter, wherein the interconnecting member comprises a third cross sectional diameter, and wherein the first cross sectional diameter and the second cross sectional diameter differ from the third cross sectional diameter.

Example 93—The compressible adjunct of Examples 85, 86, 87, 88, 89, 90, 91, or 92, wherein the first pillar comprises a first density, wherein the second pillar comprises a second density, wherein the interconnecting member comprises a third density, and wherein the first density and the second density differ from the third density.

Example 94—The compressible adjunct of Examples 85, 86, 87, 88, 89, 90, 91, 92, or 93, wherein the first pillar comprises a first end, a second end, and a middle section, wherein the first end engages the first portion, wherein the second end engages the second portion, and wherein the interconnecting member engages the middle section.

Example 95—A compressible adjunct comprising a base portion and a plurality of pillars, wherein the plurality of pillars comprises a first support comprising a first pillar, and a second pillar, wherein the first pillar and the second pillar engage the base portion, and wherein the first pillar and the second pillar are interconnected. The plurality of pillars further comprises a second support comprising a third pillar and a fourth pillar, wherein the third pillar and the fourth pillar engage the base portion, wherein the third pillar and the fourth pillar are interconnected, wherein when the compressible adjunct is compressed by a force, the first support is configured to deflect a first deflection and the second support is configured to deflect a second deflection, and wherein the first deflection differs from the second deflection.

Example 96—The compressible adjunct of Example 95, wherein the first support comprises a first material, and wherein the second support comprises a second material, and wherein the first material differs from the second material.

Example 97—The compressible adjunct of Examples 95 or 96, wherein the first support has a first average density, and wherein the second support has a second average density, and wherein the first average density differs from the second average density.

Example 98—The compressible adjunct of Example 97, wherein the first average density is greater than the second average density, and wherein the second deflection is greater than the first deflection.

Example 99—The compressible adjunct of Examples 95, 96, 97, or 98, wherein the first pillar comprises a first cross sectional diameter, wherein the second pillar comprises a second cross sectional diameter, and wherein the first diameter differs from the second diameter.

Example 100—The compressible adjunct of Examples 95, 96, 97, 98, or 99, wherein the first pillar comprises a first cross sectional diameter, wherein the second pillar comprises a second cross sectional diameter, wherein the third pillar comprises a third cross sectional diameter, and wherein the fourth pillar comprises a fourth cross sectional diameter.

Example 101—The compressible adjunct of Example 100, wherein the first diameter differs from the third diameter, and wherein the second diameter differs from the fourth diameter.

Example 102—The compressible adjunct of Examples 95, 96, 97, 98, 99, 100, or 101, wherein the first support comprises an first average height, wherein the second support comprises an second average height, and wherein the first height differs from the second height.

Example 103—The compressible adjunct of Example 102, wherein the first average height is greater than the second average height and the first deflection is greater than the second deflection.

Example 104—The compressible adjunct of Examples 95, 96, 97, 98, 99, 100, 101, 102, or 103, wherein the first pillar and the second pillar are woven together, and wherein when the compressible adjunct is compressed, the first pillar and the second pillar are configured to partially unwind.

Example 105—A method of producing a fibrous compressible construct with a desired thickness, wherein the method comprises the steps of, one, producing a biocompatible melt-blown non-woven substrate that comprises a thickness lesser than the desired thickness, wherein the biocompatible melt-blown non-woven substrate comprises a plurality of fibers and, two, applying a gas sorption process to the biocompatible melt-blown non-woven substrate to modify the thickness to the desired thickness.

Example 106—The method of Example 105, wherein the step of applying the gas sorption process comprises applying a high pressure gas to the biocompatible melt-blown non-woven substrate.

Example 107—The method of Examples 105 or 106, wherein the step of producing the biocompatible melt-blown non-woven substrate comprises extruding a polymer, attenuating the extrudates into fibers by action of a high-temperature and high-speed gas, and collecting the fibers to form a fibrous non-woven fabric.

Example 108—The method of Examples 105, 106, or 107, wherein the step of applying a gas sorption process comprises, one, applying a high pressure gas to the biocompatible melt-blown non-woven substrate and, two, reducing the pressure of the gas.

In various circumstances, one or more of the compressible adjuncts of the present disclosure is comprised of one or more biocompatible materials. A compressible adjunct may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer. In various circumstances, the polymeric composition may comprise a porous structure with a uniform pore morphology or a gradient pore morphology (i.e. small pores gradually increasing in size to large pores across the thickness of the foam in one direction).

In various circumstances, a compressible adjunct has a porous morphology which exhibits a gradient structure such as, for example, small pores on one surface and larger pores on the other surface. Such morphology could be more optimal for tissue in-growth or hemostatic behavior. Further, the gradient could be also compositional with a varying bio-absorption profile. A short term absorption profile may be preferred to address hemostasis while a long term absorption profile may address better tissue healing without leakages.

In various circumstances, the polymeric composition may comprise a pharmaceutically active agent. The polymeric composition may release a therapeutically effective amount of the pharmaceutically active agent. In various circumstances, the pharmaceutically active agent may be released as the polymeric composition is desorbed/absorbed. In various circumstances, the pharmaceutically active agent may be released into fluid, such as, for example, blood, passing over or through the polymeric composition.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A staple cartridge assembly for use with a surgical stapling instrument, wherein the staple cartridge assembly comprises:
    a staple cartridge comprising:
        a plurality of staples; and
        a cartridge deck;
    a compressible adjunct positionable against the cartridge deck, wherein the staples are deployable into tissue captured against the compressible adjunct, and wherein the compressible adjunct comprises:
        a tissue-facing layer; and
        a deck-facing layer, wherein the tissue-facing layer is spaced apart from the deck-facing layer; and
    structural cells defined by a plurality of walls, wherein the structural cells are positioned between the tissue-facing layer and the deck-facing layer.

2. The staple cartridge assembly of claim 1, wherein the structural cells are configured to define first openings comprising a first size, wherein the compressible adjunct further comprises second openings comprising a second size different than the first size, and wherein the first openings and second openings cooperate to define a continuous path through the compressible adjunct.

3. The staple cartridge assembly of claim 1, wherein a first subset of the structural cells has a first number of walls, wherein a second subset of the structural cells has a second number of walls that is different from the first number of walls.

4. The staple cartridge assembly of claim 1, wherein each of the plurality of walls comprise a non-uniform thicknesses.

5. The staple cartridge assembly of claim 1, wherein the structural cells include a first structural cell and a second structural cell, wherein the first structural cell is positioned adjacent to the second structural cell, and wherein the first structural cell and second structural cell share at least one wall of the plurality of walls.

6. The staple cartridge assembly of claim 1, wherein each structural cell comprises an initial height, and wherein the initial height is reduced to a compressed height based on a compressive force applied to the compressible adjunct.

7. The staple cartridge assembly of claim 6, wherein the initial height is a first initial height of a first structural cell and the compressed height is a first compressed height of the first structural cell, wherein a second structural cell has a second initial height that is reduced to a second compressed height based on the compressive force applied to the compressible adjunct, and wherein the first compressed height and the second compressed height are different.

8. A staple cartridge assembly for use with a surgical stapling instrument, wherein the staple cartridge assembly comprises:
    a staple cartridge comprising:
        a plurality of staples; and
        a cartridge deck;
    a compressible adjunct positionable against the cartridge deck, wherein the staples are deployable into tissue captured against the compressible adjunct, and wherein the compressible adjunct comprises:
        a first biocompatible layer; and
        a second biocompatible layer, wherein the first biocompatible layer and the second biocompatible layer are configured to define an intermediate portion therebetween; and
    structural cells defined by a plurality of walls, wherein the structural cells extend in the intermediate portion, and wherein the structural cells cause the intermediate portion of the compressible adjunct to be more porous than the first biocompatible layer and the second biocompatible layer.

9. The staple cartridge assembly of claim 8, wherein the structural cells are configured to define first openings comprising a first size, wherein the compressible adjunct further comprises second openings comprising a second size different than the first size, and wherein the first openings and second openings cooperate to define a continuous path through the compressible adjunct.

10. The staple cartridge assembly of claim 8, wherein a first subset of the structural cells has a first number of walls, wherein a second subset of the structural cells has a second number of walls that is different from the first number of walls.

11. The staple cartridge assembly of claim 8, wherein each of the plurality of walls comprise a non-uniform thickness.

12. The staple cartridge assembly of claim 8, wherein the structural cells include a first structural cell and a second structural cell, wherein the first structural cell is positioned adjacent to the second structural cell, and wherein the first structural cell and second structural cell share at least one wall of the plurality of walls.

13. The staple cartridge assembly of claim 8, wherein each structural cell comprises an initial height, and wherein the initial height is reduced to a compressed height based on a compressive force applied to the compressible adjunct.

14. The staple cartridge assembly of claim 13, wherein the initial height is a first initial height of a first structural cell and the compressed height is a first compressed height of the first structural cell, wherein a second structural cell has a second initial height that is reduced to a second compressed height based on the compressive force applied to the compressible adjunct, and wherein the first compressed height and the second compressed height are different.

15. A compressible adjunct, comprising:
    a first biocompatible layer;
    a second biocompatible layer, wherein the first biocompatible layer is spaced apart from the second biocompatible layer; and
    structural cells defined by a plurality of walls, wherein the structural cells are positioned between the first biocompatible layer and the second biocompatible layer.

16. The compressible adjunct of claim 15, wherein the structural cells are configured to define first openings comprising a first size, wherein the compressible adjunct further comprises second openings comprising a second size different than the first size, and wherein the first openings and second openings cooperate to define a continuous path through the compressible adjunct.

17. The compressible adjunct of claim 15, wherein a first subset of the structural cells has a first number of walls, wherein a second subset of the structural cells has a second number of walls that is different from the first number of walls.

18. The compressible adjunct of claim 15, wherein the structural cells include a first structural cell and a second structural cell, wherein the first structural cell is positioned adjacent to the second structural cell, and wherein the first structural cell and second structural cell share at least one wall of the plurality of walls.

19. The compressible adjunct of claim 15, wherein each structural cell comprises an initial height, and wherein the initial height is reduced to a compressed height based on a compressive force applied to the compressible adjunct.

20. The compressible adjunct of claim 19, wherein the initial height is a first initial height of a first structural cell and the compressed height is a first compressed height of the first structural cell, wherein a second structural cell has a second initial height that is reduced to a second compressed height based on the compressive force applied to the compressible adjunct, and wherein the first compressed height and the second compressed height are different.

* * * * *